(12) United States Patent
Behan et al.

(10) Patent No.: US 8,546,378 B2
(45) Date of Patent: Oct. 1, 2013

(54) 5HT$_{2C}$ RECEPTOR MODULATOR COMPOSITIONS AND METHODS OF USE

(75) Inventors: Dominic P. Behan, San Diego, CA (US); Brian M. Smith, San Diego, CA (US); Christina Bjenning, Solana Beach, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 13/418,151

(22) Filed: Mar. 12, 2012

(65) Prior Publication Data

US 2012/0252786 A1   Oct. 4, 2012

Related U.S. Application Data

(62) Division of application No. 11/793,941, filed as application No. PCT/US2005/046654 on Dec. 21, 2005, now Pat. No. 8,153,621.

(60) Provisional application No. 60/688,901, filed on Jun. 8, 2005, provisional application No. 60/638,667, filed on Dec. 23, 2004.

(51) Int. Cl.
*A61K 31/55* (2006.01)
*A61K 31/50* (2006.01)

(52) U.S. Cl.
USPC ............ 514/212.02; 514/247; 514/909

(58) Field of Classification Search
USPC ............ 514/212.02, 215, 217.01, 909, 247
See application file for complete search history.

(56) References Cited

U.S. PATENT DOCUMENTS

| | | |
|---|---|---|
| 3,652,543 A | 3/1972 | Hoegerle, Karl |
| 3,716,639 A | 2/1973 | Hoegerle et al. |
| 3,795,683 A | 3/1974 | Brossi et al. |
| 4,108,989 A | 8/1978 | Holden |
| 4,111,957 A | 9/1978 | Holden et al. |
| 4,210,729 A | 7/1980 | Hermans et al. |
| 4,210,749 A | 7/1980 | Shetty |
| 4,233,217 A | 11/1980 | Shetty |
| 4,477,378 A | 10/1984 | Gold et al. |
| 4,541,954 A | 9/1985 | Borowski et al. |
| 4,584,293 A | 4/1986 | Reiffen et al. |
| 4,737,495 A | 4/1988 | Bomhard et al. |
| 4,762,845 A | 8/1988 | Chu et al. |
| 4,957,914 A | 9/1990 | Clark et al. |
| 4,988,690 A | 1/1991 | Effland et al. |
| 5,015,639 A | 5/1991 | Berger et al. |
| 5,178,786 A | 1/1993 | Jahnke et al. |
| 5,247,080 A | 9/1993 | Berger et al. |
| 5,275,915 A | 1/1994 | Kojima et al. |
| 5,387,685 A | 2/1995 | Powell et al. |
| 5,412,119 A | 5/1995 | Brussee et al. |
| 5,422,355 A | 6/1995 | White et al. |
| 5,691,362 A | 11/1997 | McCormick et al. |
| 5,750,520 A | 5/1998 | Danilewicz et al. |
| 5,795,895 A | 8/1998 | Anchors |
| 5,856,503 A | 1/1999 | Aebi et al. |
| 5,861,393 A | 1/1999 | Danilewicz et al. |
| 5,908,830 A | 6/1999 | Smith et al. |
| 5,925,651 A | 7/1999 | Hutchinson |
| 5,939,415 A | 8/1999 | Laufer et al. |
| 5,942,535 A | 8/1999 | Laufer et al. |
| 5,958,943 A | 9/1999 | Laufer et al. |
| 6,087,346 A | 7/2000 | Glennon et al. |
| 6,218,385 B1 | 4/2001 | Adam et al. |
| 6,900,313 B2 | 5/2005 | Wasserscheid et al. |
| 6,953,787 B2 | 10/2005 | Smith et al. |
| 6,972,295 B2 | 12/2005 | Hagmann et al. |
| 7,105,523 B2 | 9/2006 | Stasch et al. |
| 7,157,466 B2 | 1/2007 | McClure et al. |
| 7,173,037 B2 | 2/2007 | Alonso-Alija et al. |
| 7,211,591 B2 | 5/2007 | Tajima et al. |
| 7,229,991 B2 | 6/2007 | Merla et al. |
| 7,230,024 B2 | 6/2007 | Carpino et al. |
| 7,232,823 B2 | 6/2007 | Carpino et al. |
| 7,514,422 B2 | 4/2009 | Smith et al. |
| 7,704,993 B2 | 4/2010 | Smith et al. |
| 2003/0105106 A1 | 6/2003 | Chiang et al. |
| 2004/0101575 A1 | 5/2004 | Hinz et al. |
| 2007/0060568 A1 | 3/2007 | Smith et al. |
| 2007/0275949 A1 | 11/2007 | Smith et al. |
| 2008/0009478 A1 | 1/2008 | Smith et al. |
| 2008/0045502 A1 | 2/2008 | Wolgast et al. |
| 2009/0143576 A1 | 6/2009 | Weigl et al. |
| 2010/0004223 A1 | 1/2010 | Agarwal et al. |
| 2010/0173894 A1 | 7/2010 | Brian et al. |
| 2010/0305316 A1 | 12/2010 | Garbaoui et al. |

FOREIGN PATENT DOCUMENTS

| | | |
|---|---|---|
| AU | 515236 | 3/1981 |
| CA | 1090797 | 12/1980 |
| CA | 2197789 | 8/1995 |
| CH | 500194 | 12/1970 |
| DE | 1914456 | 6/1971 |
| DE | 3315106 | 11/1983 |
| DE | 3418270 | 11/1985 |
| DE | 1944121 | 10/2003 |
| EP | 0007070 | 7/1979 |
| EP | 080779 | 6/1983 |
| EP | 096838 | 12/1983 |
| EP | 0161350 | 11/1985 |
| EP | 0174118 | 3/1986 |
| EP | 0204349 | 12/1986 |
| EP | 0285287 | 10/1988 |

(Continued)

OTHER PUBLICATIONS

Silverstone, "Appetite Suppressants: A Review", Drugs, vol. 43, No. 6, pp. 820-836 (Jun. 1992) Abstract enclosed.*

(Continued)

*Primary Examiner* — Kevin E Weddington

(57) ABSTRACT

The present invention relates to a composition comprising phentermine and a selective 5HT-2C receptor agonist. In addition, the invention relates to a composition comprising phentermine and a selective 5HT-2C receptor agonist having Formula (I): or a pharmaceutically acceptable salt, solvate or hydrate thereof. These compositions are useful in pharmaceutical compositions whose use includes the treatment of obesity.

6 Claims, 12 Drawing Sheets

(56) References Cited

FOREIGN PATENT DOCUMENTS

| | | |
|---|---|---|
| EP | 0285919 A1 | 10/1988 |
| EP | 0331130 A1 | 9/1989 |
| EP | 0285287 A3 | 8/1990 |
| EP | 0331130 B1 | 9/1993 |
| EP | 0285919 | 10/1994 |
| EP | 0987235 | 3/2000 |
| EP | 1074549 | 2/2001 |
| EP | 0987235 B1 | 3/2003 |
| EP | 1074549 B1 | 11/2003 |
| GB | 1196229 | 6/1970 |
| GB | 1221324 | 2/1971 |
| GB | 1225053 | 3/1971 |
| GB | 1247306 | 9/1971 |
| GB | 1268243 | 3/1972 |
| GB | 1599705 | 10/1981 |
| GB | 2133401 | 7/1984 |
| JP | 62-267250 | 11/1987 |
| JP | 5-339263 | 12/1993 |
| JP | 6-62574 | 8/1994 |
| JP | 6-298746 | 10/1994 |
| JP | 8-134048 | 5/1996 |
| JP | 9-030960 | 2/1997 |
| JP | 9-087258 | 3/1997 |
| JP | 2000-044533 | 2/2000 |
| JP | 2001-89472 | 4/2001 |
| NL | 7807819 | 1/1980 |
| SU | 1238732 | 6/1986 |
| WO | WO-88/07858 | 10/1988 |
| WO | WO-91/19698 | 12/1991 |
| WO | WO-93/00094 | 1/1993 |
| WO | WO 93/03015 | 2/1993 |
| WO | WO-95/13274 | 5/1995 |
| WO | WO-96/04271 | 2/1996 |
| WO | WO-96/05194 | 2/1996 |
| WO | WO-96/33993 | 10/1996 |
| WO | WO-97/24364 | 7/1997 |
| WO | WO-98/06701 | 2/1998 |
| WO | WO-98/40385 | 9/1998 |
| WO | WO-99/24411 | 5/1999 |
| WO | WO-02/40471 | 5/2002 |
| WO | WO-02/48124 A2 | 6/2002 |
| WO | WO-02/074746 | 9/2002 |
| WO | WO 02/074746 | 9/2002 |
| WO | WO-03/000663 | 1/2003 |
| WO | WO-03/027068 A2 | 4/2003 |
| WO | WO 03/057161 | 7/2003 |
| WO | WO 03/062205 | 7/2003 |
| WO | WO-03/062392 A2 | 7/2003 |
| WO | WO 03/086306 A2 | 10/2003 |
| WO | WO-2004/037788 | 5/2004 |
| WO | WO-2005/003096 | 1/2005 |
| WO | WO 2005/016902 | 2/2005 |
| WO | WO-2005/019179 A2 | 3/2005 |
| WO | WO-2005/019179 A3 | 3/2005 |
| WO | WO 2005/019180 | 3/2005 |
| WO | WO 2005/042490 | 5/2005 |
| WO | WO 2005/042491 | 5/2005 |
| WO | WO 2005/082859 | 9/2005 |
| WO | WO-2006/013209 A2 | 2/2006 |
| WO | WO-2006/043710 | 4/2006 |
| WO | WO-2006/069363 A2 | 6/2006 |
| WO | WO-2006/071740 A2 | 7/2006 |
| WO | WO-2006/069363 A3 | 5/2007 |
| WO | WO-2007/120517 A2 | 10/2007 |
| WO | WO-2007/120517 A3 | 10/2007 |
| WO | WO 2008/070111 A2 | 6/2008 |
| WO | WO-2008/070111 A3 | 8/2008 |
| WO | WO-2009/111004 | 9/2009 |

OTHER PUBLICATIONS

"Remington's Pharmaceutical Sciences" 17ed., Mack Publishing Company, Easton Pa.: 1409-1423, (1985).

"Arena Pharmaceuticals Initiates Clinical Trial of Novel Anti-Obesity Drug", Press Release, Feb. 24, 2004, 1 page.

"Arena Pharmaceuticals Reports Successful Phase 1a Safety and Clinical Pharmacology Trial Results of Novel Anti-Obesity Compound", Press Release, Jul. 14, 2004, 2 pages.

"Arena Pharmaceuticals Initiates Phase 1b Clinical Trial of Novel Anti-Obesity Drug", Press Release, Jul. 26, 2004, 1 page.

"Arena Pharmaceuticals Announces Results of its Phase 1b Safety Study for its Novel Anti-Obesity Compound", Press Release, Nov. 3, 2004, 2 pages.

"Arena Pharmaceuticals Announces Results of its Phase 1b Safety Study for its Novel Anti-Obesity Compound", Press Release, Nov. 30, 2004, 2 pages.

"Arena Pharmaceuticals Initiates Phase 2 Efficacy Study for its Novel Anti-Obesity Compound", Press Release, Dec. 22, 2004, 2 pages.

Bagnol et al., "Obesity and Hypothalamic Signaling: Role of GPCRs", Presentation, Arena Pharmaceuticals, Inc., Jul. 30, 2010, 30 pages.

Barnes, Pharmacological Strategies for Relapse Prevention in Schizophrenia, Psychiatry, 3(10):37-40, (2004).

Bickerdike, "5-HT$_{2C}$ receptor agonists as potential drugs for the treatment of obesity", Curr Top Med Chem, 3(8):885-97, (2003).

Binetti, et al., "Behavioral Disorders in Alzheimer Disease: A Transcultural Perspective", Arch Neurol. vol. 55, pp. 539-544, (1998).

Bos, et al., "Novel Agonists of 5-HT$_{2C}$-Receptors. Synthesis and Biological Evaluation of Substituted 2-{Indol-I-yl)-I-methylethylamines and 2-(Indeno[1,2-bjpyrrol-I-yl)-I-methylethylamines. Improved Therapeutics for Obsessive Compulsive Disorder", Journal of Medicinal Chemistry 40(17), 2762-2769, (1997).

Callahan et al., "Fluoxetine Increases the Anorectic and Long-Term Dopamine-Depleting Effects of Phentermine", Synapse, Dec. 15, 2000; 38(4):471-6.

Casy, et al., "Some Arylalkylamino Analogs of Acyclic Analgetics", J Med Chem, (1968), 11(3):599-601.

Cheng, "Fen/Phen and Valvular Heart Disease: The Final Link Has Now Been Established", Circulation 2000;102;e180.

Clinical trial NCT00768612, "Study Evaluating Safety and Tolerability of Vabicaserin in Patents With Sudden Worsening of Schizophrenia Study", http://clinicaltrials.gov/ct2/show/record/NCTOO768612, (2008).

Connolly et al., "Selections from Current Literature: Pharmacological Treatment of Obesity", Family Practice, vol. 15, No. 1, Oxford University Press 1998.

De Marinis, et al., "Development of an Affinity Ligand for Purification of $\alpha_2$-Adrenoceptors from Human Platelet Membranes", J. Med. Chem., 27, 918-921, (1984).

Deady, et al. "Synthesis of some tetrahydro-2- and 3-benzazepines, and of hexahydro-3-benzazocine" Journal of the Chemical Society, Perkins Transactions 1, pp. 782-783, (1973).

Dhonnchadha, et al., "Anxiolytic-like Effects of 5-HT$_2$ Ligands on Three Mouse Models of Anxiety", Behavioral Brain Research, 140:203-214, (2003).

Di Chiara, et al., "Reward System and Addiction: What Dopamine Does and Doesn't Do," Current Opinion in Pharmacology, 7:69-76, (2007).

Di Chiara, "Nucleus accumbens shell and core dopamine: differential role in behavior and addiction," Behavioural Brain Research, 137:75-114, (2002).

Di Giovanni, et al., "Serotonin/dopamine interaction—Focus on 5-HT$_{2C}$ receptor, a new target of psychotropic drugs", Indian Journal of Experimental Biology, vol. 40:1344-1352, (2002).

Di Matteo, et al., "Role of 5-HT$_{2C}$ Receptors in the Control of Central Dopamine Function," Trends in Pharmacological Sciences, 22(5):229-232, (2001).

Dixit et al., "gents Acting on Central Nervous System: Part XXIII-$_2$-Substituted 1,2,3,4,6,7,I2,I2a-Octahydropyrazino[2,I-b][3] benzazepines & 3-Substituted 1,2,3,4,4a,5,6,I1-Octahydropyrazin[I,2-b][2] benzazepines", CDRI Communication No. 1969, 893-97, (1974).

Flannery-Schroeder, "Reducing Anxiety to Prevent Depression," Am. J. Prev. Med. 31(6S1):S136-S142, (2006).

Frankle, et al., "Brain Serotonin Transporter Distribution in Subjects With Impulsive Aggressivity: A Positron Emission Study With [$^{11}$C]McN 5652", American Journal of Psychiatry, vol. 162, pp. 915-923, (2005).

Garrison, "Defining obesity: an adventure in cardiovascular disease epidemiology", Journal of Nutritional Biochemistry,9(9),493-500, (1998).

Gerace, et al., "Predictors of Weight Increases over 7 Years in Fire Fighters and Paramedics," Preventive Medicine, 25:593-600, (1996).

Gobert, et al., "Serotonin$_{2c}$ Receptors Tonically Suppress the Activity of Mesocortical Dopaminergic and Adrenergic, But Not Serotonergic, Pathways: A Combined Dialysis and Electrophysiological Analysis in the Rat," Synapse, 36:205-221, (2000).

Griesser, "Polymorphism in the Pharmaceutical Industry," ed. Rolf Hilfiker, Wiley,VCH Verlag GmbH & Co.: pp. 211-233, (2006).

Guillory, "Generation of Polymorphs, Hydrates, Solvates, and Amorphous Solids", in Polymorphism in Pharmaceutical Solids, ed. Harry G. Brittain, vol. 95, chapter 5, Marcel Dekker, Inc., New York, pp. 183-226, (1999).

Halford, "Obesity drugs in clinical development", Curr Opin Investig Drugs, 7(4):312-8, (2006).

Heisler et al., "Activation of Central Melanocortin Pathways by Fenfluramine", Science, vol. 297, Jul. 26, 2002.

Helferich, et al., "Uber Derivate Einger chinolincarbonsauren," J. Fur Praktische Chemie, vol. 33, 39-48, (1966).

International Search Report dated Nov. 22, 2004 for International Application No. PCT/US04/019670.

International Search Report for International Application No. PCT/US2004/034917 dated Feb. 2, 2005.

International Search Report for International Application No. PCT/US2004/034914 dated Mar. 15, 2005.

International Search Report dated Jan. 22, 2007 in application PCT/US2005/046983.

International Search Report dated Oct. 16, 2003 in application PCT/US2003/11076.

Isaac, "The 5-HT$_{2C}$ receptor as a potential therapeutic target for the design of antiobesity and antiepileptic drugs", Drugs of the Future, 26(4), 383-393, (2001).

Jandacek, "APD-356 (Arena)", Current Opinion in Investigational Drugs 6(10):1051-1056, (2005).

Jensen, "Potential role of new therapies in modifying cardiovascular risk in overweight patients with metabolic risk factors", Obesity (Silver Spring), 14 Suppl 3:143S-149S, (2006).

Klein, "Outcome Success in Obesity", Obesity Research, 9(suppl. 4):354S-358S, (2001).

Koplan, et al., "Preventing Childhood Obesity: Health in the Balance, Executive Summary", http://www.nap.edu/catalog/11015.html, 41 pages, (2005).

Krull, et al., "Synthesis and structure/NMDA receptor affinity relationships of 1-substituted tetrahydro-3-benzazepines", Bioorganic & Medicial Chemistry, 12(6), 1439-1451, (2004).

Lacivita, et al., "Selective agents for serotonin$_{2C}$ (5-HT$_{2C}$) receptor", Curr Top Med Chem,;6(18):1927-70, (2006).

Lam, et al., (eds) Canadian Consensus Guidelines for the Treatment of Seasonal Affective Disorder, Clinical & Academic Publishing, Vancouver, BC, Canada, (1999).

Loke et al., "Appetite Suppressants and Valvular Heart Disease—A Systematic Review", BMC Clinical Pharmacology, 2002, 2:6, 10 pages.

Martin, et al., "5-HT$_{2C}$ receptor agonists pharmacological characteristics and therapeutic potential", Journal of Pharmacology and Experimental Therapeutics, 286(2), 913-924, (1998).

Millan, et al., "5-HT2c Receptors Mediate Penile Erections in Rats: Actions of Novel and Selective Agonists and Antagonists", Eur. J. Pharmacol. 325:9-12, (1997).

Moline, et al., "Postpartum Depression: A Guide for Patients and Families," ExpertConsensus Guidelines Series—Treatment of Depression in Woman, Mar. 2001: 112-113, (2001).

Nagase, et al., "An anhydrous polymorphic form of trehalose," Carbohydrate Research 337(2),167-173 (Abstract Only), (2002).

Navarro-Vasquez, et al., "A study of aryl radical cyclization in enaminone esters," J.Org. Chem. 67:3213-20, (2002).

NIDA Research Monograph 27, 1979; Problems of Drug Dependence, Proceedings of the 41st Annual Scientific Meeting, The Committee on Problems of Drug Dependence, Inc., (1979).

Niendam, et al., "Neurocognitive Performance and Functional Disability in the Psychosis Prodrome," Schizophrenia Research, 84:100-111, (2006).

Porras, et al., "5-HT$_{2A}$ and 5-HT$_{2C/2B}$ Receptor Subtypes Modulate Dopamine ReleaseInduced in Vivo by Amphetamine and Morphine in Both the Rat Nucleus Accumbensand Striatum," Neuropsychopharmacology, 26: 311-324, (2002).

Prous Science Integrity entry 156186, (2007).

Prous Science Integrity entry 354056, (2007).

Rosenzweig-Lipson, et al., "Vabicaserin: effects of a novel 5-HT2C agonist on medial prefrontal cortex neurotransmission, cognition and sensorimotor grating", 20th ECNP Congress, Vienna, Austria, (2007).

Roth et al., "Anorectic Efficacy of the Fenfluramine/Phentermine Combination in Rats: Additivity or Synergy?", Eur J Pharmacol, Jun. 4, 1999, 373(2-3):127-34.

Rothman et al., "Evidence of Possible Involvement of 5-HT$_{2B}$ Receptors in the Cardiac Valvulopathy Associated with Fenfluramine and Other Serotonergic Medications", American Heart Assocation, Inc., 2000, 2836-41.

Rowland et al., "Acute Anorectic Effect of Single and Combined Drugs in Mice Using a Non-deprivation Protocol", Psychopharmacology (Berl). Sep. 2001; 157(2):193-6.

Rowland et al., "Anorectic Effect of Dehydroepiandrosterone Combined with Dexfenfluramine or Thionisoxetine", Eur J Pharmacol, May 4, 2001; 419(1):61-4.

Rowland et al., "Effects of the Cannabinoid Receptor Antagonist SR 141716, Alone and in Combination with Dexfenfluramine or Naloxone, on Food Intake in Rats", Psychopharmacology (Berl)., Dec. 2001; 159(1):111-6. Epub Oct. 2, 2001.

Rowland et al., "Comparison of Either Norepinephrine-uptake Inhibitors or Phentermine Combined with Serotonergic Agents on Food Intake in Rats", Psychopharmacology (Berl)., Mar. 2000; 149(1):77-83.

Schaffner, et al., "Preventing Severe Mental Illnesses—New Prospects and Ethical Challenges," Schizophrenia Research, 51:3-15, (2001).

"Silver Lining to the Cloud Over Anorexogen-Related Cardiac Valvulpathy?", Editorial, Annals of Internal Medicine, vol. 134, No. 4, Feb. 20, 2001, 3 pages.

Smith, "5-HT2C Receptor Agonists for the Treatment of Obesity", Presentation, Arena Pharmaceuticals, Inc., Jul. 28, 2010, 30 pages.

Smith, "Discovery of Lorcaserin (APD356): A Selective 5HT2C Agonist for the Treatment of Obesity", Presentation, Arena Pharmaceuticals, Inc., Jul. 21, 2006, 41 pages.

Smith, et al., "Discovery and SAR of New Benzazepines as Potent and Selective 5HT$_{2c}$ Receptor Agonists for the Treatment of Obesity," Bioorganic & Medicinal Chemistry Letters, 15(5):1467-1470, (2005).

Smith et al., "Discovery and Structure—Activity Relationship of (1R)-8-Chloro-2,3,4,5-tetrahydro-1-methyl-1H-3-benzazepine (Lorcaserin), a Selective Serotonin 5-HT2C Receptor Agonist for the Treatment of Obesity", J Med Chem 2008, 51, 305-313.

Sussman et al., "Effects of Nefazodone on Body Weight: A Pooled Analysis of Selective Serotonin Reuptake Inhibitor- and Imipramine-Controlled Trails", J Clin Psychiatry 62:4, Apr. 2001; 256-60.

Tecott, et al., "Eating Disorder and Epilepsy in Mice Lacking 5-HT$_{2C}$ Serotonin Receptors", Nature, 374:542-546, (1996).

Tohda, et al., "Molecular Pathopharmacology of 5-HT$_{2C}$ Receptors and the RNA Editing in the Brain", Journal of Pharmacological Science, vol. 100, pp. 427-432, (2006).

Tietze, et al., "Efficient synthesis of 2,3,4,5-tetrahydro-1H-3-benzazepines by intramolecular heck reaction", Institut fur Organische Chemie der Universitat Gottingen, Tammannstr.beta.e 2, D-3400 Gottingen, Germany, pp. 876-880, (1993).

Tsuang, et al., "Towards the Prevention of Schizophrenia", B245 Biol. Psychiatry, 48:349-356, (2000).

U.S. Appl. No. 11/793,941—Non-final Office Action (Restriction Requirement) dated Sep. 17, 2010.

Van Oekelen, et al., "5-HT$_{2A}$ and 5-HT$_{2C}$ receptors and their atypical regulation properties", Life Sciences, 72:2429-2449, (2003).
Vink, et al., "Risk Factors for Anxiety and Depression in the Elderly: A Review", J. Affect. Disord., doi:10.1016/j.jad.2007.06.005, 16 pages, (2007).
Webb, "APD356, A Potential New Treatment for Obesity", Presentation, Arena Pharmaceuticals, Inc., Aug. 11, 2005, 43 pages.
Wellman et al., "Synergistic Interactions Between Fenfluramine and Phentermine", Int J Obes Relat Metab Discord., Jul. 1999; 23(7):723-32.
Williams, "Chemistry Demystified", pp. 123, (2003).
Winkler, "Obesity and Haemostasis", Archives of Gynecology and Obstetrics, 261 (1), 25-29, (1997).
Wise, "Addiction Becomes a Brain Disease," Neuron, 26: 27-33, (2000).
Wisner, et al., "Postpartum Depression," N. Engl. J. Med., 347(3):194-199, (2002).
Yoshinaga, et al., "Prevention of Mildly Overweight Children from Development of More Overweight Condition," Prevention Medicine, 38:172-174, (2004).
U.S. Appl. No. 60/479,280, Smith et al.
U.S. Appl. No. 60/512,967, Burbaum et al.
U.S. Appl. No. 60/789,191, Arena Pharmaceutical.
U.S. Appl. No. 61/268,930, Arena Pharmaceutical.
Baindur, et al., "(±)-3-allyl-7-halo-8-hydroxy-1-phenyl-2,3,4,5-tetrahydro-1H-3-benzazepines as Selective High Affinity DI Dopamine Receptor Antagonists: Synthesis and Structure-Activity Relationship", J. Med. Chem., 35:67-72 (1992).
Bosch, et al., "Studies on the Synthesis of Pentacyclic Strychnos Indole Alkaloids. Photocyclization of N-chloroacetyl-1,2,3,4,5,6-hexahydro-1,5-methanoazocino [4,3-b] Indole Derivatives", Tetrahedron, 41(12):2557-66 (1985).
Bremner, "Seven Membered Rings", Institute for Biomolecular Science, Dept. of Chemistry, University of Wollongong; "Progress in Heterocyclic Chemistry 13", Pergamon Press, Ch. 7:340-77 (2001).
Chahal, IDdb Meeting Report 2000, May 17-18.
Chang, et al., "Dopamine Receptor Binding Properties of Some 2,3,4,5-Tetrahydro-1H-3-Benzazepine-7-ols With Non-Aromatic Substituents in the 5-Position", Bioorganic & Med. Chem. Letters, (1992) 2(5);399-402.
Chumpradit, et al., "(±)-7-chloro-8-hydroxyl-I-(4'-['2SI]iodophenyl)-3-methyl-2,3,4,5-tetrahydro-1H-3-benzazepine: A Potential CNS D-1 Dopamine Receptor Imaging Agent", J. Med. Chem., 32:1431-5 (1989).
Clark, et al., "1,9-alkano-bridged 2,3,4,5-tetrahydro-IH-3-benzazepines with Affinity for the c-Adrenoceptor and the 5-HT$_{2A}$ Receptor", J. Med. Chem., 33:633-41 (1990).
Deady, et al., "Synthesis of Some Tetrahydro-2- and 3-benzazepines, and of Hexahydro-3-benzazocine", JCS Perkin I, 782-3 (1973).
Draper, et al., "Novel Stereoselective Syntheses of the Fused Benzazepine Dopamine Di Antagonist (6aS, 13bR)-11-chloro-6,6a,7,8,9,13b-hexahydro-7-methyl-5H-benzo[d]naphth[2,1-b]azepin-12-ol(Sch 39166): 2. L-Homophenylalanine-Based Syntheses", Organic Process Research & Development, 2(3):186-93 (1998).
Draper, et al., "Novel Stereoselective Syntheses of the Fused Benzazepine Dopamine Dr Antagonist (6aS, 13bR)-11-chloro-6,6a,7,8,9,13b-hexahydro-7-methyl-5H-benzo[d]naphth[2,1-b]azepin-12-ol(Sch 39166): 1. Aziridinium Salt Based Syntheses", Organic Process Research & Development, 2(3):175-85 (1998).
Fuchs, et al., "Total Synthesis of (±)-Lennoxamine and (±)-Aphanorphine by Intramolecular Electrophilic Aromatic Substitution Reactions of 2-Amidoacroleins", Organic Letters, 3(24):3923-5 (2001).
Gallant et al., "U-22,394A: a controlled evaluation in chronic schizophrenic patients," Current Therapy Research, 9(11):579-81(1967).
Gardent, et al., "Sur Quelques Proprietes de l'Amino-2 Bromo-4 1H Benzazepine-3 et de ses derives", Bulletin de La Societe Chimique de France, 2:600-5 (1968) French Lang Only.
Gerritz, et al., "Two General Routes to 1,4-disubstituted-2,3,4,5-tetrahydro-IH-3-benzazepines", Organic Letters, 2(25):4099-102 (2000).

Gombar, et al., "Pharmacokinetics of a Series of 6-chloro-2,3,4,5-tetrahydro-3-substituted-IH—3-benzazepines in Rats", Drug Metabolism and Disposition, 16(3):367-72 (1988).
Halford et al., "Serotonergic Drugs: Effects on Appetite Expression and Use for the Treatment of Obesity," Drugs, 67(1):27-55 (2007).
Halford, et al., "o-Phenylenediacetimide and Other Compounds Related to 3,1H-Benzazepine", J. Org. Chem., 17:1646-52 (1952).
Hasan, et. al., "Syntheses of N-chloroacyl-beta-phenylethylamine Derivatives", Indian J. Chem., 9:1022-4 (1971).
Hassine-Coniac, et al., "Preparation et proprietes d'aldehydes dans la serie de la benzazepine-3", Bulletin de La Societe Chimique de France, 11:3985-92 (1971) French Lang Only.
Hazebroucq, "Acces a Des 1-H, Tetrahydro-2, 3, 4, 5 Benzazepines-3 One-1 et a Des Hexahydro Imidazo Isoquinoleines", Ann. Chim., t.I:221-54 (1966) French Lang Only.
Hester et al., "Azepinoindoles. I. Hexahyclroazepino[4,5-b)indoles," J. Med. Chem, 11(1):101-106 (1968).
Heys, et al., "A New Entry into C7-Oxygenated Tetrahydro-IH-3-benzazepines: Efficient Labeling with Carbon-14 in the Benzo Ring", J. Org. Chem., 54(19):4702-6 (1989).
Higgins et al, "Serotonin and drug reward: focus on 5-HT$_{2C}$ receptors," European Journal of Pharmacology, 480:151-162, (2003).
Hitzig, P., "Combined Serotonin and Dopamine Indirect Agonistscorrectalcohol Craving and Alcohol-Associated Neuroses," Journal of Substance Abuse Treatment, 11(5):489-90 (1994).
Im et al., "Positive Allosteric Modulator of the Human 5-HT$_{2C}$ Receptor," MolecularPharmacology, 64: 78-84 (2003).
Jenck et al., "Antiaversive effects of 5-HT$_{2C}$ receptor agonists and fluoxetine in a model of panic-like anxiety in rats," European Neuropsychopharmacology, 8:161(1998).
Kaiser, et al., "6-(phenylthio)-substituted 2,3,4,5-tetrahydro-IH-3-benzazepines, a Novel Class of Dopamine Receptor Antagonists and Neuroleptics", J. Med. Chem., 23(9):975-6 (1980).
Klohr, et al., "An Intramolecular Photocyclization to Form the Azepino[3,4,5-cd]Indole System", Synthetic Communications, 18(7):671-4 (1988).
Kuenburg, et al., "Development of a Pilot Scale Process for the Anti-Alzheimer Drug (–)-Galanthamine Using Large-Scale Phenolic Oxidative Coupling and Crystallisation-Induced Chiral Conversion", Organic Process Research & Development, 3(6):425-31 (1999).
Ladd, et al., "Synthesis and Dopaminergic Binding of 2-Aryldopamine Analogues: Phenethylamines, 3-Benzazepines, and 9-(Aminomethyl)flourenes", J. Med. Chem., (1986) 29(10):1904-1912.
Lennon, et al., "Azabenzocycloheptenones. Part XVIII.' Amines and Amino-ketones of the Tetrahydro-3-benzazepin-I-one Series", J.C.S. Perkin I, 7:622-6 (1975).
Lin, et al., "Benzindene Prostaglandins. Synthesis of Optically Pure 15-Deoxy-U-68,215 and its Enantiomer via a Modified Intramolecular Wadsworth-Emmons-Wittig Reaction", J. Org. Chem., 52(25):5594-601 (1987).
Macdonald, et al., "Design and Synthesis of trans-3-(2-(4-((3-(3-(5-methyl-1,2,4-oxadiazolyl))-phenyl)carboxamido)cyclohexyl)ethyl)-7-methylsulfonyl-2,3,4,5-tetrahydro-IH—3-benzazepine (SB-414796): A Potent and Selective Dopamine D3 Receptor Antagonist", J. Med. Chem., 46(23):4952-64 (2003).
Muller et all., "Intracellular 5-HT$_{2C}$-receptor dephosphorylation: a new target for treating drug addiction," Trends in Pharmacological Sciences, 27(9):455-58(2006).
Nagle, et al., "Efficient Synthesis of beta-amino Bromides", Tetrahedron Letters, 41:3011-4 (2000).
Nair, et al., "Preparation of 2,3,4,5-tetrahydro-3,1H-benzazepine-2-one", Indian J. Chem., 5:169-70 (1967).
Neumeyer, et al., "Development of a High Affinity and Stereoselective Photoaffinity Label for the D-1 Dopamine Receptor: Synthesis and Resolution of 7-[125I]Iodo-8-hydroxy-3-methyl-1-(4azidophenyl)-2,3,4,5-tetrahydro-III-3-benzazepine", J. Med. Chem., 33(2):521-6 (1990).
Okuno, et al., "Photocyclization of N-chloroacetyl-2,5-dimethoxyphenethylamine Synthesis of Pyrroloindoles", Chem. Pharm. Bull., 23(11):2584-90 (1975).

Orito et al., "Benzolactams-I: Alkylation of 1,2,4,5-tetrahydro-3-methyl-3H-3-benzazepin-2-one with sodium hydride and alkyl halide," Tetrahedron 36:1017-1021(1980) Pergamon Press Ltd.

Orito, et al., "Synthetic Studies of Heterocyclic Compounds I: Alkylation and Acylation of 1, 2, 4, 5-tetrahydro-3-methyl-3H-3-benzepin-2-one", Bulletin of the Faculty of Engineering, Hokkaido University (Hokkaido Kogakubu Kenkyu Hokuko), 96(54):41-4 (1979).

Orito, et al., "Total Synthesis of Pseudo Type of Protopine Alkaloids", Heterocycles, 14(1):11-4 (1980).

Pauvert, et al., "Silver Nitrate-Promoted Ring Enlargement of 1-tribromomethyl-1,2-dihydro- and 1-tribromethyl-1,2, 3,4-tetrahydro-isoquinoline Derivatives: Application to the Synthesis of the Anti-anginal Zatebradine", Tetrahedron Letters, 44:4203-6 (2003).

Pawan et al., "Preliminary study on the effects of fenfluramine derivative, 'S992' inman," British Journal of Pharmacology, 41(2): 416P-417P (1971).

Pecherer, et al., "A Novel Synthesis of Aromatic Methoxy and Methylenedioxy Substituted 2,3,4,5-tetrahydro-IH-3-benzazepines", J. Het. Chem., 9:609-16 (1972).

Pecherer, et al., "The Synthesis of Some 7- and 7,8-substituted 2,3,4,5-tetrahydro-IH-3-benzazepines", J. Het. Chem., 8:779-83 (1971).

Perry, et al., Prospective Study of Risk Factors for Development of Non-Insulin Dependent Diabetes in Middle Aged British Men, BMJ, 310:560-4 (1995).

Pfeiffer, et al., "Dopaminergic Activity of Substituted 6-chloro-I-phenyl-2,3,4,5-tetrahydro-IH-3-benzazepines", J. Med. Chem., 25(4)352-8 (1982).

Piesla, et al, (2001), Schizophrenia Research, 49:95.

Rothman R.B., "Treatment of Alcohol and Cocaine Addiction by the Combination of Pemoline and Fenfluramine: A Preliminary Case Series," Journal of Substance Abuse Treatment, 12(6):449-53 (1995).

Schlademan, et al., "Synthesis of 1-oxo- and 1-hydroxy-azabenzocycloalkanes", J.C.S. Perkin I, 2:213-5 (1972).

Smith, et al, Discovery and structure-activity relationship of (1R)-8-chloro-2,3,4,5-tetrahydro-1-methyl-1H-3-benzazepine (lorcaserin), in a selective serotonin 5-$HT_{2C}$ receptor agonist for the treatment of obesity, retreived from the internet on Dec. 21, 2007 <URL:http:pubs.acs.org/journals/jmcmar/index.html>.

Tietze, et al., "Efficient Synthesis of 2,3,4,5-Tetrahydro-1H-3-benzazepines by Intramolecular Heck Reaction", J. of Synthetic Organic Chem., (1993) pp. 876-880, Thieme Stuttgart, New York.

US Office Action dated Aug. 20, 2010 in U.S. Appl. No. 11/599,050.

Vanderlaan, et al., "Synthesis and Oxidative Coupling of (±)-3-oxoreticuline", J. Org. Chem., 50(6):743-7 (1985).

Weinstock, et al., "Separation of Potent Central and Renal Dopamine Agonist Activity in Substituted 6-chloro-2,3,4,5-tetrahydro-7,8-dihydroxy-I-phenyl-IH-3-benzazepines", J. Med. Chem., 23(9):973-5 (1980).

Wu, et al., "Amino Diol Based Asymmetric Syntheses of a Fused Benzazepine as a Selective D1 Dopamine Receptor", Organic Process Research & Development, 1(5):359-64 (1997).

Yasuda, et al., "A Novel and Stereoselective Synthesis of (+)-cephalotaxine and its Analogue", Tetrahedron Letters, 27(18):2023-6 (1986).

Yonemitsu, et al., "Photocyclization of Pharmacodynamic Amines. IV. Novel Heterocycles from N-chloroacetyl-3,4-dimethoxyphenethylamine", Journal of the American Chemical Society, 92(19):5686-90 (1970).

Yonemitsu, et al., "Photocyclization of Pharmodynamic Amines. II. X-Ray Analysis of a Noncentrosymmetric Tetracyclic Indole", Journal of the American Chemical Society, 90(23):6522-3 (1968).

Yonemitsu, et al., "Photocyclizations of Tyrosines, Tyramines, Catecholamines, and Normescaline", Journal of the American Chemical Society, 90(3):776-84 (1968).

Yonemitsu, et al., "Photolysis of N-chloroacetyl-O-methyl-L-tyrosine to an Azaazulene", Journal of the American Chemical Society, 89(4):1039-40 (1967).

* cited by examiner

5HT$_{2C}$ RECEPTOR MODULATOR COMPOSITIONS AND METHODS OF USE

CROSS-REFERENCE TO RELATED APPLICATIONS

This is a divisional of U.S. patent application Ser. No. 11/793,941 filed Apr. 11, 2008 entitled "5HT2C Receptor Modulator Compositions And Methods Of Use," which is a 35 USC 371 National Stage Entry of PCT/US2005/046654 filed Dec. 21, 2005, which claims the benefit of U.S. Provisional Application No. 60/688,901 filed Jun. 8, 2005, and U.S. Provisional Application No. 60/638,667 filed Dec. 23, 2004, each of which is incorporated herein by reference in its entirety.

FIELD OF THE INVENTION

The present invention relates to compounds which act as modulators of 5HT$_{2C}$ receptors, compositions including the compounds, and methods of using the compounds and compositions.

BACKGROUND OF THE INVENTION

Obesity is a life-threatening disorder in which there is an increased risk of morbidity and mortality arising from concomitant diseases such as type II diabetes, hypertension, stroke, cancer and gallbladder disease.

Obesity is now a major healthcare issue in the Western World and increasingly in some third world countries. The increase in numbers of obese people is due largely to the increasing preference for high fat content foods but also the decrease in activity in most people's lives. In the last 10 years there has been a 30% increase in the incidence of obesity in the USA such that currently about 30% of the population of the USA is now considered obese.

Whether someone is classified as overweight or obese is generally determined on the basis of their body mass index (BMI) which is calculated by dividing body weight (kg) by height squared (m$^2$). Thus, the units of BMI are kg/m$^2$ and it is possible to calculate the BMI range associated with minimum mortality in each decade of life. Overweight is defined as a BMI in the range 25-30 kg/m$^2$. and obesity as a BMI greater than 30 kg/m$^2$ (see Table 1 below).

TABLE 1

CLASSIFICATION OF WEIGHT
BY BODY MASS INDEX (BMI)

| BMI | CLASSIFICATION |
| --- | --- |
| <18.5 | Underweight |
| 18.5-24.9 | Normal |
| 25.0-29.9 | Overweight |
| 30.0-34.9 | Obesity (Class I) |
| 35.0-39.9 | Obesity (Class II) |
| >40 | Extreme Obesity (Class III) |

As the BMI increases there is an increased risk of death from a variety of causes that are independent of other risk factors. The most common diseases associated with obesity are cardiovascular disease (particularly hypertension), diabetes (obesity aggravates the development of diabetes), gall bladder disease (particularly cancer) and diseases of reproduction. Research has shown that even a modest reduction in body weight can correspond to a significant reduction in the risk of developing coronary heart disease.

There are problems however with the BMI definition in that it does not take into account the proportion of body mass that is muscle in relation to fat (adipose tissue). To account for this, obesity can also be defined on the basis of body fat content: greater than 25% in males and greater than 30% in females.

Obesity considerably increases the risk of developing cardiovascular diseases as well. Coronary insufficiency, atheromatous disease, and cardiac insufficiency are at the forefront of the cardiovascular complications induced by obesity. It is estimated that if the entire population had an ideal weight, the risk of coronary insufficiency would decrease by 25% and the risk of cardiac insufficiency and of cerebral vascular accidents would decrease by 35%. The incidence of coronary diseases is doubled in subjects less than 50 years of age who are 30% overweight. The diabetes patient faces a 30% reduced lifespan. After age 45, people with diabetes are about three times more likely than people without diabetes to have significant heart disease and up to five times more likely to have a stroke. These findings emphasize the inter-relations between risks factors for diabetes and coronary heart disease and the potential value of an integrated approach to the prevention of these conditions based on the prevention of obesity (Perry, I. J., et al., *BMJ* 310, 560-564 (1995)).

Diabetes has also been implicated in the development of kidney disease, eye diseases and nervous system problems. Kidney disease, also called nephropathy, occurs when the kidney's "filter mechanism" is damaged and protein leaks into urine in excessive amounts and eventually the kidney fails. Diabetes is also a leading cause of damage to the retina at the back of the eye and increases risk of cataracts and glaucoma. Finally, diabetes is associated with nerve damage, especially in the legs and feet, which interferes with the ability to sense pain and contributes to serious infections. Taken together, diabetes complications are one of the nation's leading causes of death.

The first line of treatment is to offer diet and life style advice to patients such as reducing the fat content of their diet and increasing their physical activity. However, many patients find this difficult and need additional help from drug therapy to maintain results from these efforts.

Most currently marketed products have been unsuccessful as treatments for obesity because of a lack of efficacy or unacceptable side-effect profiles. The most successful drug so far was the indirectly acting 5-hydroxytryptamine (5-HT) agonist d-fenfluramine (Redux™) but reports of cardiac valve defects in up to one third of patients led to its withdrawal by the FDA in 1998.

In addition, two drugs have recently been launched in the USA and Europe: Orlistat (Xenical™), a drug that prevents absorption of fat by the inhibition of pancreatic lipase, and Sibutramine (Reductil™), a 5-HT/noradrenaline re-uptake inhibitor. However, side effects associated with these products may limit their long-term utility. Treatment with Xenical™ is reported to induce gastrointestinal distress in some patients, while Sibutramine has been associated with raised blood pressure in some patients.

Serotonin (5-HT) neurotransmission plays an important role in numerous physiological processes both in physical and in psychiatric disorders. 5-HT has been implicated in the regulation of feeding behavior. 5-HT appears to work by inducing a feeling of fullness or satiety so eating stops earlier and fewer calories are consumed. It has been shown that a stimulatory action of 5-HT on the 5HT$_{2C}$ receptor plays an important role in the control of eating and in the anti-obesity effect of d-fenfluramine. As the 5-HT$_{2C}$ receptor is expressed in high density in the brain (notably in the limbic structures, extrapyramidal pathways, thalamus and hypothalamus, i.e. PVN and DMH, and predominantly in the choroid plexus) and is expressed in low density or is absent in peripheral tissues, a selective 5-HT$_{2C}$ receptor agonist can be a more effective and safe anti-obesity agent. Also, 5-HT$_{2C}$ knockout mice are overweight with cognitive impairment and susceptibility to seizure.

It is believed that 5HT$_{2C}$ may play a role in obsessive compulsive disorder, some forms of depression, and epilepsy. Accordingly, agonists can have anti-panic properties, and properties useful for the treatment of sexual dysfunction.

In sum, the 5HT$_{2C}$ receptor is a receptor target for the treatment of obesity and psychiatric disorders, and it can be seen that there is a need for selective 5HT$_{2C}$ agonists which safely decrease food intake and body weight. The present invention is directed to these, as well as other, important ends.

SUMMARY OF THE INVENTION

In a first aspect, the invention features a composition comprising phentermine and a selective 5HT-2C receptor agonist.

In a second aspect, the invention features a composition according to the first aspect where the selective 5HT-2C receptor agonist has Formula (I):

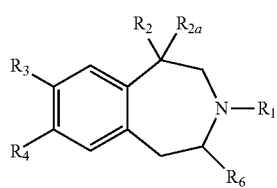

(I)

or a pharmaceutically acceptable salt, solvate or hydrate thereof.
wherein:
$R_1$ is H or $C_{1-8}$ alkyl;
$R_2$ is $C_{1-8}$ alkyl, —CH$_2$—O—$C_{1-8}$ alkyl, —C(═O)—O—$C_{1-8}$ alkyl, —C(═O)—NH—$C_{1-8}$ alkyl, OH, or CH$_2$OH;
$R_{2a}$ is H;
or $R_2$ and $R_{2a}$ together form —CH$_2$—CH$_2$—;
$R_3$ and $R_4$ are each independently H, halogen, perhaloalkyl, CN, OR$_5$, SR$_5$, NHR$_5$, N(R$_5$)$_2$, OH, aryl, or heteroaryl, wherein said aryl can be optionally substituted with up to two substituents selected from $C_{1-8}$ alkyl, halogen, perhalo alkyl, and alkoxy, and said heteroaryl can be optionally substituted with up to two substituents selected from halogen and $C_{1-8}$ alkyl;
or $R_3$ and $R_4$ together with the atoms to which they are attached can form a 5- or 6-member heterocyclic ring having one O atom;
each $R_5$ is independently $C_{1-8}$ alkyl, $C_{1-8}$ alkenyl, aryl, heteroaryl, arylalkyl, heteroarylalkyl or perhaloalkyl, or allyl; and
$R_6$ is H or $C_{1-8}$ alkyl.

In a third aspect, the invention features a composition according to the second aspect wherein:
$R_3$ is halogen, perhaloalkyl, CN, SR$_5$, NHR$_5$, N(R$_5$)$_2$, aryl, or heteroaryl, wherein said aryl can be optionally substituted with up to two substituents selected from $C_{1-8}$ alkyl, halogen, perhalo alkyl, and alkoxy, and said heteroaryl can be optionally substituted with up to two substituents selected from halogen and $C_{1-8}$ alkyl; and $R_4$ is H, halogen, perhaloalkyl, CN, SR$_5$, NHR$_5$, N(R$_5$)$_2$, aryl, or heteroaryl, wherein said aryl can be optionally substituted with up to two substituents selected from $C_{1-8}$ alkyl, halogen, perhalo alkyl, and alkoxy, and said heteroaryl can be optionally substituted with up to two substituents selected from halogen and $C_{1-8}$ alkyl;
wherein heteroaryl is pyrrolyl, pyrazolyl, imidazolyl, triazolyl, tetrazolyl, pyridyl, pyrimidinyl, furanyl, pyranyl, thienyl, benzimidazolyl, quinolinyl, isoquinolinyl, oxazolyl, thiazolyl or thiadiazolyl.

In a fourth aspect, the invention features a composition according to the second or third aspect wherein $R_1$ is H. In addition, the fourth aspect features a composition according to the second or third aspect wherein $R_1$ is methyl.

In a fifth aspect, the invention features a composition according to the second, third, or fourth aspect wherein $R_2$ is methyl, ethyl, n-propyl or isopropyl. In addition, the fifth aspect features a composition according to the second, third, or fourth aspect wherein $R_2$ is methyl or ethyl. Further, the fifth aspect features a composition according to the second, third, or fourth aspect wherein $R_2$ and $R_{2a}$ together form —CH$_2$CH$_2$—.

In a sixth aspect, the invention features a composition according to the second through fifth aspect wherein $R_3$ is chlorine. In addition, the sixth aspect features a composition according to the second through fifth aspect wherein $R_3$ is bromine. Further, the sixth aspect features a composition according to the second through fifth aspect wherein $R_3$ is perhaloalkyl. Also, the sixth aspect features a composition according to the second through fifth aspect wherein $R_3$ is CF$_3$. Further, the sixth aspect features a composition according to the second through fifth aspect wherein $R_3$ is selected from the group consisting of thienyl, furanyl, pyrrolyl, pyrazolyl and imidazolyl.

In a seventh aspect, the invention features a composition according to the second through sixth aspect wherein $R_4$ is selected from the group consisting of thienyl, furanyl, pyrrolyl, pyrazolyl and imidazolyl optionally substituted with one or two substituents selected from halogen or methyl. In addition, the seventh aspect features a composition according to the second through sixth aspect wherein $R_4$ is phenyl optionally substituted with up to two substituents selected from $C_{1-8}$ alkyl, halogen, and alkoxy.

In an eighth aspect, the invention features a composition according to the second aspect wherein:
$R_2$ is methyl, ethyl, isopropyl, or CH$_2$OH; or $R_2$ and $R_{2a}$ taken together form —CH$_2$CH$_2$—;
$R_3$ is halogen, or a 5-membered heteroaryl ring having up to two heteroatoms selected from O, N and S, and up to two substituents selected from halogen and $C_{1-8}$ alkyl;
$R_4$ is H, a 5-membered heteroaryl ring having up to two heteroatoms selected from O, N and S and up to two substituents selected from halogen and $C_{1-8}$ alkyl, or phenyl optionally substituted with up to two substituents selected from $C_{1-8}$ alkyl, halogen, and alkoxy;
$R_6$ is H or methyl; or a pharmaceutically acceptable salt, solvate or hydrate thereof.

In addition, the eighth aspect features a composition of the second aspect wherein:
$R_1$ is H;
$R_2$ is methyl;
$R_3$ is chlorine, bromine, or thienyl;
$R_4$ is pyrazolyl-3-yl or phenyl wherein said pyrazolyl-3-yl optionally has up to two substituents selected from halogen and $C_{1-8}$ alkyl, and said phenyl optionally has a single halogen substitutent; and R₆ is H; or a pharmaceutically acceptable salt, solvate or hydrate thereof.

Further, the eighth aspect features a composition of the second aspect wherein:
$R_1$ is H or Me;
$R_2$ is Me, Et, or OH;
$R_{2a}$ is H;
$R_3$ is F, CI, Br, I, CF$_3$, or 2-chlorophenyl;
$R_4$ is H; and
$R_6$ is H.

In addition, the eighth aspect features a composition of the second aspect wherein:
$R_1$ is H;
$R_2$ is $C_{1-8}$ alkyl;
$R_{2a}$ is H;
$R_3$ is halogen;
$R_4$ is H; and
$R_6$ is H.

In a ninth aspect, the invention features a composition according to the first or second aspect wherein said selective 5HT-2C receptor agonist is selected from the group consisting of:
8-chloro-1-methyl-2,3,4,5-tetrahydro-1H-3-benzazepine;
8-bromo-1-methyl-2,3,4,5-tetrahydro-1H-3-benzazepine;
8-iodo-1-methyl-2,3,4,5-tetrahydro-1H-3-benzazepine;
8-trifluoromethyl-1-methyl-2,3,4,5-tetrahydro-1H-3-benzazepine;
8-trifluoromethyl-1-ethyl-2,3,4,5-tetrahydro-1H-3-benzazepine;
8-chloro-1-ethyl-2,3,4,5-tetrahydro-1H-3-benzazepine;
8-bromo-1-ethyl-2,3,4,5-tetrahydro-1H-3-benzazepine;
8-iodo-1-ethyl-2,3,4,5-tetrahydro-1H-3-benzazepine;
7,8-dichloro-1-methyl-2,3,4,5-tetrahydro-1H-3-benzazepine;
7,8-dichloro-1-ethyl-2,3,4,5-tetrahydro-1H-3-benzazepine;
8-chloro-7-fluoro-1-methyl-2,3,4,5-tetrahydro-1H-3-benzazepine;
8-chloro-7-methoxy-1-methyl-2,3,4,5-tetrahydro-1H-3-benzazepine; and
8-chloro-7-fluoro-1-ethyl-2,3,4,5-tetrahydro-1H-3-benzazepine;
or a pharmaceutically acceptable salt, solvate or hydrate thereof.

In addition, the ninth aspect features a composition according to the first or second aspect wherein said selective 5HT-2C receptor agonist is (R)-8-chloro-1-methyl-2,3,4,5-tetrahydro-1H-3-benzazepine or a pharmaceutically acceptable salt, solvate or hydrate thereof.

In a tenth aspect, the invention features a composition according to the first through ninth aspect further comprising a pharmaceutically acceptable carrier.

In an eleventh aspect, the invention features a method of decreasing food intake of a mammal comprising administering to said mammal a pharmaceutically effective amount of a combination comprising an amount of (R)-8-chloro-1-methyl-2,3,4,5-tetrahydro-1H-3-benzazepine and an amount of phentermine, wherein said (R)-8-chloro-1-methyl-2,3,4,5-tetrahydro-1H-3-benzazepine and phentermine are provided in amounts to give a synergistic effect in decreasing food intake in said mammal. In one embodiment, the amount of (R)-8-chloro-1-methyl-2,3,4,5-tetrahydro-1H-3-benzazepine alone and the amount of phentermine alone are therapeutically sub-effective in decreasing food intake in said mammal.

In a twelfth aspect, the invention features a method of inducing satiety in a mammal comprising administering to said mammal a pharmaceutically effective amount of a combination comprising an amount of (R)-8-chloro-1-methyl-2,3,4,5-tetrahydro-1H-3-benzazepine and an amount of phentermine, wherein said (R)-8-chloro-1-methyl-2,3,4,5-tetrahydro-1H-3-benzazepine and phentermine are provided in amounts to give a synergistic effect in inducing satiety in said mammal. In one embodiment, the amount of (R)-8-chloro-1-methyl-2,3,4,5-tetrahydro-1H-3-benzazepine alone and the amount of phentermine alone are therapeutically sub-effective in inducing satiety in said mammal.

In a thirteenth aspect, the invention features a method of controlling weight gain of a mammal comprising administering to said mammal a pharmaceutically effective amount of a combination comprising an amount of (R)-8-chloro-1-methyl-2,3,4,5-tetrahydro-1H-3-benzazepine and an amount of phentermine, wherein said (R)-8-chloro-1-methyl-2,3,4,5-tetrahydro-1H-3-benzazepine and phentermine are provided in amounts to give a synergistic effect in controlling weight gain in said mammal. In one embodiment, the amount of (R)-8-chloro-1-methyl-2,3,4,5-tetrahydro-1H-3-benzazepine alone and the amount of phentermine alone are therapeutically sub-effective in controlling weight gain in said mammal.

In a fourteenth aspect, the invention features a method of prophylaxis or treatment of obesity comprising administering to a patient in need of such prophylaxis or treatment a pharmaceutically effective amount of a combination comprising an amount of (R)-8-chloro-1-methyl-2,3,4,5-tetrahydro-1H-3-benzazepine and an amount of phentermine, wherein said (R)-8-chloro-1-methyl-2,3,4,5-tetrahydro-1H-3-benzazepine and phentermine are provided in amounts to give a synergistic effect in decreasing food intake in said mammal. In one embodiment, the amount of (R)-8-chloro-1-methyl-2,3,4,5-tetrahydro-1H-3-benzazepine alone and the amount of phentermine alone are therapeutically sub-effective in decreasing food intake in said mammal.

In some embodiments, some of the foregoing methods of the invention further comprising the step of identifying a subject, said subject being in need of decreasing food intake, controlling weight gain, or treating obesity, wherein said identifying step is performed prior to administering to said subject said pharmaceutically effective amount of said compound or composition of the invention.

Applicants reserve the right to exclude any one or more of the compounds from any of the embodiments of the invention. Applicant additionally reserves the right to exclude any disorder from any of the embodiments of the invention.

DETAILED DESCRIPTION OF THE INVENTION

Figure 1A:
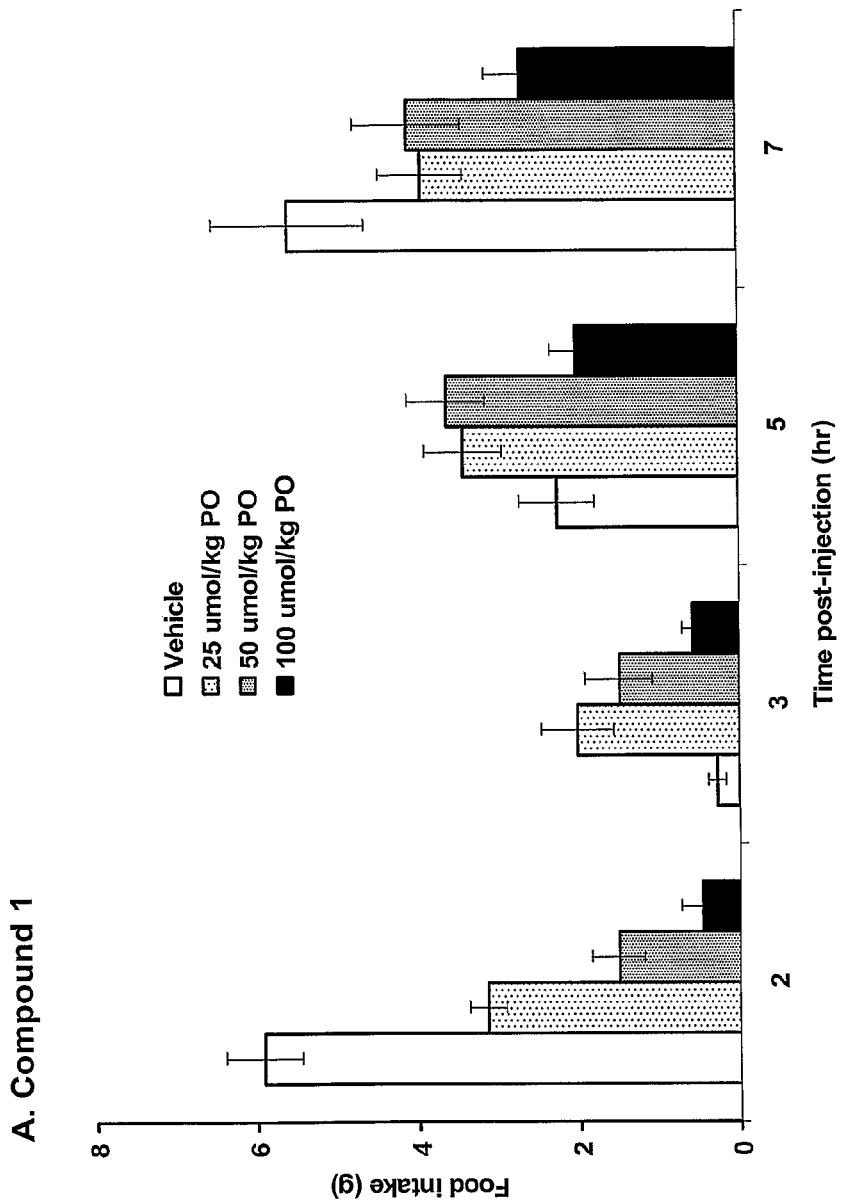
FIGS. 1A-1G illustrate the effects of seven different 5HT-2C receptor agonist compounds described in the invention on food intake in food-deprived rats.
Figure 1B:
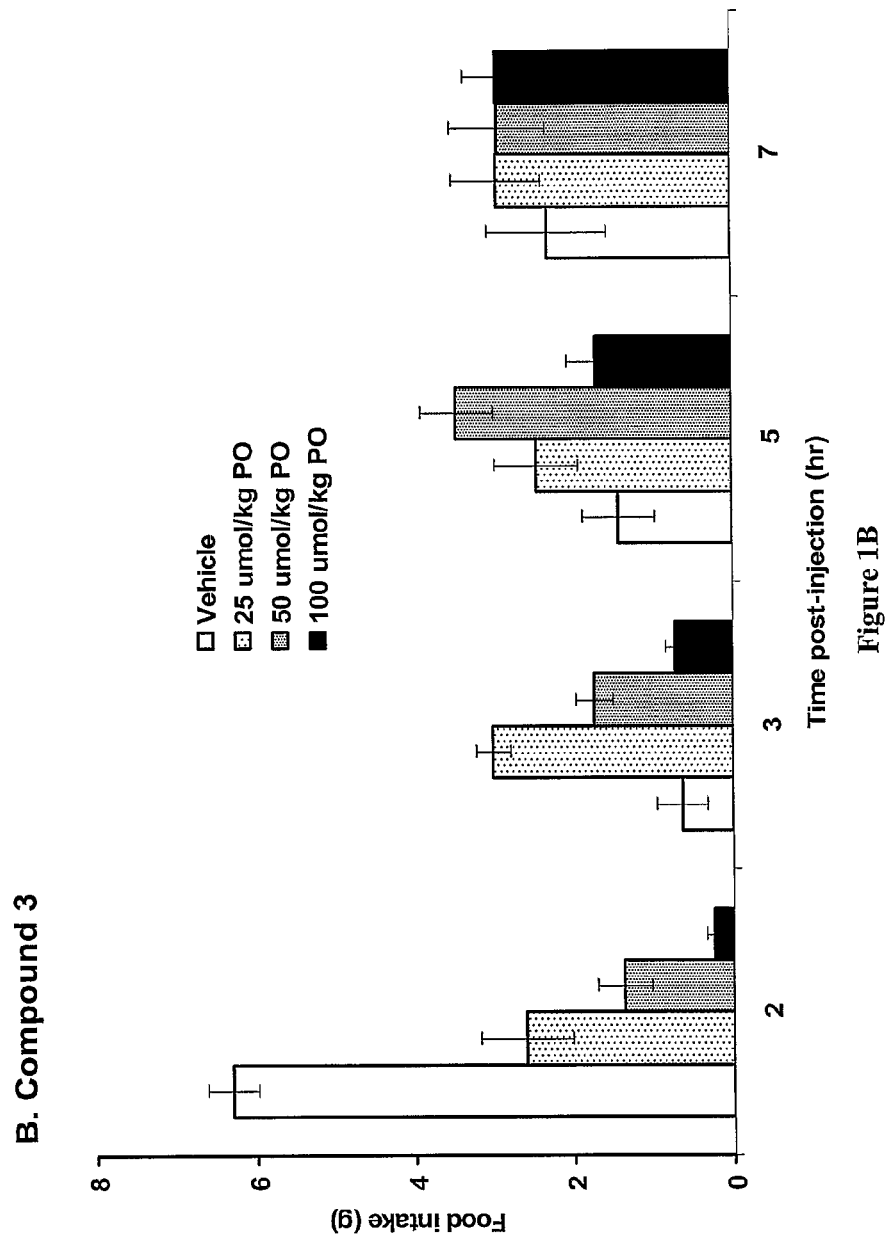
Figure 1C:
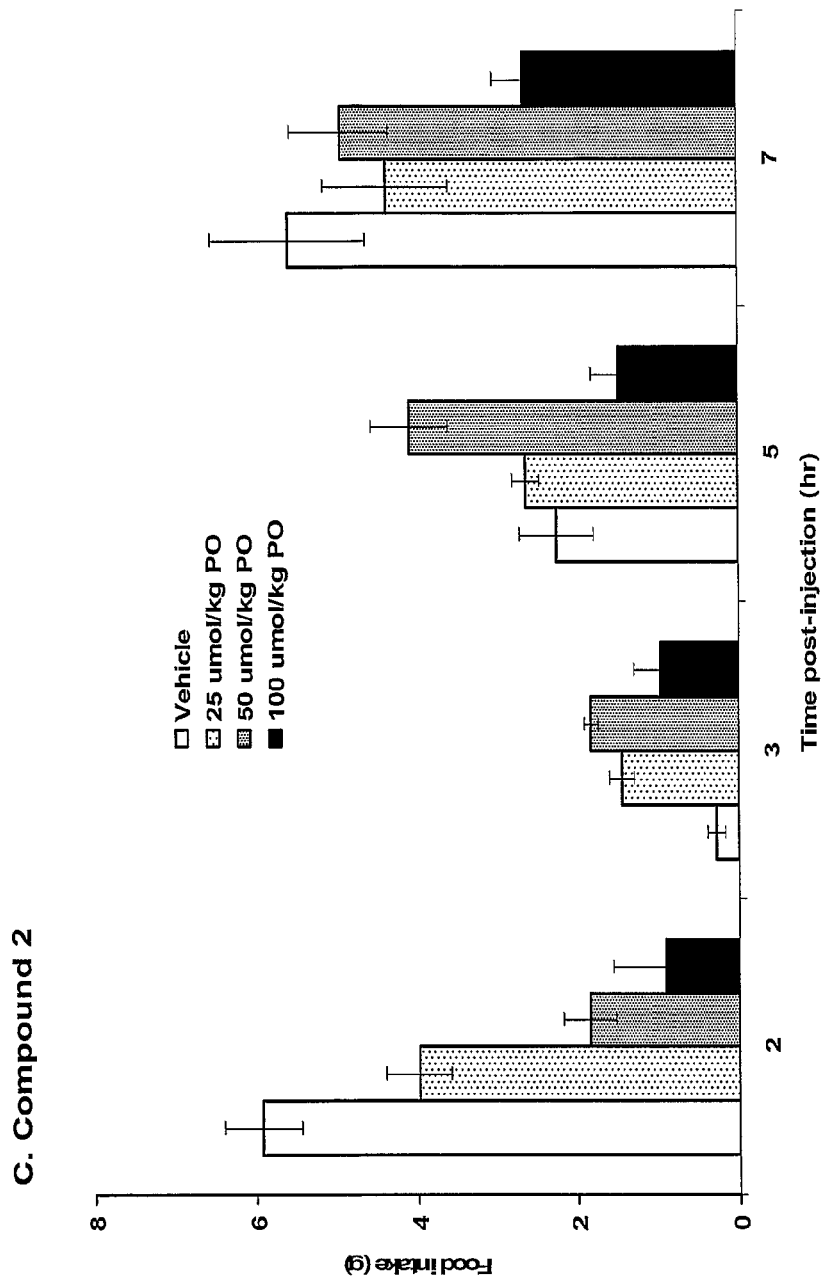
Figure 1D:
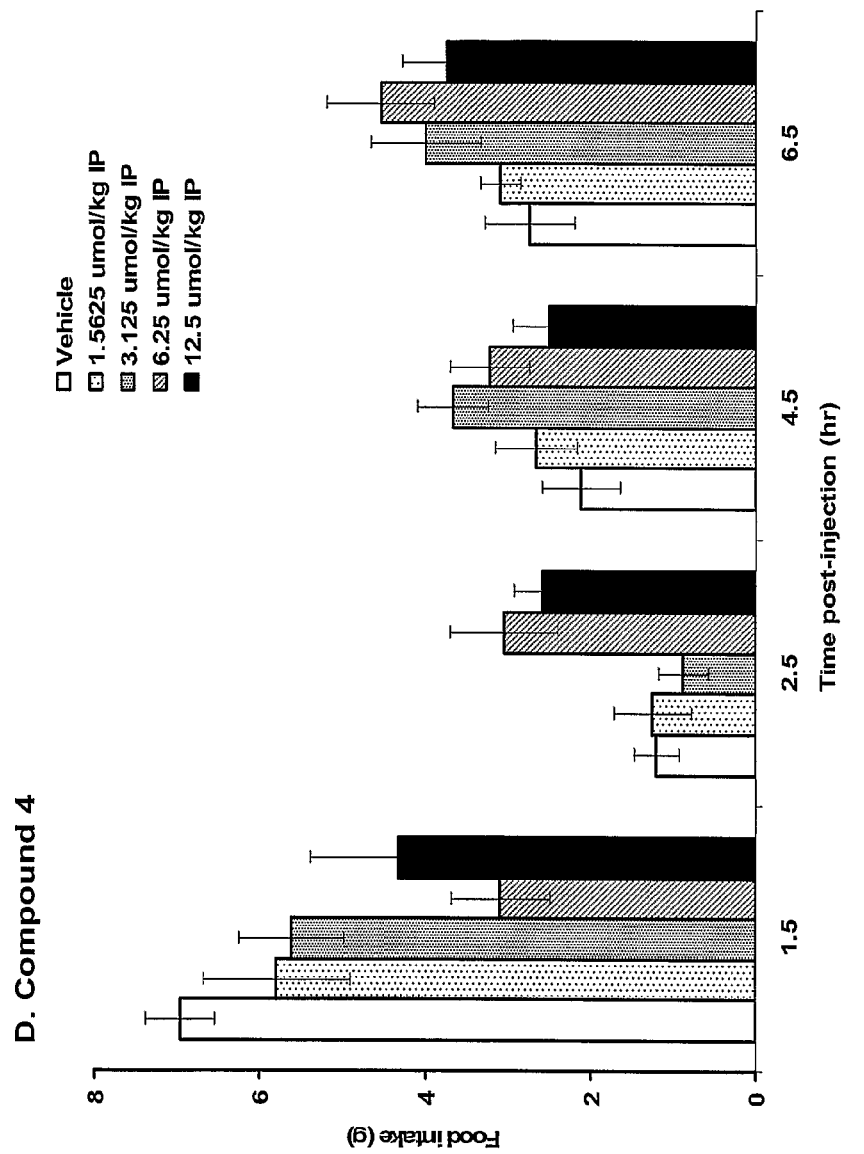
Figure 1E:
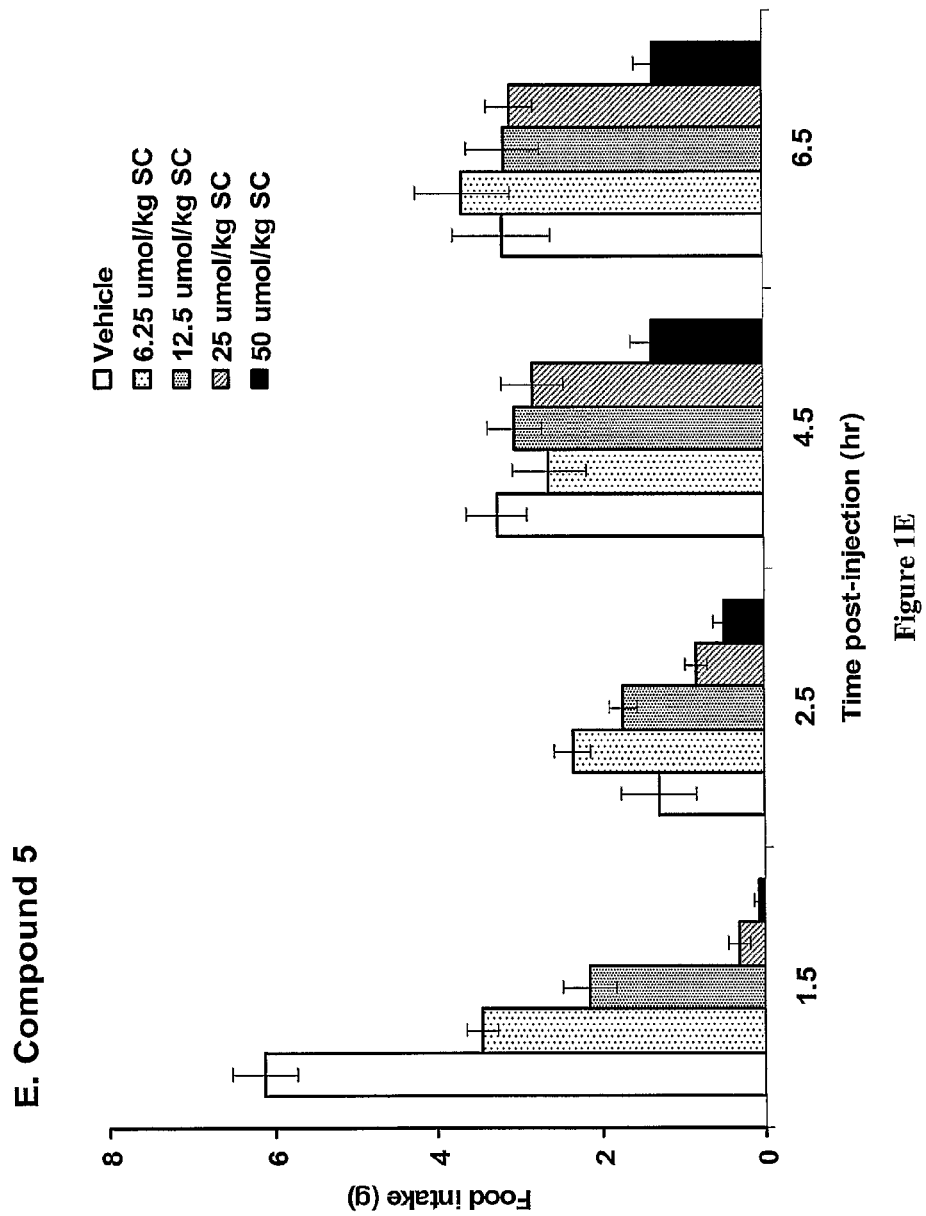
Figure 1F:
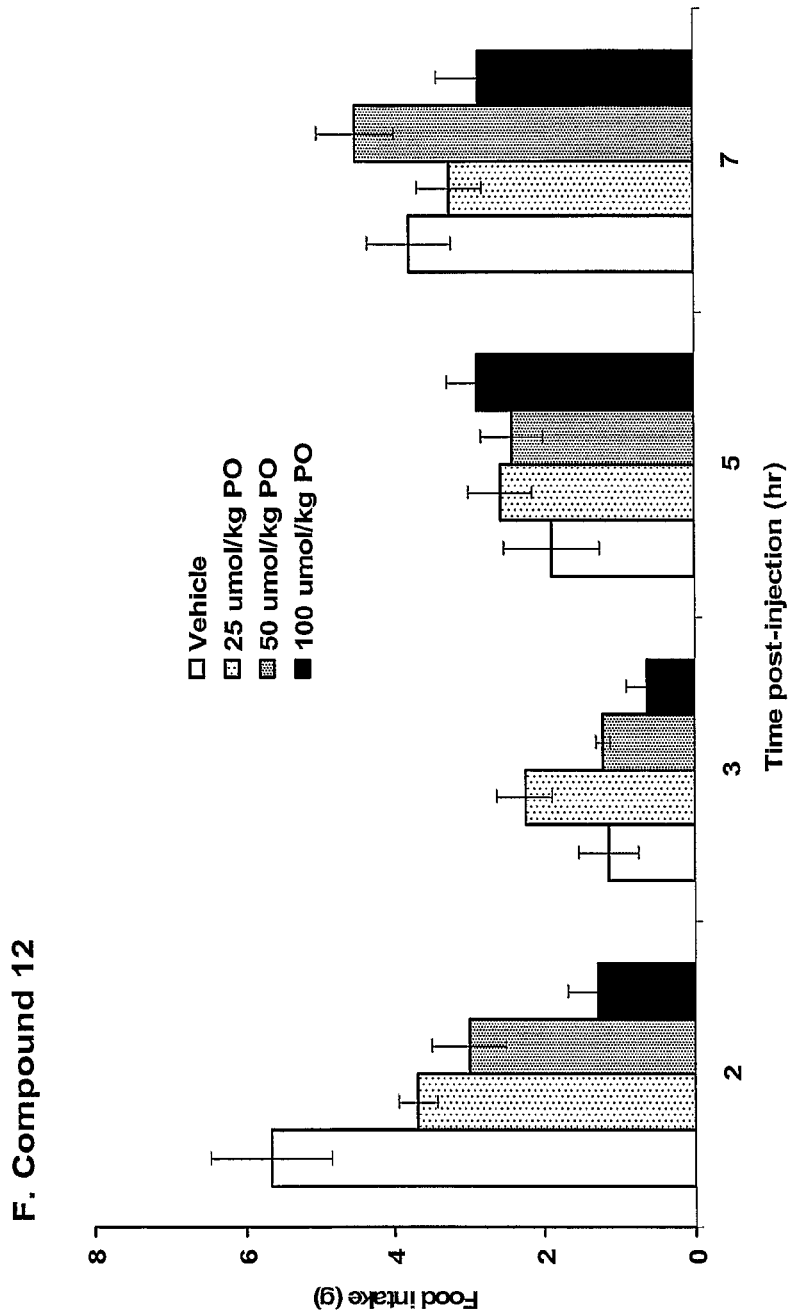
Figure 1G:
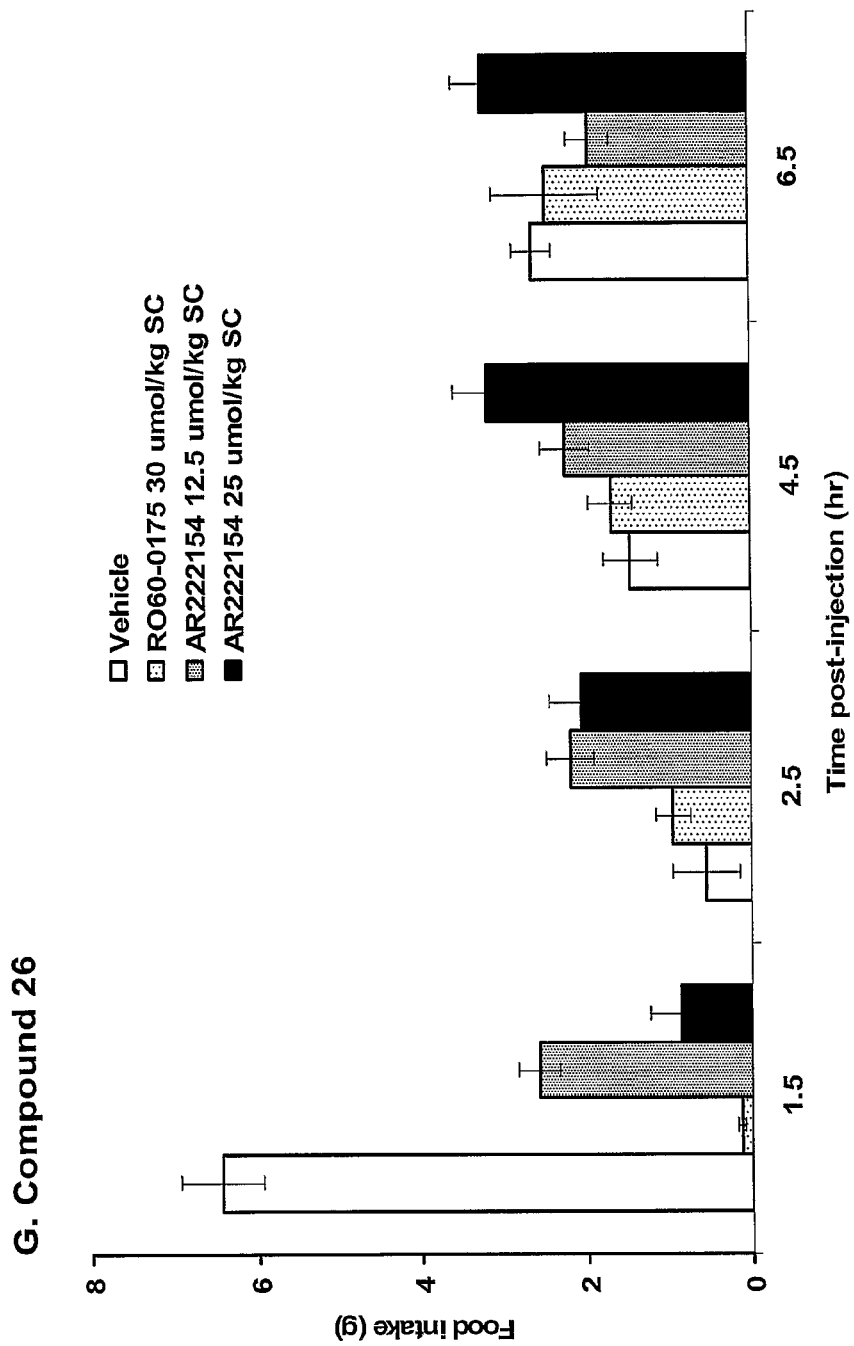

The present invention relates to the combination of 5HT-2C receptor agonist compounds with other agents in order to decrease certain 5HT-2C receptor related behaviors such as feeding. While the 5HT-2C receptor agonist compounds described in the invention can be employed as the sole active agent in a pharmaceutical (i.e., mono-therapy), they can advantageously be used in combination with other active ingredients (i.e., combination-therapy) which can facilitate the therapeutic effect of the compound. Therefore, one aspect of the present invention includes methods of prophylaxis and/or treatment of a 5HT-2C receptor related condition such as obesity, or a condition related thereto, comprising administering to an individual in need of said prophylaxis and/or treatment a combination comprising an amount of a selective 5HT-2C receptor agonist in combination with an amount of one or more additional pharmaceutical agent as described herein. In one embodiment, the amount of the selective 5HT-2C receptor agonist and the amount of the one or more additional pharmaceutical agents alone are therapeutically sub-effective in the prophylaxis and/or treatment of the condition but when combined these compounds act synergistically to prevent or treat the condition.

Suitable pharmaceutical agents that can be used in combination with the selective 5HT-2C receptor agonists include, for example, anti-obesity agents such as apolipoprotein-B secretion/microsomal triglyceride transfer protein (apo-B/MTP) inhibitors, MCR-4 agonists, cholescystokinin-A (CCK-A) agonists, serotonin and norepinephrine reuptake inhibitors (for example, sibutramine), sympathomimetic agensts, $\beta_3$ adrenergic receptor agonists, dopamine agonists (for example, bromocriptine), melanocyte-stimulating hormone receptor analogs, cannabinoid 1 receptor antagonists [for example, SR141716: N-(piperidin-1-yl)-5-(4-chlorophenyl)-1-(2,4-dichlorophenyl)-4-methyl-1H-pyrazole-3-carboxamide], melanin concentrating hormone antagonists, leptins (the OB protein), leptin analogues, leptin receptor agonists, galanin antagonists, lipase inhibitors (such as tetrahydrolipstatin, i.e., Orlistat), anorectic agents (such as a bombesin agonist), Neuropeptide-Y antagonists, thyromimetic agents, dehydroepiandrosterone or an analogue thereof, glucocorticoid receptor agonists or antagonists, orexin receptor antagonists, urocortin binding protein antagonists, glucagon-like peptide-1 receptor agonists, ciliary neutrotrophic factors (such as Axokine™ available from Regeneron Pharmaceuticals, Inc., Tarrytown, N.Y. and Procter & Gamble Company, Cincinnati, Ohio), human agouti-related proteins (AGRP), ghrelin receptor antagonists, histamine 3 receptor antagonists or reverse agonists, neuromedin U receptor agonists, noradrenergic anorectic agents (for example, phentermine, mazindol and the like) and appetite suppressants (for example, bupropion).

Other anti-obesity agents, including the agents set forth infra, are well known, or will be readily apparent in light of the instant disclosure, to one of ordinary skill in the art.

In some embodiments, the anti-obesity agents are selected from the group consisting of phentermine, orlistat, sibutramine, bromocriptine, ephedrine, leptin, and pseudoephedrine. In one embodiment, the anti-obesity agent is phentermine. In a further embodiment, compositions of the present invention and combination therapies are administered in conjunction with exercise and/or a sensible diet.

It will be understood that the scope of combination therapy of the compounds of the present invention with other anti-obesity agents, anorectic agents, appetite suppressant and related agents is not limited to those listed above, but includes in principle any combination with any pharmaceutical agent or pharmaceutical composition useful for the treatment of overweight and obese individuals.

Other suitable pharmaceutical agents, in addition to anti-obesity agents, that can be used in combination with the compounds of the present invention include agents useful in the treatment of concomitant diseases. For example, individuals who are overweight or obese increase their risk of morbidity and mortality arising from concomitant diseases, such as, but not limited to, congestive heart failure, type II diabetes, atherosclerosis, dyslipidemia, hyperinsulinemia, hypertension, insulin resistance, hyperglycemia, retinopathy, nephropathy and neuropathy. Treatment for one or more of the diseases cited herein include the use of one or more pharmaceutical agents known in the art belonging to the classes of drugs referred to, but not limited to, the following: sulfonylureas, meglitinides, biguanides, α-glucosidase inhibitors, peroxisome proliferators-activated receptor-γ (i.e., PPAR-γ) agonists, insulin, insulin analogues, HMG-CoA reductase inhibitors, cholesterol-lowering drugs (for example, fibrates that include: fenofibrate, bezafibrate, gemfibrozil, clofibrate and the like; bile acid sequestrants which include: cholestyramine, colestipol and the like; statins, and niacin), antiplatelet agents (for example, aspirin and adenosine diphosphate receptor antagonists that include: clopidogrel, ticlopidine and the like), angiotensin-converting enzyme inhibitors, angiotensin II receptor antagonists and adiponectin.

It will be understood that the scope of combination therapy of the compounds of the present invention with other pharmaceutical agents is not limited to those listed herein, supra or infra, but includes in principle any combination with any pharmaceutical agent or pharmaceutical composition useful for the treatment diseases, conditions or disorders that are linked to overweight and obese individuals.

Combination therapies have been used in the treatment of diseases; however, care must be taken when combining drugs since certain drugs can interact in a harmful manner. The combination of two agents that treat the same condition is generally expected to result in an additive effect meaning that the degree of the effect is the sum of the effect of each drug alone. Applicants disclose herein that the combination of a selective 5HT-2C agonist and another drug such as phentermine can result in a supra additive or synergistic effect on food intake (see FIGS. 2, 3A and B, 4A and B). A synergistic effect means that the decrease in food intake observed with the combination therapy is greater than that seen by adding the decrease in food intake of each compound together. One advantage of using a synergistic combination therapy is that less of each compound is required to achieve a significant decrease in food intake and so fewer side effects can result from treatment. In some cases, side effects are not seen at the lower doses used. Also, in some cases, the side effect profile of one drug can mitigate or average out the side effect profile of the other drug. For example, one of the drugs may result in increased blood pressure and the other drug results in lowered blood pressure so that the combination therapy does not effect blood pressure. Another potential advantage of combination therapy is that, since less compound is required, the cost of therapy can be reduced.

This application incorporates by reference, in their entirety, U.S. Provisional Application No. 60/372,058, filed Apr. 12, 2002; U.S. Provisional Patent Application No. 60/405,495, filed Aug. 23, 2002; U.S. Provisional Patent Application No. 60/434,607, filed Dec. 18, 2002; U.S. Non-Provisional patent application Ser. No. 10/410,991, filed Apr. 10, 2003 and U.S. NonProvisional patent application Ser. No.

10/917,979, filed Aug. 13, 2004. This application claims priority to, and incorporates by reference in their entirety, U.S. Non-Provisional application Ser. No. 11/793,941 filed Apr. 11, 2008, U.S. Provisional Application No. 60/638,667, filed Dec. 23, 2004, and U.S. Provisional Application No. 60/688,901, filed Jun. 8, 2005.

In one aspect, the invention provides a composition comprising phentermine and a selective 5HT-2C receptor agonist.

Phentermine (1,1-Dimethyl-2-phenyl-ethylamine) includes phentermine derivatives or pharmaceutically acceptable salts thereof, such as, but not limited to, chlorphentermine (2-(4-Chloro-phenyl)-1,1-dimethyl-ethylamine) and the like. In one embodiment, phentermine is in the HCl salt form.

As used herein, the term "agonist" is intended to mean moieties that activate the intracellular response when they bind to the receptor, or enhance GTP binding to membranes. In the context of the present invention, a pharmaceutical composition comprising a $5HT_{2C}$ receptor agonist of the invention can be utilized for modulating the activity of the $5HT_{2C}$ receptor, decreasing food intake, inducing satiation (i.e., the feeling of fullness), controlling weight gain, treating obesity, decreasing body weight and/or affecting metabolism such that the recipient loses weight and/or maintains weight. Such pharmaceutical compositions can be used in the context of disorders and/or diseases where weight gain is a component of the disease and/or disorder such as, for example, obesity.

The term "antagonist" is intended to mean moieties that competitively bind to the receptor at the same site as agonists (for example, the endogenous ligand), but which do not activate the intracellular response initiated by the active form of the receptor, and can thereby inhibit the intracellular responses by agonists or partial agonists. Antagonists do not diminish the baseline intracellular response in the absence of an agonist or partial agonist.

As used herein the term "selective 5HT-2C receptor agonist" means an agonist compound that is selective for 5HT-2C receptor compared to other receptors that decrease food intake. For example, a selective 5HT-2C receptor agonist has a significantly higher binding affinity for the 5HT-2C receptor than for another receptor that can decrease food intake such as the 5HT-1b receptor. Therefore, for example, a selective 5HT-2C receptor agonist can have 10-fold, 20-fold, 30-fold, 40-fold, 50-fold, 60-fold, 70-fold, 80-fold, 90-fold, 100-fold, or 150-fold or more higher binding affinity for the 5HT-2C receptor than for another receptor such as the 5HT-1b receptor. As understood by one skilled in the art, selectivity can be determined, for example, using a receptor binding assay or a functional assay. One way to assess selectivity is to perform a feeding assay as disclosed herein (see Example 2) with a potential selective 5HT-2C receptor agonist and then challenge the animals with a selective 5HT-2C antagonist, for example, SB 242084 (Sigma). If the food intake effect is abolished (or very significantly decreased) then the effect is deemed to be occurring through the 5HT-2C receptor and not through a different receptor.

The term "selective 5HT-2C receptor agonist" does not include compounds such as dexfenfluramine which are 5HT-releasing agents or compounds such as fluoxetine which are 5HT uptake inhibitors. In addition, the term "selective 5HT-2C receptor agonist" does not include non-selective 5HT agonists such as m-chlorophenylpiperazine (mCPP) or m-trifluoromethylphenylpiperazine (TFMPP) which have significant effects at the 5HT-1b receptor. For example, TFMPP causes decreased food intake; however, the decrease in food intake is not abolished when a selective 5HT-2C antagonist such as SB 242084 is added.

As disclosed herein, compositions of the invention can comprise phentermine and a selective 5HT-2C receptor agonist. The phentermine and selective 5HT-2C receptor agonist can be delivered as separate entities or the phentermine and selective 5HT-2C receptor agonist can be combined to form one entity. For example, phentermine and selective 5HT-2C receptor agonist can be delivered as two separate pills or capsules or they can be combined to form one pill or capsule.

The invention also provides a composition comprising phentermine and a selective 5HT-2C receptor agonist where the selective 5HT-2C receptor agonist has Formula (I):

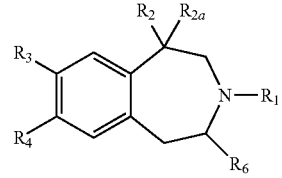

(I)

or a pharmaceutically acceptable salt, solvate or hydrate thereof.

wherein:
$R_1$ is H or $C_{1-8}$ alkyl;
$R_2$ is $C_{1-8}$ alkyl, —$CH_2$—O—$C_{1-8}$ alkyl, —C(=O)—O—$C_{1-8}$ alkyl, —C(=O)—NH—$C_{1-8}$ alkyl, OH, or $CH_2OH$;
$R_{2a}$ is H;
or $R_2$ and $R_{2a}$ together form —$CH_2$—$CH_2$—;
$R_3$ and $R_4$ are each independently H, halogen, perhaloalkyl, CN, $OR_5$, $SR_5$, $NHR_5$, $N(R_5)_2$, OH, aryl, or heteroaryl, wherein said aryl can be optionally substituted with up to two substituents selected from $C_{1-8}$ alkyl, halogen, perhalo alkyl, and alkoxy, and said heteroaryl can be optionally substituted with up to two substituents selected from halogen and $C_{1-8}$ alkyl;
or $R_3$ and $R_4$ together with the atoms to which they are attached can form a 5- or 6-member heterocyclic ring having one O atom;
each $R_5$ is independently $C_{1-8}$ alkyl, $C_{1-8}$ alkenyl, aryl, heteroaryl, arylalkyl, heteroarylalkyl or perhaloalkyl, or allyl; and
$R_6$ is H or $C_{1-8}$ alkyl.

Some embodiments of the present invention pertain to a composition comprising phentermine and a selective 5HT-2C receptor agonist where the selective 5HT-2C receptor agonist has Formula (I):

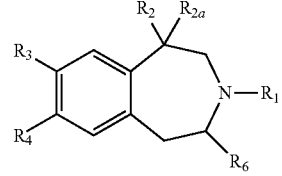

(I)

or a pharmaceutically acceptable salt, solvate or hydrate thereof.

wherein:
$R_1$ is H or $C_{1-8}$ alkyl;
$R_2$ is $C_{1-8}$ alkyl, —$CH_2$—O—$C_{1-8}$ alkyl, —C(=O)—O—$C_{1-8}$ alkyl, —C(=O)—NH—$C_{1-8}$ alkyl, OH, or $CH_2OH$;
$R_{2a}$ is H;
or $R_2$ and $R_{2a}$ together form —$CH_2$—$CH_2$—;
$R_3$ is halogen, perhaloalkyl, CN, $SR_5$, $NHR_5$, $N(R_5)_2$, aryl, or heteroaryl, wherein said aryl can be optionally substituted with up to two substituents selected from $C_{1-8}$ alkyl, halogen, perhalo alkyl, and alkoxy, and said heteroaryl can be optionally substituted with up to two substituents selected from halogen and $C_{1-8}$ alkyl;

$R_4$ is H, halogen, perhaloalkyl, CN, $SR_5$, $NHR_5$, $N(R_5)_2$, aryl, or heteroaryl, wherein said aryl can be optionally substituted with up to two substituents selected from $C_{1-8}$ alkyl, halogen, perhalo alkyl, and alkoxy, and said heteroaryl can be optionally substituted with up to two substituents selected from halogen and $C_{1-8}$ alkyl;

each $R_5$ is independently $C_{1-8}$ alkyl, $C_{1-8}$ alkenyl, aryl, heteroaryl, arylalkyl, heteroarylalkyl or perhaloalkyl, or allyl; and $R_6$ is H or $C_{1-8}$ alkyl;

wherein heteroaryl is pyrrolyl, pyrazolyl, imidazolyl, triazolyl, tetrazolyl, pyridyl, pyrimidinyl, furanyl, pyranyl, thienyl, benzimidazolyl, quinolinyl, isoquinolinyl, oxazolyl, thiazolyl or thiadiazolyl;

or a pharmaceutically acceptable salt, solvate or hydrate thereof provided that:

(i) if $R_6$ is other than H, then neither $R_3$ nor $R_4$ can be H;
(ii) if $R_1$ and $R_2$ are methyl, and $R_4$ is H, then $R_3$ cannot be $NHR_5$ or $N(R_5)_2$; and
(iii) if $R_1$ and $R_2$ are methyl, and $R_4$ is H, then $R_3$ cannot be imidazole, substituted imidazole, or an imidazole derivative.

Some embodiments of the present invention pertain to a composition comprising phentermine and a selective 5HT-2C receptor agonist where the selective 5HT-2C receptor agonist has Formula (I):

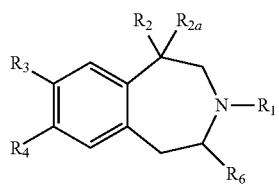

(I)

wherein:

$R_1$ is: —H or $C_{1-8}$alkyl;
$R_2$ is: $C_{1-8}$alkyl, —C(=O)—NH—$C_{1-8}$alkyl, —OH, or —CH$_2$OH;
$R_{2a}$ is: —H;
or $R_2$ and $R_{2a}$ together form —CH$_2$—CH$_2$—;
$R_3$ is: halogen; perhaloalkyl; or a 5-membered heteroaryl ring having up to two heteroatoms selected from O, N and S;
$R_4$ is —H, halogen, perhaloalkyl, —CN, —OR$_5$, —SR$_5$, —NHR$_5$, —N(R$_5$)$_2$, —OH, aryl, or heteroaryl, wherein said aryl can be optionally substituted with up to two substituents selected from $C_{1-8}$alkyl, halogen, perhaloalkyl, and alkoxy, and said heteroaryl can be optionally substituted with up to two substituents selected from halogen and $C_{1-8}$alkyl;
or:
$R_3$ and $R_4$ together with the atoms to which they are attached form a 5- or 6-member heterocyclic ring having one O atom;
each $R_5$ is independently $C_{1-8}$alkyl, $C_{1-8}$alkenyl, aryl, heteroaryl, arylalkyl, heteroarylalkyl or perhaloalkyl, or allyl; and
$R_6$ is —H or $C_{1-8}$alkyl;
or a pharmaceutically acceptable salt, solvate or hydrate thereof;
provided that:
if $R_6$ is other than —H, then $R_4$ cannot be —H; and
if $R_1$ and $R_2$ are methyl, and $R_4$ is —H, then $R_3$ cannot be imidazole, substituted imidazole, or an imidazole derivative;
and wherein:
aryl denotes a monocyclic or polycyclic aromatic group having from 3 to 14 carbon atoms;
heteroaryl denotes a monocyclic or polycyclic aromatic group having from 3 to 14 carbon atoms, and from 1 to 4 ring heteroatoms selected from O, N, and S;
alkoxy denotes —O-alkyl;
$C_{1-8}$alkyl denotes a straight chain, branched, or cyclic hydrocarbon group having from 1 to 8 carbon atoms;
$C_{1-8}$alkenyl denotes a straight chain, branched, or cyclic hydrocarbon group having from 1 to 8 carbon atoms and at least one double bond;
alkyl, other than $C_{1-8}$alkyl, denotes methyl, ethyl, n-propyl, isopropyl, cyclopropyl, n-butyl, sec-butyl, tert-butyl, cyclobutyl, cylopropylmethyl, n-pentyl, isopentyl, tert-pentyl, cyclopentyl, cyclotpentylmethyl, n-hexyl, or cyclohexyl.

It is appreciated that compounds of Formula (I) can have one or more chiral centers, and exist as enantiomers or diastereomers. The invention is to be understood to extend to all such enantiomers, diastereomers and mixtures thereof, including racemates. Formula (I) and the formulae hereinafter are intended to represent all individual isomers and mixtures thereof, unless stated or shown otherwise.

It is also appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables (e.g. $R_1$, $R_2$, $R_{2a}$, $R_3$, $R_4$, $R_5$, $R_6$, etc.) contained within the generic chemical formulae described herein [e.g. Formula (I) etc.] are specifically embraced by the present invention just as if they were explicitly disclosed, to the extent that such combinations embrace compounds that result in stable compounds (i.e., compounds that can be isolated, characterized and tested for biological activity). In addition, all subcombinations of the chemical groups listed in the embodiments describing such variables, as well as all subcombinations of uses and medical indications described herein, are also specifically embraced by the present invention just as if each of such subcombination of chemical groups and subcomination of uses and medical indications were explicitly disclosed herein.

As used herein, "substituted" indicates that at least one hydrogen atom of the chemical group is replaced by a non-hydrogen substituent or group, the non-hydrogen substituent or group can be monovalent or divalent. When the substituent or group is divalent, then it is understood that this group is further substituted with another substituent or group. When a chemical group herein is "substituted" it may have up to the full valance of substitution; for example, a methyl group can be substituted by 1, 2, or 3 substituents, a methylene group can be substituted by 1 or 2 substituents, a phenyl group can be substituted by 1, 2, 3, 4, or 5 substituents, a naphthyl group can be substituted by 1, 2, 3, 4, 5, 6, or 7 substituents and the like. Likewise, "substituted with one or more substituents" refers to the substitution of a group with one substituent up to the total number of substituents physically allowed by the group. Further, when a group is substituted with more than one group they can be identical or they can be different.

As used herein, the term "alkyl" is intended to denote hydrocarbon groups including straight chain, branched and cyclic hydrocarbons, including for example but not limited to methyl, ethyl, n-propyl, isopropyl, cyclopropyl, n-butyl, sec-butyl, tert-butyl, cyclobutyl, cyclopropylmethyl, n-pentyl, isopentyl, tert-pentyl, cyclopentyl, cyclopentylmethyl, n-hexyl, cyclohexyl, and the like. Throughout this specification, it should be understood that the term alkyl is intended to encompass both non-cyclic hydrocarbon groups and cyclic hydrocarbon groups. In some embodiments of the compounds of the invention, alkyl groups are non-cyclic. In further embodiments, alkyl groups are cyclic, and in further embodiments, alkyl groups are both cyclic and noncyclic. Where no preference is specified, the term "alkyl" is intended to denote groups that are both cyclic and non-cyclic.

As used herein, the term "alkenyl" is intended to denote hydrocarbon compounds including straight chain, branched and cyclic hydrocarbons that contain at least one double bond, including for example but not limited to allyl, 2-methyl-allyl, 4-but-3-enyl, 4-hex-5-enyl, 3-methyl-but-2-enyl, cyclohex-2-enyl and the like.

As used herein, the term "halogen" has its normal meaning of period seven elements, including F, Cl, Br and I.

The term "alkoxy" is intended to denote substituents of the formula —O-alkyl, including —O-allyl. The term "lower" when used in connection with substituents such as alkyl indicates 6 carbons or less.

The term "arylalkyl" or "aralkyl" is intended to denote an alkyl group that bears an aryl substituent, for example a benzyl group. The term "alkylaryl" or "alkaryl" is intended to denote an aryl group that bears an alkyl substituent, for example a 4-methylphenyl group.

As used herein, the term "aryl" is intended to mean monocyclic and polycyclic aromatic groups. Although aryl groups can include as few as 3 carbon atoms, preferred aryl groups have 6 to about 14 carbon atoms, more preferably 6 to about 10 carbon atoms. Examples of aryl groups include but are not limited to phenyl, naphthyl, anthracyl, phenanthryl and pyrenyl.

The term "heteroaryl" is intended to denote an aryl group that contains at least one, and preferably from one to four ring "hetero" (i.e., non-carbon, e.g., O, N or S) atom. Examples of "heteroaryl" groups are radicals derived from 5- and 6-member aryl ring compounds having from one to four nitrogen, sulfur and/or oxygen atoms, for example pyrrole, pyrazole, imidazole, triazole, tetrazole, pyridine, pyrimidine, furan, pyran, thiophene, benzimidazole, quinoline, isoquinoline, oxazole, thiazole, and thiadiazole.

As used herein the term heteroarylalkyl means an alkyl group that bears a heteroaryl substituent, for example a group having the structure —CH$_2$-pyrrole-2-yl.

The term "substituted thiazole" means a radical derived from thiazole that bears at least one substituent group. The term "thiazole derivative" means a fused ring system in which one of the fused rings is thiazole.

The term "substituted imidazole" means a radical derived from imidazole that bears at least one substituent group. The term "imidazole derivative" means a fused ring system in which one of the fused rings is imidazole.

Certain substituents of the compounds disclosed herein can optionally be substituted, i.e., they can optionally bear further substituent groups. Some preferred substituent groups include halogen, lower alkyl (including but not limited to methyl, ethyl, isopropyl, cyclopropyl, tert-butyl, and methylcyclopropyl), alkoxy, mono-, di- or trihaloalkoxy (e.g., —O—CX$_3$ where X is halogen), —(CH$_2$)$_y$NH$_2$, —(CH$_2$)$_y$N-HBoc, —N(R$_{4a}$)(R$_{4b}$), phenyl, methoxyphenyl and naphthyl.

At various places in the present specification substituents of compounds of the invention are disclosed in groups or in ranges. It is specifically intended that the invention include each and every individual subcombination of the members of such groups and ranges. For example, the term "C$_{1-8}$ alkyl" is specifically intended to individually disclose methyl, ethyl, C$_3$ alkyl, C$_4$ alkyl, C$_5$ alkyl, C$_6$ alkyl, C$_7$ alkyl and C$_8$ alkyl.

Additionally, compounds of the present invention encompass all pharmaceutically acceptable salts, solvates, and particularly hydrates, thereof; including but not limited to, phentermine, phentermine derivatives (e.g., chlorphentermine), selective 5HT-2C receptor agonists (e.g., compounds of Formula (I)), and the like.

In some embodiments of the present invention, the selective 5HT-2C receptor agonist is of Formula (I): wherein:
  R$_3$ is halogen, perhaloalkyl, CN, SR$_5$, NHR$_5$, N(R$_5$)$_2$, aryl, or heteroaryl, wherein said aryl can be optionally substituted with up to two substituents selected from C$_{1-8}$ alkyl, halogen, perhalo alkyl, and alkoxy, and said heteroaryl can be optionally substituted with up to two substituents selected from halogen and C$_{1-8}$ alkyl; and
  R$_4$ is H, halogen, perhaloalkyl, CN, SR$_5$, NHR$_5$, N(R$_5$)$_2$, aryl, or heteroaryl, wherein said aryl can be optionally substituted with up to two substituents selected from C$_{1-8}$ alkyl, halogen, perhalo alkyl, and alkoxy, and said heteroaryl can be optionally substituted with up to two substituents selected from halogen and C$_{1-8}$ alkyl;
  wherein heteroaryl is pyrrolyl, pyrazolyl, imidazolyl, triazolyl, tetrazolyl, pyridyl, pyrimidinyl, furanyl, pyranyl, thienyl, benzimidazolyl, quinolinyl, isoquinolinyl, oxazolyl, thiazolyl or thiadiazolyl.

In some embodiments of the present invention, the selective 5HT-2C receptor agonist is of Formula (I) wherein R$_1$ is H.

In some embodiments of the present invention, the selective 5HT-2C receptor agonist is of Formula (I) wherein R$_1$ is methyl.

In some embodiments of the present invention, the selective 5HT-2C receptor agonist is of Formula (I) wherein R$_2$ is methyl, ethyl, n-propyl or isopropyl.

In some embodiments of the present invention, the selective 5HT-2C receptor agonist is of Formula (I) wherein R$_2$ is methyl or ethyl.

In some embodiments of the present invention, the selective 5HT-2C receptor agonist is of Formula (I) wherein R$_2$ and R$_{2a}$ together form —CH$_2$CH$_2$—.

In some embodiments of the present invention, the selective 5HT-2C receptor agonist is of Formula (I) wherein R$_3$ is chlorine.

In some embodiments of the present invention, the selective 5HT-2C receptor agonist is of Formula (I) wherein R$_3$ is bromine.

In some embodiments of the present invention, the selective 5HT-2C receptor agonist is of Formula (I) wherein R$_3$ is perhaloalkyl. In some embodiments, R$_3$ is CF$_3$.

In some embodiments of the present invention, the selective 5HT-2C receptor agonist is of Formula (I) wherein R$_3$ is selected from the group consisting of thienyl, furanyl, pyrrolyl, pyrazolyl and imidazolyl.

In some embodiments of the present invention, the selective 5HT-2C receptor agonist is of Formula (I) wherein R$_4$ is selected from the group consisting of thienyl, furanyl, pyrrolyl, pyrazolyl and imidazolyl optionally substituted with one or two substituents selected from halogen or methyl or wherein R$_4$ is phenyl optionally substituted with up to two substituents selected from C$_{1-8}$ alkyl, halogen, and alkoxy.

In some embodiments of the present invention, the selective 5HT-2C receptor agonist is of Formula (I) wherein: R$_2$ is methyl, ethyl, isopropyl, or CH$_2$OH; or R$_2$ and R$_{2a}$ taken together form —CH$_2$CH$_2$—.

In some embodiments of the present invention, the selective 5HT-2C receptor agonist is of Formula (I) wherein: R$_3$ is halogen, or a 5-membered heteroaryl ring having up to two heteroatoms selected from O, N and S, and up to two substituents selected from halogen and $C_{1-8}$ alkyl.

In some embodiments of the present invention, the selective 5HT-2C receptor agonist is of Formula (I) wherein: $R_4$ is H, a 5-membered heteroaryl ring having up to two heteroatoms selected from O, N and S and up to two substituents selected from halogen and $C_{1-8}$ alkyl, or phenyl optionally substituted with up to two substituents selected from $C_{1-8}$ alkyl, halogen, and alkoxy.

In some embodiments of the present invention, the selective 5HT-2C receptor agonist is of Formula (I) wherein: $R_6$ is H or methyl.

In some embodiments of the present invention, the selective 5HT-2C receptor agonist is of Formula (I) wherein: $R_1$ is H.

In some embodiments of the present invention, the selective 5HT-2C receptor agonist is of Formula (I) wherein: $R_2$ is methyl.

In some embodiments of the present invention, the selective 5HT-2C receptor agonist is of Formula (I) wherein: $R_3$ is chlorine, bromine, or thienyl.

In some embodiments of the present invention, the selective 5HT-2C receptor agonist is of Formula (I) wherein: $R_4$ is pyrazolyl-3-yl or phenyl wherein said pyrazolyl-3-yl optionally has up to two substituents selected from halogen and $C_{1-8}$ alkyl, and said phenyl optionally has a single halogen substitutent.

In some embodiments of the present invention, the selective 5HT-2C receptor agonist is of Formula (I) wherein: $R_6$ is H.

In some embodiments of the present invention, the selective 5HT-2C receptor agonist is of Formula (I) wherein: $R_1$ is H or Me.

In some embodiments of the present invention, the selective 5HT-2C receptor agonist is of Formula (I) wherein: $R_2$ is Me, Et, or OH.

In some embodiments of the present invention, the selective 5HT-2C receptor agonist is of Formula (I) wherein: $R_{2a}$ is H.

In some embodiments of the present invention, the selective 5HT-2C receptor agonist is of Formula (I) wherein: $R_3$ is F, Cl, Br, I, $CF_3$, or 2-chlorophenyl.

In some embodiments of the present invention, the selective 5HT-2C receptor agonist is of Formula (I) wherein: $R_4$ is H.

In some embodiments of the present invention, the selective 5HT-2C receptor agonist is of Formula (I) wherein: $R_6$ is H.

In some embodiments of the present invention, the selective 5HT-2C receptor agonist is of Formula (I) wherein: $R_1$ is H.

In some embodiments of the present invention, the selective 5HT-2C receptor agonist is of Formula (I) wherein: $R_2$ is $C_{1-8}$ alkyl.

In some embodiments of the present invention, the selective 5HT-2C receptor agonist is of Formula (I) wherein: $R_{2a}$ is H.

In some embodiments of the present invention, the selective 5HT-2C receptor agonist is of Formula (I) wherein: $R_3$ is halogen.

In some embodiments of the present invention, the selective 5HT-2C receptor agonist is of Formula (I) wherein: $R_4$ is H.

In some embodiments of the present invention, the selective 5HT-2C receptor agonist is of Formula (I) wherein: $R_6$ is H.

The invention provides a composition comprising phentermine and a selective 5HT-2C receptor agonist as described herein wherein said selective 5HT-2C receptor agonist is selected from the group consisting of:
8-chloro-1-methyl-2,3,4,5-tetrahydro-1H-3-benzazepine;
8-bromo-1-methyl-2,3,4,5-tetrahydro-1H-3-benzazepine;
8-iodo-1-methyl-2,3,4,5-tetrahydro-1H-3-benzazepine;
8-trifluoromethyl-1-methyl-2,3,4,5-tetrahydro-1H-3-benzazepine;
8-trifluoromethyl-1-ethyl-2,3,4,5-tetrahydro-1H-3-benzazepine;
8-chloro-1-ethyl-2,3,4,5-tetrahydro-1H-3-benzazepine;
8-bromo-1-ethyl-2,3,4,5-tetrahydro-1H-3-benzazepine;
8-iodo-1-ethyl-2,3,4,5-tetrahydro-1H-3-benzazepine;
7,8-dichloro-1-methyl-2,3,4,5-tetrahydro-1H-3-benzazepine;
7,8-dichloro-1-ethyl-2,3,4,5-tetrahydro-1H-3-benzazepine;
8-chloro-7-fluoro-1-methyl-2,3,4,5-tetrahydro-1H-3-benzazepine;
8-chloro-7-methoxy-1-methyl-2,3,4,5-tetrahydro-1H-3-benzazepine; and
8-chloro-7-fluoro-1-ethyl-2,3,4,5-tetrahydro-1H-3-benzazepine;
    or a pharmaceutically acceptable salt, solvate or hydrate thereof.

The compounds of the invention may contain one or more asymmetric carbon atoms, so that the compounds can exist in different stereoisomeric forms. The compounds can be, for example, racemates or optically active forms. The optically active forms can be obtained by resolution of the racemates or by asymmetric synthesis. In some embodiments, compounds of Formula (I) are R enantiomers. In some embodiments, compounds of Formula (I) are S enantiomers. In some embodiments, compounds of Formula (I) are varying mixtures of enantiomers.

In one embodiment, the invention provides a composition comprising phentermine and a selective 5HT-2C receptor agonist wherein said selective 5HT-2C receptor agonist is (R)-8-chloro-1-methyl-2,3,4,5-tetrahydro-1H-3-benzazepine or a pharmaceutically acceptable salt, solvate or hydrate thereof.

The compounds and compositions according to the invention may optionally exist as pharmaceutically acceptable salts including pharmaceutically acceptable acid addition salts prepared from pharmaceutically acceptable non-toxic acids including inorganic and organic acids. Such acids include acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like, such as the pharmaceutically acceptable salts listed in Journal of Pharmaceutical Science, 66, 2 (1977) and incorporated herein by reference.

The acid addition salts can be obtained as the direct products of compound synthesis. In the alternative, the free base can be dissolved in a suitable solvent containing the appropriate acid, and the salt isolated by evaporating the solvent or otherwise separating the salt and solvent. The compounds of this invention may form solvates with standard low molecular weight solvents using methods known to the skilled artisan.

Compositions of the invention may conveniently be administered in unit dosage form and can be prepared by any of the methods well known in the pharmaceutical art, for example, as described in *Remington's Pharmaceutical Sciences* (Mack Pub. Co., Easton, Pa., 1980).

The invention also provides compositions of the invention, as described above, further comprising a pharmaceutically acceptable carrier. For example, the invention provides a composition comprising phentermine and (R)-8-chloro-1-methyl-2,3,4,5-tetrahydro-1H-3-benzazepine, or a pharmaceutically acceptable salt, solvate or hydrate thereof, and a pharmaceutically acceptable carrier. Thus, the invention provides pharmaceutical compositions containing phentermine and a selective 5HT-2C agonist. A pharmaceutical composition is a composition comprising at least one active ingredient and at least one ingredient that is not an active ingredient (for example and not limitation, a filler, dye, or a mechanism for slow release), whereby the composition is amenable to use for a specified, efficacious outcome in a mammal (for example, and not limitation, a human).

According to a further aspect of the invention, the compositions of the invention are provided for use in therapy. The compositions can be used in the prophylaxis or treatment of disorders associated with 5-$HT_{2C}$ receptor function.

According to a further aspect of the invention, there is provided use of a composition of the invention in the manufacture of a medicament for the prophylaxis or treatment of the disorders disclosed herein. In a preferred embodiment, there is provided a use of a composition of the invention in the manufacture of a medicament for the prophylaxis or treatment of obesity.

The data developed herein supports the conclusion that the presently disclosed compositions of the invention are of use for the treatment or prophylaxis of clinical obesity or overweight disorders in mammals, including, but not limited to, human. Compositions of the present invention can be administered by oral, sublingual, parenteral, rectal, topical administration or by a transdermal patch. Transdermal patches dispense a drug at a controlled rate by presenting the drug for absorption in an efficient manner with a minimum of degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

In addition to the neutral forms of compositions of the present invention, by appropriate addition of an ionizable substituent, which does not alter the receptor specificity of the compound, physiologically acceptable salts of the compositions may also be formed and used as therapeutic agents. Different amounts of the compositions of the present invention will be required to achieve the desired biological effect. The amount will depend on factors such as the specific composition, the use for which it is intended, the means of administration, and the condition of the treated individual—all of these dosing parameters are within the level of one of ordinary skill in the medicinal arts. A typical dose can be expected to fall in the range of 0.001 to 200 mg per kilogram of body weight of the mammal. For example a typical dose can fall in the range of 0.001 to 0.01, 0.01 to 0.1, 0.1 to 1, 1 to 10, 10 to 100, or 100 to 200 mg per kilogram of body weight of the mammal. Unit doses may contain from 1 to 200 mg of the compositions of the present invention and can be administered one or more times a day, individually or in multiples. For example, unit doses can contain from 1 to 10, 10 to 50, 50 to 100, 100 to 150 or 150 to 200 mg of the compositions of the invention and can be administered one or more times a day, individually or in multiples.

The compositions of the present invention can be combined with the carrier in either solid or liquid form in a unit dose formulation. The pharmaceutical carrier must be compatible with the other ingredients in the composition and must be tolerated by the individual recipient. Other physiologically active ingredients can be incorporated into the pharmaceutical composition of the invention if desired, and if such ingredients are compatible with the other ingredients in the composition. Formulations can be prepared by any suitable method, typically by uniformly mixing the active compound(s) with liquids or finely divided solid carriers, or both, in the required proportions, and then, if necessary, forming the resulting mixture into a desired shape.

Conventional excipients, such as binding agents, fillers, acceptable wetting agents, tabletting lubricants, and disintegrants can be used in tablets and capsules for oral administration. Liquid preparations for oral administration can be in the form of solutions, emulsions, aqueous or oily suspensions, and syrups. Alternatively, the oral preparations can be in the form of dry powder that can be reconstituted with water or another suitable liquid vehicle before use. Additional additives such as suspending or emulsifying agents, non-aqueous vehicles (including edible oils), preservatives, and flavorings and colorants can be added to the liquid preparations. Parenteral dosage forms can be prepared by dissolving the compound of the invention in a suitable liquid vehicle and filter sterilizing the solution before filling and sealing an appropriate vial or ampoule. These are just a few examples of the many appropriate methods well known in the art for preparing dosage forms.

It is noted that the compositions of the invention are not intended for use only in humans, but in other non-human mammals as well. Indeed, recent advances in the area of animal health-care mandate that consideration be given for the use of compositions of the invention for the treatment of obesity in domestic animals (e.g., cats and dogs), and in other domestic animals where no disease or disorder is evident (e.g., food-oriented animals such as cows, chickens, fish, etc.). Those of ordinary skill in the art are readily credited with understanding the utility of such compositions in such settings.

The selective 5HT-2C receptor agonists of Formula (I) in the compositions can be readily prepared according to a variety of synthetic manipulations, all of which would be familiar to one skilled in the art. A representative general synthesis is set forth below in Scheme I

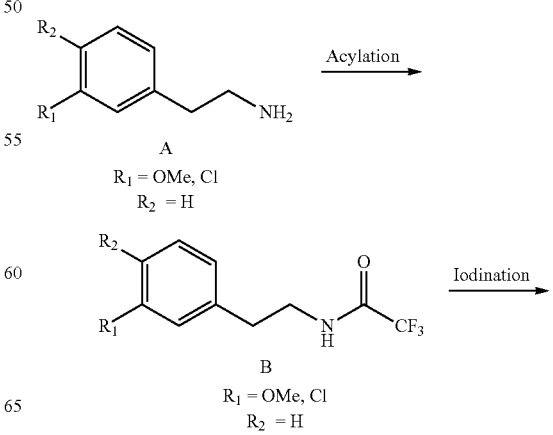

Scheme I GENERAL REACTION SCHEME

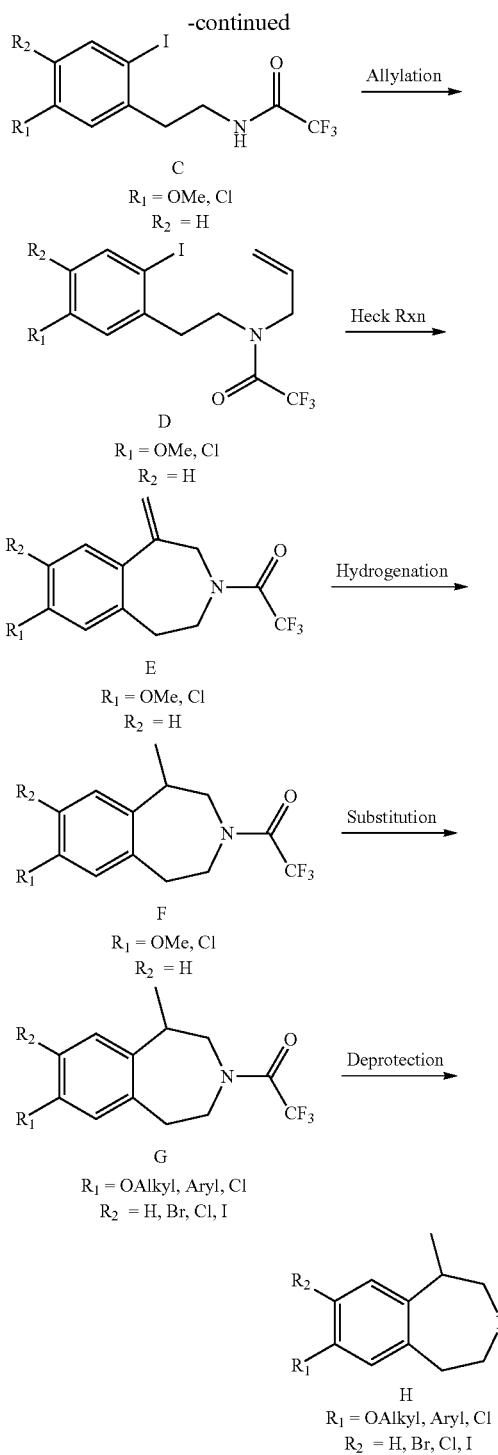

Those of skill in the art will appreciate that a wide variety of selective 5HT-2C receptor agonist compounds described in the invention can be prepared according to Scheme I. For example, by starting with an appropriately substituted 2-phenyl ethylamino compound A' having any of a wide variety of substituents $R_1$ and $R_2$, the corresponding 7- and/or 8-substituted 1-methyl-2,3,4,5-tetrahydro-1H-3-benzazepine (compound H) can be prepared. N-alkylation can be accomplished by, for example, treatment with excess paraformaldehyde (for methylation) or a higher order aldehyde, followed by reduction with $NaBH_3CN$ according to the general procedure of synthetic examples 9 and 10, infra. In addition, by starting with an appropriately substituted 1-alkyl-2-phenyl ethylamino compound A' having any of a wide variety of substituents $R_1$ and $R_2$, the corresponding 7- and/or 8-substituted 2,5-dialkyl-2,3,4,5-tetrahydro-1H-3-benzazepine compound can be prepared.

In the synthesis of many compounds of the invention, protecting groups can be required to protect various functionality or functionalities during the synthesis. Representative protecting groups suitable for a wide variety of synthetic transformations are disclosed in Greene and Wuts, Protective Groups in Organic Synthesis, 2d ed, John Wiley & Sons, New York, 1991, the disclosure of which is incorporated herein by reference in its entirety.

The invention provides a method of decreasing food intake of a mammal comprising administering to said mammal a pharmaceutically effective amount of a combination comprising a selective 5HT-2C receptor agonist and an amount of phentermine, wherein said selective 5HT-2C receptor agonist and phentermine are provided in amounts to give a synergistic effect in decreasing food intake in said mammal. For example, the invention provides a method of decreasing food intake of a mammal comprising administering to said mammal a pharmaceutically effective amount of a combination comprising an amount of (R)-8-chloro-1-methyl-2,3,4,5-tetrahydro-1H-3-benzazepine and an amount of phentermine, wherein said (R)-8-chloro-1-methyl-2,3,4,5-tetrahydro-1H-3-benzazepine and phentermine are provided in amounts to give a synergistic effect in decreasing food intake in said mammal. In one embodiment, the amount of selective 5HT-2C receptor agonist, for example, (R)-8-chloro-1-methyl-2,3,4,5-tetrahydro-1H-3-benzazepine, alone and/or the amount of phentermine alone are therapeutically effective (i.e. showing a statistically significant effect) in decreasing food intake in said mammal and the compounds are provided in amounts to give a synergistic effect in decreasing food intake in said mammal.

In one embodiment, the amount of selective 5HT-2C receptor agonist, for example, (R)-8-chloro-1-methyl-2,3,4,5-tetrahydro-1H-3-benzazepine, alone and/or the amount of phentermine alone are therapeutically sub-effective in decreasing food intake in said mammal. As used herein, "therapeutically sub-effective" means that the 5HT-2C agonist and/or phentermine are provided in amounts that do not have a statistically significant effect on the measured parameter. For example, the amount of selective 5HT-2C receptor agonist, for example, (R)-8-chloro-1-methyl-2,3,4,5-tetrahydro-1H-3-benzazepine, alone and/or the amount of phentermine alone can be therapeutically ineffective in decreasing food intake in said mammal. Since the combination of a selective 5HT-2C receptor agonist and phentermine have a synergistic effect (see, for example, FIG. 2, FIGS. 3A and B, and FIGS. 4A and B), the combination therapy can be therapeutically effective while each of the compounds separately are therapeutically sub-effective (which includes, for example, when the compound or compounds are ineffective). In a method of treatment, a therapeutically effective dose of the combination of the selective 5HT-2C receptor agonist and phentermine is used.

The invention also provides a method of inducing satiety in a mammal comprising administering to said mammal a pharmaceutically effective amount of a combination comprising an amount of a selective 5HT-2C receptor agonist and an amount of phentermine, wherein said selective 5HT-2C receptor agonist and phentermine are provided in amounts to give a synergistic effect in inducing satiety in said mammal. For example, the invention provides a method of inducing satiety in a mammal comprising administering to said mammal a pharmaceutically effective amount of a combination comprising an amount of (R)-8-chloro-1-methyl-2,3,4,5-tetrahydro-1H-3-benzazepine and/or an amount of phentermine, wherein said (R)-8-chloro-1-methyl-2,3,4,5-tetrahydro-1H-3-benzazepine and phentermine are provided in amounts to give a synergistic effect in inducing satiety in said mammal. In one embodiment, the amount of selective 5HT-2C receptor agonist, for example, (R)-8-chloro-1-methyl-2,3,4,5-tetrahydro-1H-3-benzazepine, alone and/or the amount of phentermine alone are therapeutically sub-effective or ineffective in inducing satiety in said mammal.

In addition, the invention provides a method of controlling weight gain of a mammal comprising administering to said mammal a pharmaceutically effective amount of a combination comprising an amount of a selective 5HT-2C receptor agonist and an amount of phentermine, wherein said selective 5HT-2C receptor agonist and phentermine are provided in amounts to give a synergistic effect in controlling weight gain in said mammal. For example, the invention provides a method of controlling weight gain of a mammal comprising administering to said mammal a pharmaceutically effective amount of a combination comprising an amount of (R)-8-chloro-1-methyl-2,3,4,5-tetrahydro-1H-3-benzazepine and/or an amount of phentermine, wherein said (R)-8-chloro-1-methyl-2,3,4,5-tetrahydro-1H-3-benzazepine and phentermine are provided in amounts to give a synergistic effect in controlling weight gain in said mammal. In one embodiment, the amount of selective 5HT-2C receptor agonist, for example, (R)-8-chloro-1-methyl-2,3,4,5-tetrahydro-1H-3-benzazepine, alone and/or the amount of phentermine alone are therapeutically sub-effective or ineffective in controlling weight gain in said mammal.

The invention further provides a method of prophylaxis or treatment of obesity, or a condition related thereto, comprising administering to a patient in need of such prophylaxis or treatment a therapeutically effective amount of a combination comprising an amount of a selective 5HT-2C receptor agonist and an amount of phentermine, wherein said selective 5HT-2C receptor agonist and phentermine are provided in amounts to give a synergistic effect in decreasing food intake in said mammal. For example, the invention further provides a method of prophylaxis or treatment of obesity, or a condition related thereto, comprising administering to a patient in need of such prophylaxis or treatment a therapeutically effective amount of a combination comprising an amount of (R)-8-chloro-1-methyl-2,3,4,5-tetrahydro-1H-3-benzazepine and an amount of phentermine, wherein said (R)-8-chloro-1-methyl-2,3,4,5-tetrahydro-1H-3-benzazepine and phentermine are provided in amounts to give a synergistic effect in decreasing food intake in said mammal. In one embodiment, the amount of selective 5HT-2C receptor agonist, for example, (R)-8-chloro-1-methyl-2,3,4,5-tetrahydro-1H-3-benzazepine, alone and/or the amount of phentermine alone are therapeutically sub-effective or ineffective in decreasing food intake in said mammal. Conditions related to obesity include, for example, type II diabetes, atherosclerosis, high blood pressure, syndrome X and the like. In some embodiments the disorder is obesity.

The invention also provides the above disclosed methods further comprising the step of identifying a subject, said subject being in need of prophylaxis or treatment for obesity, or a condition related thereto, wherein said identifying step is performed prior to administering to said subject said therapeutically effective amount of said compounds.

One aspect of the present invention pertains to a method for the treatment of obesity, or a condition related thereto, comprising administering to a subject suffering form said condition a therapeutically effective amount of a composition comprising a selective 5HT-2C receptor agonist and phentermine, as described herein, preferably in the form of a pharmaceutical composition.

One aspect of the present invention pertains to a composition comprising a selective 5HT-2C receptor agonist and phentermine for use in a method of treatment of the human or animal body by therapy. For example, the invention provides a composition of the invention for use in a method of treatment of a 5HT2C disorder of the human or animal body by therapy. The invention also provides a composition of the invention for use in a method of prophylaxis or treatment of obesity of a mammal, for use in a method of decreasing food intake of a mammal, for use in a method of inducing satiety in a mammal, and/or for use in a method of controlling weight gain of a mammal.

One aspect of the present invention pertains to a composition of the invention for the manufacture of a medicament for use in the propylaxis or treatment of a 5HT2C disorder of the human or animal body by therapy. For example, one aspect of the present invention pertains to a composition comprising a selective 5HT-2C receptor agonist and phentermine for the manufacture of a medicament for use in the propylaxis or treatment of obesity, or conditions related thereto. In some embodiments the disorder is obesity. In addition, for example, the invention provides a composition of the invention for the manufacture of a medicament for use in a method of decreasing food intake of a mammal, for the manufacture of a medicament for use in a method of inducing satiety in a mammal, and/or for the manufacture of a medicament for use in a method of controlling weight gain of a mammal.

In some embodiments, the invention provides methods for alleviation of a symptom of any of the diseases, conditions or disorders mentioned herein.

As will be recognized, the steps of the methods of the present invention need not be performed any particular number of times or in any particular sequence. Additional objects, advantages, and novel features of this invention will become apparent to those skilled in the art upon examination of the following examples thereof, which are intended to be illustrative and not intended to be limiting.

EXAMPLES

Synthetic Examples

Example 1

(R,S) 8-Bromo-7-methoxy-1-methyl-2,3,4,5-tetrahydro-1H-3-benzazepine

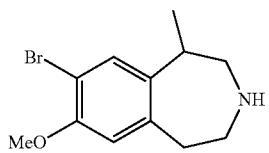

N-Trifluoroacetyl-3-methoxyphenethylamine

A solution of 3-methoxyphenethylamine (10.0 g, 64.0 mmol) in dichloromethane (150 mL), was cooled to 0° C., and treated with pyridine (6.5 mL, 83.5 mmol) followed by the dropwise addition of trifluoracetic anhydride (17.9 g, 83.5 mmol) and the resulting mixture stirred for 3 hours while warming to 20° C. The product mixture was diluted with EtOAc (500 mL), washed sequentially with 10% aqueous HCl (100 mL), water (100 mL), brine (100 mL), dried with $Na_2SO_4$ and concentrated to give 15.8 g of a yellow oil. $^1H$ NMR (400 MHz, $CDCl_3$) δ 7.26 (dd, J=8, 8 Hz, 1H), 6.81 (d, J=8 Hz, 1H), 6.77 (d, J=8 Hz, 1H), 6.72 (s, 1H), 6.30 (bs, 1H), 3.80 (s, 3H), 3.62 (dd, J=7, 7 Hz, 2H), 2.86 (dd, J=7, 7 Hz, 2H). MS calculated for $C_{11}H_{12}F_3NO_2$+H: 248, observed: 248.

N-Trifluoroacetyl-2-iodo-5-methoxyphenethylamine

A solution of N-trifluoroacetyl-3-methoxyphenethylamine (15.8 g, 64 mmol) in methanol (325 mL) was cooled to −78° C., and treated with $CaCO_3$ (14.7 g, 145 mmol), followed by a solution of ICl (29 g, 181 mmol) in methanol (40 mL). The reaction was allowed to warm to 20° C. while stirring overnight and then filtered, concentrated, dissolved in EtOAc (200 mL), washed twice with 5% aqueous sodium bisulfite (100 mL), once with brine (100 mL), dried with $Na_2SO_4$ and concentrated to give 23.8 g of a white solid powder. $^1H$ NMR (400 MHz, $CDCl_3$) δ 7.68 (d, J=9 Hz, 1H), 6.76 (s, 1H), 6.57 (d, J=9 Hz, 1H), 6.42 (bs, 1H), 3.77 (s, 3H), 3.61 (dd, J=7, 7 Hz, 2H), 2.99 (dd, J=7, 7 Hz, 2H). MS calculated for $C_{11}H_{11}F_3INO_2$+H: 374, observed: 374.

N-Allyl, N-trifluoroacetyl-2-iodo-5-methoxyphenethylamine

A solution of N-trifluoroacetyl-2-iodo-5-methoxyphenethylamine (23.8 g, 63.8 mmol) in toluene (425 mL) was sequentially treated with $K_2CO_3$ (12.4 g, 89.8 mmol), KOH (11.6 g, 207 mmol), n-$Bu_4NBr$ (2.2 g, 6.9 mmol) and allyl bromide (10.7 g, 89.8 mmol). The mixture was stirred at 80° C. for 3.5 hours, cooled to 20° C., acidified with 10% aqueous HCl, separated and the aqueous phase extracted with ether (500 mL). The combined organic phases were washed with brine (200 mL), dried with $Na_2SO_4$ and concentrated to give 20.5 g of a brown oil. $^1H$ NMR (400 MHz, $CDCl_3$), mixture of rotamers d 7.67 (m, 1H), 6.80 (m, 1H), 6.57 (m, 1H), 5.9-5.6 (bm, 1H), 5.27 (m, 2H), 4.11 (d, J=6 Hz, 0.5H), 3.85 (d, J=6 Hz, 0.5H), 3.77 (m, 3H), 3.55 (m, 2H), 3.00 (m, 2H). MS calculated for $C_{14}H_{15}F_3INO_2$+H: 414, observed: 414.

N-Trifluoroacetyl-7-methoxy-1-methylene-2,3,4,5-tetrahydro-1H-3-benzazepine

A solution of N-allyl, N-trifluoroacetyl-2-iodo-5-methoxyphenethylamine (20.5 g, 50 mmol) in dimethylformamide (250 mL) is treated with KOAc (14.6 g, 149 mmol), n-$Bu_4NBr$ (16.0 g, 50 mmol), $PPh_3$ (1.3 g, 5.0 mmol), $Pd(OAc)_2$ (0.56 g, 2.5 mmol) and stirred overnight at 90° C. The product mixture was cooled to 20° C., filtered, diluted with water (500 mL) and extracted with ether (3×500 mL). The combined organic phases were washed with water (100 mL), brine (100 mL), dried with $Na_2SO_4$ and concentrated. Flash chromatography (10% EtOAc in hexane, silica) resulted in 6.6 g of a yellow oil. $^1H$ NMR (400 MHz, $CDCl_3$) δ 7.26 (d, J=8 Hz, 1H), 6.77 (d, J=8 Hz, 1H), 6.66 (s, 1H), 5.34-5.19 (m, 2H), 4.40 (m, 2H), 3.83 (m, 2H), 3.80 (s, 3H), 3.00 (m, 2H). MS calculated for $C_{14}H_{14}F_3NO_2$+H: 285, observed: 285.

N-Trifluoroacetyl-7-methoxy-1-methyl-2,3,4,5-tetrahydro-1H-3-benzazepine

A solution of N-trifluoroacetyl-7-methoxy-1-methylene-2,3,4,5-trihydro-1H-3-benzazepine (6.6 g, 23.2 mmol) in ethanol (100 mL), was treated with 10% Pd/C (0.75 g, 2.3 mmol) and stirred overnight under an atmosphere of hydrogen. The product mixture was filtered through a pad of celite and silica and the solvent removed to give 6.27 g of a white solid. $^1H$ NMR (400 MHz, $CDCl_3$, mixture of rotamers) δ 7.10 (m, 1H), 6.74 (m, 1H), 6.68 (m, 1H), 4.1-3.8 (bm, 2H), 3.8 (s, 3H), 3.5 (m, 1.5H), 3.4 (m, 0.5H), 3.2-2.9 (bm, 4H), 1.32 (m, 3H). MS calculated for $C_{14}H_{16}F_3NO_2$+H: 288, observed: 288.

N-Trifluoroacetyl-8-bromo-7-methoxy-1-methyl-2,3,4,5-tetrahydro-1H-3-benzazepine A solution of N-trifluoroacetyl-7-methoxy-1-methyl-2,3,4,5-tetrahydro-1H-3-benzazepine (1.25 g, 4.35 mmol) in acetonitrile (40 mL) was treated with N-bromosuccinimide (0.852 g, 4.79 mmol) and stirred overnight at 20° C. The product mixture was diluted with EtOAc (200 mL), washed with saturated aqueous sodium bisulfite (100 mL) and brine (100 mL), dried with $Na_2SO_4$ and concentrated. Flash chromatography (15% EtOAc in hexane, silica) resulted in 1.55 g of a clear oil. $^1H$ NMR (400 MHz, $CDCl_3$, mixture of rotamers) δ 7.34 (s, 1H), 6.65 (m, 1H), 3.87 (s, 3H), 3.81 (m, 1H), 3.55 (m, 1.3H), 3.37 (m, 0.7H), 3.2-2.9 (bm, 4H), 1.30 (m, 3H). MS calculated for $C_{14}H_{15}BrF_3NO_2$+H: 366, observed: 366.

8-Bromo-7-methoxy-1-methyl-2,3,4,5-tetrahydro-1H-3-benzazepine

A solution of N-trifluoroacetyl-8-bromo-7-methoxy-1-methyl-2,3,4,5-tetrahydro-1H-3-benzazepine (0.95 g, 2.59 mmol) in methanol (20 mL) was treated with 15% aqueous NaOH (25 mL), and stirred overnight at 20° C. The product mixture was diluted with water (100 mL), extracted twice with EtOAc (100 mL), the combined organic phases were washed with brine (100 mL), dried with $Na_2SO_4$ and concentrated to give 0.687 g of a clear oil. $^1H$ NMR (400 MHz, $CDCl_3$) δ 7.92 (s, 1H), 6.34 (s, 1H), 3.87 (s, 3H), 3.1-2.9 (m, 6H), 2.75 (m, 1H), 2.60 (bs, 1H), 1.31 (d, J=7 Hz, 3H). MS calculated for $C_{12}H_{16}BrNO$+H: 270, observed: 270.

Example 2

(R,S) 8-Chloro-7-methoxy-1-methyl-2,3,4,5-tetrahydro-1H-3-benzazepine

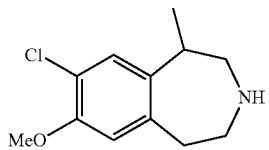

N-Trifluoroacetyl-8-chloro-7-methoxy-1-methyl-2,3,4,5-tetrahydro-1H-3-benzazepine A solution of N-trifluoroacetyl-7-methoxy-1-methyl-2,3,4,5-tetrahydro-1H-3-benzazepine (0.900 g, 2.67 mmol) in acetonitrile (30 mL) was treated with N-chlorosuccinimide (0.357 g, 2.67 mmol) and stirred overnight at 70° C. The product mixture was diluted with water (100 mL), extracted twice with EtOAc (100 mL), the combined organic phases washed with brine (100 mL), dried with $Na_2SO_4$ and concentrated. Flash chromatography (20% EtOAc in hexane, silica) resulted in 0.399 g of a clear oil. $^1$H NMR (400 MHz, CDCl$_3$, mixture of rotamers) δ 7.17 (s, 1H), 6.68 (m, 1H), 3.88 (s, 3H), 3.78 (m, 1H), 3.6-3.3 (m, 2H), 3.2-2.9 (m, 4H), 1.34 (m, 3H). MS calculated for C$_{14}$H$_{15}$ClF$_3$NO$_2$+H: 322, observed: 322.

8-Chloro-7-methoxy-1-methyl-2,3,4,5-tetrahydro-1H-3-benzazepine

A solution of N-trifluoroacetyl-8-chloro7-methoxy-1-methyl-2,3,4,5-tetrahydro-1H-3-benzazepine (0.399 g, 1.24 mmol) in methanol (20 mL) was treated with 15% aqueous NaOH (20 mL), and stirred overnight at 20° C. The product mixture was diluted with water (100 mL), extracted twice with EtOAc (100 mL), the combined organic phases were washed with brine (100 mL), dried with Na$_2$SO$_4$ and concentrated to give 0.306 g of a yellow solid. $^1$H NMR (400 MHz, CDCl$_3$) δ 7.05 (s, 1H), 6.59 (s, 1H), 3.80 (s, 3H), 3.0-2.8 (m, 6H), 2.62 (m, 1H), 2.16 (bs, 1H), 1.24 (d, J=7 Hz, 3H). MS calculated for C$_{12}$H$_{16}$ClNO+H: 226, observed: 226.

Example 3

(R,S) 8-Iodo-7-methoxy-1-methyl-2,3,4,5-taetrhydro-1H-3-benzazepine

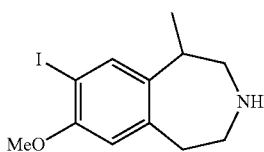

N-Trifluoroacetyl-8-iodo-7-methoxy-1-methyl-2,3,4,5-tetrahydro-1H-3-benzazepine

A solution of N-trifluoroacetyl-7-methoxy-1-methyl-2,3,4,5-tetrahydro-1H-3-benzazepine (1.50 g, 5.22 mmol) in methanol (70 mL) was treated with CaCO$_3$ (1.06 g, 10.44 mmol) followed by a solution of ICl (1.70 g, 10.44 mmol) in methanol (10 mL), and stirred overnight at 20° C. The product mixture was filtered, concentrated, dissolved in EtOAc (200 mL), extracted twice with 5% aqueous sodium bisulfite (100 mL), once with brine (100 mL), dried with Na$_2$SO$_4$ and concentrated. Flash chromatography (15% EtOAc in hexane, silica) resulted in 1.54 g of a white solid. $^1$H NMR (400 MHz, CDCl$_3$, mixture of rotamers) δ 7.55 (m, 1H), 6.57 (m, 1H), 3.86 (s, 3H), 3.80 (m, 1H), 3.60-3.30 (m, 2H), 3.20-2.80 (m, 4H), 1.30 (m, 3H). MS calculated for C$_{14}$H$_{15}$F$_3$INO$_2$+H: 414, observed: 414.

8-Iodo-7-methoxy-1-methyl-2,3,4,5-tetrahydro-1H-3-benzazepine

A solution of N-trifluoroacetyl-8-iodo7-methoxy-1-methyl-2,3,4,5-tetrahydro-1H-3-benzazepine (0.600 g, 1.45 mmol) in methanol (20 mL) was treated with 15% aqueous NaOH (20 mL), and stirred for 3 hours at 50° C. The product mixture was diluted with water (100 mL), extracted twice with EtOAc (100 mL), the combined organic phases were washed with brine (100 mL), dried with Na$_2$SO$_4$ and concentrated to give 0.425 g of a yellow solid. $^1$H NMR (400 MHz, CDCl$_3$) δ 7.52 (s, 1H), 6.57 (s, 1H), 3.86 (s, 3H), 3.12-3.06 (m, 4H), 2.95 (m, 2H), 2.75 (m, 1H), 2.43 (bs, 1H), 1.33 (d, J=8 Hz, 3H). MS calculated for C$_{12}$H$_{16}$INO+H: 318, observed: 318.

Example 4

(R,S) 8-Bromo-7-hydroxy-1-methyl-2,3,4,5-tetrahydro-1H-3-benzazepine

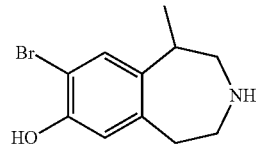

N-Trifluoroacetyl-8-bromo-7-hydroxy-1-methyl-2,3,4,5-tetrahydro-1H-3-benzazepine A solution of N-trifluoroacetyl-8-bromo-7-methoxy-1-methyl-2,3,4,5-tetrahydro-1H-3-benzazepine (1.50 g, 4.10 mmol) in dichloromethane (80 mL) was treated dropwise with BBr$_3$ (9.4 mL of a 1.0M solution in CH$_2$Cl$_2$, 9.4 mmol), and the mixture stirred overnight while warming to 20° C. The excess BBr$_3$ was quenched with the dropwise addition of water, the mixture diluted with ether (200 mL), washed with Na$_2$CO$_3$ (100 mL) and brine (100 mL), dried with Na$_2$SO$_4$ and concentrated. Flash chromatography (15% EtOAc in hexane, silica) resulted in 1.25 g of a white solid foam. $^1$H NMR (400 MHz, CDCl$_3$, mixture of rotamers) δ 7.25 (s, 1H), 6.79 (m, 1H), 3.79 (m, 1H), 3.7-3.3 (m, 2H), 3.2-2.8 (m, 4H), 1.32 (m, 3H).

8-Bromo-7-hydroxy-1-methyl-2,3,4,5-tetrahydro-1H-3-benzazepine

A solution of N-trifluoroacetyl-8-bromo-7-hydroxy-1-methyl-2,3,4,5-tetrahydro-1H-3-benzazepine (0.655 g, 1.89 mmol) in methanol (20 mL) was treated with 15% aqueous NaOH (20 mL), and stirred overnight at 20° C. The product mixture was diluted with water (100 mL), extracted twice with EtOAc (100 mL), the combined organic phases were washed with brine (100 mL), dried with Na$_2$SO$_4$ and concentrated to give 0.460 g of a clear oil. $^1$H NMR (400 MHz, DMSO-d$_6$) δ 7.11 (s, 1H), 6.65 (s, 1H), 2.90 (m, 1H), 2.73 (m, 5H), 2.55 (m, 1H), 1.19 (d, J=7 Hz, 3H). MS calculated for C$_{11}$H$_{14}$BrNO+H: 256, observed: 256.

Example 5

(R,S) 7-Allyloxy-8-bromo-1-methyl-2,3,4,5-tetrahydro-1H-3-benzazepine

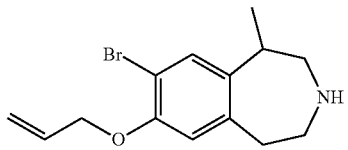 [SMILES: C=CCOc1cc2c(cc1Br)C(C)CNCC2]

N-Trifluoroacetyl-7-allyloxy-8-bromo-1-methyl-2,3,4,5-tetrahydro-1H-3-benzazepine A solution of N-trifluoroacetyl-8-bromo-7-hydroxy-1-methyl-2,3,4,5-tetrahydro-1H-3-benzazepine (0.150 g, 0.426 mmol) in dichloromethane (5 mL) was treated with allyl bromide (0.155 g, 1.28 mmol) and DBU (0.195 g, 1.28 mmol) and then stirred 2 hours at 20° C. The product mixture was diluted with EtOAc (50 mL), washed with 5% aqueous HCl (20 mL), brine (20 mL), dried with Na$_2$SO$_4$ and concentrated. Flash chromatography (15% EtOAc in hexane, silica) resulted in 0.149 g of a clear oil. $^1$H NMR (400 MHz, CDCl$_3$, mixture of rotamers) δ 7.34 (s, 1H), 6.65 (m, 1H), 6.04 (m, 1H), 5.47 (d, J=17 Hz, 1H), 5.30 (d, J=9 Hz, 1H), 4.59 (s, 2H), 3.80 (m, 1H), 3.6-3.3 (m, 3H), 3.2-2.8 (m, 4H), 1.31 (m, 3H). MS calculated for C$_{16}$H$_{17}$BrF$_3$NO$_2$+H: 392, observed: 392.

7-Allyloxy-8-bromo-1-methyl-2,3,4,5-tetrahydro-1H-3-benzazepine

A solution of N-trifluoroacetyl-7-allyloxy-8-bromo-1-methyl-2,3,4,5-tetrahydro-1H-3-benzazepine (1.18 g, 3.00 mmol) in methanol (35 mL) was treated with 15% aqueous NaOH (35 mL), and stirred overnight at 20° C. The product mixture was diluted with water (200 mL), extracted twice with EtOAc (200 mL), the combined organic phases were washed with brine (100 mL), dried with Na$_2$SO$_4$ and concentrated to give 0.880 g of a clear oil. $^1$H NMR (400 MHz, CDCl$_3$) δ 7.29 (s, 1H), 6.63 (s, 1H), 6.04 (m, 1H), 5.47 (d, J=17 Hz, 1H), 5.29 (d, J=11 Hz, 1H), 4.58 (s, 2H), 3.01 (m, 3H), 2.89 (m, 3H), 2.75 (m, 1H), 1.31 (d, J=7 Hz, 3H). MS calculated for C$_{14}$H$_{18}$BrNO+H: 296, observed: 296.

Example 6

(R,S) 7-Benzyloxy-8-bromo-1-methyl-2,3,4,5-tetrahydro-1H-3-benzazepine

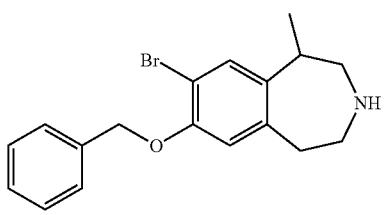 [SMILES: CC1CNCCc2cc(OCc3ccccc3)c(Br)cc21]

N-Trifluoroacetyl-7-benzyloxy-8-bromo-1-methyl-2,3,4,5-tetrahydro-1H-3-benzazepine A solution of N-trifluoroacetyl-8-bromo-7-hydroxy-1-methyl-2,3,4,5-tetrahydro-1H-3-benzazepine (0.075 g, 0.213 mmol) in dichloromethane (5 mL) was treated with benzyl bromide (0.072 g, 0.64 mmol), DBU (0.100 g, 0.64 mmol), and stirred 2 hours at 20° C. The product mixture was diluted with EtOAc (50 mL), washed with 5% aqueous HCl (20 mL), brine (20 mL), dried with Na$_2$SO$_4$ and concentrated. Flash chromatography (15% EtOAc in hexane, silica) resulted in 0.081 g of a clear oil. MS calculated for C$_{20}$H$_{19}$BrF$_3$NO$_2$+H: 442, observed: 442.

7-Benzyloxy-8-bromo-1-methyl-2,3,4,5-tetrahydro-1H-3-benzazepine

A solution of N-trifluoroacetyl-7-benzyloxy-8-bromo-1-methyl-2,3,4,5-tetrahydro-1H-3-benzazepine (0.81 g, 1.83 mmol) in methanol (20 mL) was treated with 15% aqueous NaOH (20 mL), and stirred overnight at 20° C. The product mixture was diluted with water (200 mL), extracted twice with EtOAc (200 mL), the combined organic phases were washed with brine (100 mL), dried with Na$_2$SO$_4$ and concentrated to give 0.412 g of a clear oil. $^1$H NMR (400 MHz, CDCl$_3$) δ 7.38 (d, J=8 Hz, 2H), 7.30 (dd, J=7, 8 Hz, 2H), 7.23 (m, 2H), 6.61 (s, 1H), 5.03 (s, 2H), 2.94 (m, 3H), 2.81 (m, 3H), 2.62 (m, 1H), 2.30 (bs, 1H), 1.24 (d, J=7 Hz, 3H). MS calculated for C$_{18}$H$_{20}$BrNO+H: 346, observed: 346.

Example 7

(R,S) 8-Bromo-7-ethoxy-1-methyl-2,3,4,5-tetrahydro-1H-3-benzazepine

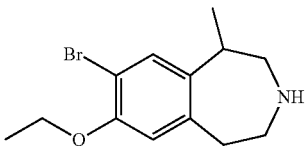 [SMILES: CCOc1cc2c(cc1Br)C(C)CNCC2]

N-Trifluoroacetyl-8-bromo-7-ethoxy-1-methyl-2,3,4,5-tetrahydro-1H-3-benzazepine

A solution of N-trifluoroacetyl-8-bromo-7-hydroxy-1-methyl-2,3,4,5-tetrahydro-1H-3-benzazepine (0.015 g, 0.043 mmol) in dichloromethane (1 mL) was treated with ethyl iodide (0.016 g, 0.102 mmol), DBU (0.016 g, 0.102 mmol) and stirred 2 hours at 20° C. The product mixture was diluted with EtOAc (10 mL), washed with 5% aqueous HCl (5 mL), brine (5 mL), dried with Na$_2$SO$_4$ and concentrated. Flash chromatography (15% EtOAc in hexane, silica) resulted in 0.010 g of a clear oil.

8-Bromo-7-ethoxy-1-methyl-2,3,4,5-tetrahydro-1H-3-benzazepine

A solution of N-trifluoroacetyl-8-bromo-7-ethoxy-1-methyl-2,3,4,5-tetrahydro-1H-3-benzazepine (0.010 g, 0.026 mmol) in methanol (1 mL) was treated with 15% aqueous NaOH (1 mL), and stirred overnight at 20° C. The product mixture was diluted with water (3 mL), extracted twice with EtOAc (5 mL), the combined organic phases were washed with brine (3 mL), dried with Na$_2$SO$_4$ and concentrated to give 0.007 g of a clear oil. $^1$H NMR (400 MHz, CDCl$_3$) δ 7.29 (s, 1H), 6.63 (s, 1H), 4.07 (q, J=6 Hz, 2H), 3.03 (m, 3H), 2.91 (m, 3H), 2.73 (m, 1H), 2.26 (bs, 1H), 1.46 (t, J=6 Hz, 3H), 1.32 (d, J=7 Hz, 3H). MS calculated for C$_{15}$H$_{17}$BrF$_3$NO$_2$+H: 380, observed: 380.

Example 8

(R,S) 8-Bromo-7-isopropoxy-1-methyl-2,3,4,5-tetrahydro-1H-3-benzazepine

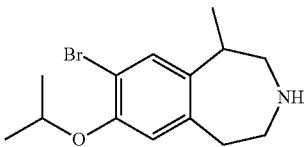 [SMILES: CC(C)Oc1cc2c(cc1Br)C(C)CNCC2]

N-Trifluoroacetyl-8-bromo-7-isopropoxy-1-methyl-2,3,4,5-tetrahydro-1H-3-benzazepine A solution of N-trifluoroacetyl-8-bromo-7-hydroxy-1-methyl-2,3,4,5-tetrahydro-1H-3-benzazepine (0.035 g, 0.099 mmol) in dichloromethane (1 mL) was treated with isopropyl bromide (0.037 g, 0.297 mmol), DBU (0.048 g, 0.205 mmol) and stirred 2 hours at 20° C. The product mixture was diluted with EtOAc (10 mL), washed with 5% aqueous HCl (5 mL), brine (5 mL), dried with $Na_2SO_4$ and concentrated. Flash chromatography (15% EtOAc in hexane, silica) resulted in 0.014 g of a clear oil. MS calculated for $C_{16}H_{19}BrF_3NO_2$+H: 394, observed: 394.

8-Bromo-7-isopropoxy-1-methyl-2,3,4,5-tetrahydro-1H-3-benzazepine

A solution of N-trifluoroacetyl-8-bromo-7-isopropoxy-1-methyl-2,3,4,5-tetrahydro-1H-3-benzazepine (0.014 g, 0.035 mmol) in methanol (1 mL) was treated with 15% aqueous NaOH (1 mL), and stirred overnight at 20° C. The product mixture was diluted with water (3 mL), extracted twice with EtOAc (5 mL), the combined organic phases were washed with brine (3 mL), dried with $Na_2SO_4$ and concentrated to give 0.008 g of a clear oil. $^1$H NMR (400 MHz, $CDCl_3$) δ 7.24 (s, 1H), 6.64 (s, 1H), 4.48 (m, 1H), 2.98 (m, 3H), 2.87 (m, 3H), 1.36 (m, 6H), 1.30 (d, J=7 Hz, 3H). MS calculated for $C_{14}H_{20}BrNO$+H: 298, observed: 298.

Example 9

(R,S) N-Methyl-8-bromo-7-methoxy-1-methyl-2,3,4,5-tetrahydro-1H-3-benzazepine

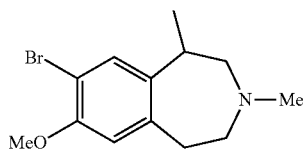 [SMILES: COc1cc2c(cc1Br)C(C)CN(C)CC2]

A solution of 8-Bromo-7-methoxy-1-methyl-2,3,4,5-tetrahydro-1H-3-benzazepine (6 mg, 0.022 mmol) in methanol (1 mL) was treated with excess paraformaldehyde, 1.0 M HCl in ether (0.004 mL, 0.004 mmol), $NaBH_3CN$ (1.0 mg, 0.013 mmol), and stirred overnight at 20° C. The product mixture was diluted with 5% aqueous NaOH (5 mL), extracted 3 times with $CH_2Cl_2$ (5 mL each), the combined organic phases were dried with $Na_2SO_4$ and concentrated. Flash chromatography (10% MeOH in $CH_2Cl_2$, silica) resulted in 5 mg of a clear oil. $^1$H NMR (400 MHz, $CDCl_3$) δ 7.31 (s, 1H), 6.66 (s, 1H), 3.87 (s, 3H), 3.26 (bm, 2H), 3.01 (bs, 1H), 2.85 (m, 2H), 2.45 (s, 3H), 2.45-2.25 (m, 2H), 1.36 (d, J=7 Hz, 3H). MS calculated for $C_{13}H_{18}BrNO$+H: 284, observed: 284.

Example 10

(R,S) N-Propyl-8-bromo-7-methoxy-1-methyl-2,3,4,5-tetrahydro-1H-3-benzazepine

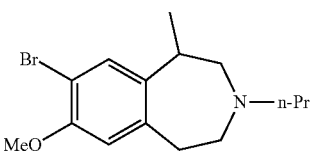

A solution of 8-Bromo-7-methoxy-1-methyl-1,2,4,5-tetrahydro-3H-3-benzazepine (6 mg, 0.022 mmol) in methanol (1 mL) was treated with propionaldehyde (5.0 mg, 0.067 mmol), 1.0 M HCl in ether (0.004 mL, 0.004 mmol), $NaBH_3CN$ (1.0 mg, 0.013 mmol), and stirred overnight at 20° C. The product mixture was diluted with 5% aqueous NaOH (5 mL), extracted 3 times with $CH_2Cl_2$ (5 mL each), the combined organic phases were dried with $Na_2SO_4$ and concentrated. Flash chromatography (10% MeOH in $CH_2Cl_2$, silica) resulted in 4 mg of a clear oil. $^1$H NMR (400 MHz, $CD_3OD$) δ 7.33 (s, 1H), 6.87 (s, 1H), 3.84 (s, 3H), 3.25 (m, 2H), 3.11 (m, 2H), 2.97 (m, 1H), 2.78 (bm, 2H), 2.63 (bm, 2H), 1.67 (m, 2H), 1.38 (d, J=7 Hz, 3H), 0.96 (t, J=7 Hz, 3H). MS calculated for $C_{15}H_{22}BrNO$+H: 312, observed: 312.

Example 11

(R,S) 7-Hydroxy-8-iodo-1-methyl-2,3,4,5-tetrahydro-1H-3-benzazepine

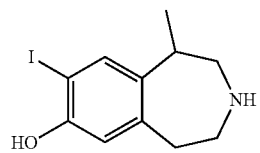

N-Trifluoroacetyl-7-hydroxy-8-iodo-1-methyl-2,3,4,5-tetrahydro-1H-3-benzazepine

A solution of N-trifluoroacetyl-8-iodo-7-methoxy-1-methyl-2,3,4,5-tetrahydro-1H-3-benzazepine (80 mg, 0.19 mmol) in dichloromethane (3 mL) was treated with $BBr_3$ (0.40 mL of a 1.0M solution in $CH_2Cl_2$, 0.40 mmol) and stirred overnight at 20° C. The excess $BBr_3$ was quenched with water and the product mixture was diluted with ether (20 mL), washed with $Na_2CO_3$ (10 mL) and brine (10 mL), dried with $Na_2SO_4$ and concentrated. Flash chromatography (15% EtOAc in hexane, silica) resulted in 74 mg of a white solid. MS calculated for $C_{13}H_{13}F_3INO_2$+H: 400, observed: 400.

7-Hydroxy-8-iodo-1-methyl-2,3,4,5-tetrahydro-1H-3-benzazepine

A solution of N-trifluoroacetyl-7-hydroxy-8-iodo-1-methyl-2,3,4,5-tetrahydro-1H-3-benzazepine (25 mg, 0.063 mmol) in methanol (2 mL) was treated with 15% aqueous NaOH (2 mL), and stirred overnight at 20° C. The product mixture was diluted with water (5 mL), extracted twice with EtOAc (5 mL), the combined organic phases were washed with brine (5 mL), dried with $Na_2SO_4$ and concentrated to give 13 mg of a white solid. $^1$H NMR (400 MHz, $CD_3OD$) δ 7.46 (s, 1H), 6.64 (s, 1H), 3.16 (m, 3H), 2.94 (m, 3H), 2.81 (m, 1H), 1.35 (d, J=7 Hz, 3H). MS calculated for $C_{11}H_{14}INO$+H: 304, observed: 304.

Example 12

(R,S) 7-Allyloxy-8-iodo-1-methyl-2,3,4,5-tetrahydro-1H-3-benzazepine

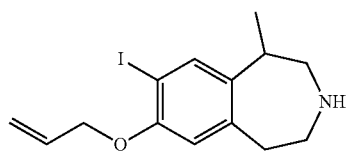 [SMILES: C=CCOc1cc2c(cc1I)C(C)CNCC2]

N-Trifluoroacetyl-7-allyloxy-8-iodo-1-methyl-2,3,4,5-tetrahydro-1H-3-benzezepine A solution of N-trifluoroacetyl-7-hydroxy-8-iodo-1-methyl-2,3,4,5-tetrahydro-1H-3-benzazepine (30 mg, 0.075 mmol) in dichloromethane (2 mL) was treated with allyl bromide (18 mg, 0.15 mmol), DBU (23 mg, 0.15 mmol) and stirred 2 hours at 20° C. The product mixture was diluted with EtOAc (10 mL), washed with 5% aqueous HCl (5 mL), brine (5 mL), dried with $Na_2SO_4$ and concentrated. Flash chromatography (15% EtOAc in hexane, silica) resulted in 23 mg of a clear oil. MS calculated for $C_{16}H_{17}F_3INO_2$+H: 440, observed: 440.

7-Allyloxy-8-iodo-1-methyl-2,3,4,5-tetrahydro-1H-3-benzezepine

A solution of N-trifluoroacetyl-7-allyloxy-8-iodo-1-methyl-2,3,4,5-tetrahydro-1H-3-benzazepine (23 mg, 0.058 mmol) in methanol (2 mL) was treated with 15% aqueous NaOH (2 mL), and stirred overnight at 20° C. The product mixture was diluted with water (5 mL), extracted twice with EtOAc (5 mL), the combined organic phases were washed with brine (5 mL), dried with $Na_2SO_4$ and concentrated to give 18 mg of a white solid. MS calculated for $C_{14}H_{18}INO$+H: 344, observed: 344.

Example 13

(R,S) 3,5-Dimethyl-6,7,8,9-tetrahydro-5H-1-oxa-7-aza-cycloheptaindene

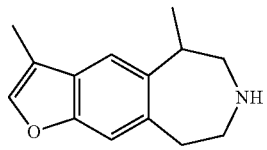 [SMILES: Cc1coc2cc3c(cc12)C(C)CNCC3]

N-trifluoroacetyl-3,5-dimethyl-6,7,8,9-tetrahydro-5H-1-oxa-7-aza-cycloheptaindene A solution of N-trifluoroacetyl-7-allyloxy-8-iodo-1-methyl-2,3,4,5-tetrahydro-1H-3-benzazepine (158 mg, 0.360 mmol) in dimethylformamide (4 mL) was treated with KOAc (106 mg, 1.08 mmol), n-Bu₄NBr (116 mg, 0.360 mmol), PPh₃ (13 mg, 0.036 mmol), Pd(OAc)₂ (4 mg, 0.018 mmol) and stirred overnight at 100° C. The product mixture was filtered, water (10 mL) added and then extracted twice with EtOAc (10 mL). The combined organic phases were washed with brine (10 mL), dried with $Na_2SO_4$ and concentrated. Flash chromatography (5% EtOAc in hexane, silica) resulted in 15 mg of a clear oil. MS calculated for $C_{16}H_{16}F_3NO_2$+H: 312, observed: 312.

3,5-Dimethyl-6,7,8,9-tetrahydro-5H-1-oxa-7-aza-cycloheptaindene

A solution of N-trifluoroacetyl-3,5-dimethyl-6,7,8,9-tetrahydro-5H-1-oxa-7-aza-cycloheptaindenecycloheptaindene (15 mg, 0.048 mmol) in methanol (2 mL) was treated with 15% aqueous NaOH (2 mL), and stirred overnight at 20° C. The product mixture was diluted with water (5 mL), extracted twice with EtOAc (5 mL), the combined organic phases were washed with brine (5 mL), dried with $Na_2SO_4$ and concentrated to give 10 mg of a white solid. ¹H NMR (400 MHz, CDCl₃) δ 7.25 (s, 1H), 7.12 (s, 1H), 7.09 (s, 1H), 3.12 (m, 1H), 2.97 (m, 4H), 2.85 (m, 1H), 2.64 (bm, 1H), 2.15 (s, 3H), 1.34 (d, J=8 Hz, 3H). MS calculated for $C_{14}H_{17}NO$+H: 216, observed: 216.

Example 14

(R,S) 7-Allyloxy-8-chloro-1-methyl-2,3,4,5-tetrahydro-1H-3-benzazepine

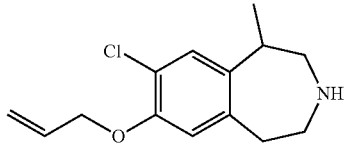 [SMILES: C=CCOc1cc2c(cc1Cl)C(C)CNCC2]

N-Trifluoroacetyl-8-chloro-7-hydroxy-1-methyl-2,3,4,5-tetrahydro-1H-3-benzazepine A solution of N-trifluoroacetyl-8-chloro-7-methoxy-1-methyl-2,3,4,5-tetrahydro-1H-3-benzazepine (48 mg, 0.15 mmol) in dichloromethane (2 mL) was treated with BBr₃ (0.30 mL of a 1.0M solution in $CH_2Cl_2$, 0.30 mmol) and stirred overnight at 20° C. The excess BBr₃ was quenched with water and the resulting mixture diluted with ether (20 mL), washed with $Na_2CO_3$ (10 mL) and brine (10 mL), dried with $Na_2SO_4$ and concentrated. Flash chromatography (15% EtOAc in hexane, silica) resulted in 24 mg of a white solid. MS calculated for $C_{13}H_{13}ClF_3NO_2$+H: 308, observed: 308.

N-Trifluoroacetyl-7-allyloxy-8-chloro-1-methyl-2,3,4,5-tetrahydro-1H-3-benzazepine A solution of N-trifluoroacetyl-8-chloro-7-hydroxy-1-methyl-2,3,4,5-tetrahydro-1H-3-benzazepine (24 mg, 0.078 mmol) in dichloromethane (2 mL) was treated with allyl bromide (18 mg, 0.15 mmol), DBU (23 mg, 0.15 mmol) and stirred 2 hours at 20° C. The product mixture was diluted with EtOAc (10 mL), washed with 5% aqueous HCl (5 mL), brine (5 mL), dried with $Na_2SO_4$ and concentrated. Flash chromatography (15% EtOAc in hexane, silica) resulted in 23 mg of a white solid. MS calculated for $C_{16}H_{17}ClF_3NO_2$+H: 348, observed: 348.

7-Allyloxy-8-chloro-1-methyl-2,3,4,5-tetrahydro-1H-3-benzazepine

A solution of N-trifluoroacetyl-7-allyloxy-8-chloro-1-methyl-2,3,4,5-tetrahydro-1H-3-benzazepine (23 mg, 0.066 mmol) in methanol (2 mL) was treated with 15% aqueous NaOH (2 mL), and stirred overnight at 20° C. The product mixture was diluted with water (5 mL), extracted twice with EtOAc (5 mL), the combined organic phases were washed with brine (5 mL), dried with $Na_2SO_4$ and concentrated to give 19 mg of a white solid. ¹H NMR (400 MHz, CD₃OD) δ 7.12 (s, 1H), 6.81 (s, 1H), 6.03 (m, 1H), 5.43 (d, J=17 Hz, 1H), 5.24 (d, J=10 Hz, 1H), 4.57 (d, J=5 Hz, 2H), 3.1-2.9 (m, 5H), 2.81 (m, 1H), 2.63 (m, 1H), 1.30 (d, J=7 Hz, 3H).

Example 15

(R,S) 7-Methoxy-1-methyl-8-(2-thienyl)-2,3,4,5-tetrahydro-1H-3-benzazepine

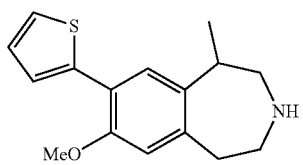 [SMILES: COc1cc2c(cc1-c1cccs1)C(C)CNCC2]

N-Trifluoroacetyl-7-methoxy-1-methyl-8-(2-thienyl)-2,3,4,5-tetrahydro-1H-3-benzazepine A solution of N-trifluoromethylacetyl-8-bromo-7-methoxy-1-methyl-1,2,4,5-tetrahydro-3H-3-benzazepine (51 mg, 0.14 mmol) in 1,4-dioxane (2 mL) was treated with thiophene-2-boronic acid (36 mg, 0.28 mmol), $K_2CO_3$ (58 mg, 0.42 mmol), water (0.1 mL), $Pd(PPh_3)_4$ (16 mg, 0.014 mmol) and stirred overnight at 100° C. The product mixture was diluted with EtOAc, filtered, absorbed on silica and purified by flash chromatograghy (10% EtOAc in hexane, silica) resulting in 28 mg of a yellow solid. MS calculated for $C_{18}H_{18}F_3NO_2S$+H: 370, observed: 370.

7-Methoxy-1-methyl-8-(2-thienyl)-2,3,4,5-tetrahydro-1H-3-benzazepine

A solution of N-trifluoroacetyl-7-methoxy-1-methyl-8-(2-thienyl)-2,3,4,5-tetrahydro-1H-3-benzazepine (28 mg, 0.076 mmol) in methanol (2 mL) was treated with 15% aqueous NaOH (2 mL), and stirred 0.5 hours at 50° C. The product mixture was diluted with water (5 mL), extracted twice with EtOAc (5 mL), the combined organic phases were washed with brine (5 mL), dried with $Na_2SO_4$ and concentrated to give 18 mg of a yellow oil. $^1$H NMR (400 MHz, $CDCl_3$) δ 7.45 (d, J=4 Hz, 1H), 7.39 (s, 1H), 7.27 (d, J=6 Hz, 1H), 7.07 (dd, J=4, 6 Hz, 1H), 6.71 (s, 1H), 3.90 (s, 3H), 3.1-2.9 (m, 6H), 2.80 (m, 1H), 2.22 (bs, 1H), 1.38 (d, J=7 Hz, 3H). MS calculated for $C_{16}H_{19}NOS$+H: 274, observed: 274.

Example 16

(R,S) 8-Cyano-7-methoxy-1-methyl-2,3,4,5-tetrahydro-1H-3-benzazepine

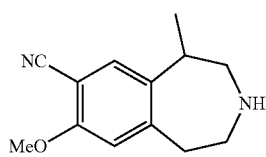

N-Trifluoroacetyl-8-cyano-7-methoxy-1-methyl-2,3,4,5-tetrahydro-1H-3-benzazepine A solution of N-trifluoroacetyl-8-bromo-7-methoxy-1-methyl-2,3,4,5-tetrahydro-1H-3-benzazepine (18 mg, 0.05 mmol) in dimethylformamide (1 mL) was treated with CuCN (20 mg, 0.24 mmol) and the mixture was microwaved at 200° C. for 0.5 hours. The product mixture was diluted with water (5 mL), extracted twice with EtOAc (5 mL), the combined organic phases were washed with brine (5 mL), dried with $Na_2SO_4$ and concentrated. Flash chromatography (35% EtOAc in hexane, silica) resulted in 10 mg of a clear oil. MS calculated for $C_{15}H_{15}F_3N_2O_2$+H: 313, observed: 313.

8-Cyano-7-methoxy-1-methyl-2,3,4,5-tetrahydro-1H-3-benzazepine

A solution of N-trifluoroacetyl-8-cyano-7-methoxy-1-methyl-2,3,4,5-tetrahydro-1H-3-benzazepine (10 mg, 0.032 mmol) in methanol (2 mL) was treated with 15% aqueous NaOH (2 mL), and stirred 1 hour at 50° C. The product mixture was diluted with water (5 mL), extracted twice with EtOAc (5 mL), the combined organic phases were washed with brine (5 mL), dried with $Na_2SO_4$ and concentrated to give 6.0 mg of a white solid. $^1$H NMR (400 MHz, $CD_3OD$) δ 7.33 (s, 1H), 6.93 (s, 1H), 3.91 (s, 3H), 3.18-2.97 (m, 5H), 2.80 (m, 1H), 2.60 (m, 1H), 1.33 (d, J=8 Hz, 3H). MS calculated for $C_{13}H_{16}N_2O$+H: 217, observed: 217.

Example 17

(R,S) 8-bromo-1-cyclopropyl-7-methoxy-2,3,4,5-tetrahydro-1H-3-benzazepine

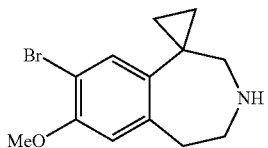 [SMILES: COc1cc2c(cc1Br)C1(CC1)CNCC2]

N-Trifluoroacetyl-1-cyclopropyl-7-methoxy-2,3,4,5-tetrahydro-1H-3-benzazepine A solution of diethyl zinc (1 mL, 1 M in hexanes) in dichloromethane (1 mL) at 0° C. was treated with trifluoroacetic acid in dichloromethane (0.5 mL) and the mixture stirred for 15 min. Diiodomethane (0.280 g, 1.0 mmol) in dichloromethane (0.5 mL) was then added and stirred for 15 minutes. N-Trifluoroacetyl-7-methoxy-1-methylene-2,3,4,5-tetrahydro-1H-3-benzazepine (0.075 g, 0.26 mmol) in dichloromethane (1 mL) was added and the mixture stirred for 30 minutes at 0° C. and then for 2 hours at 20° C. The product mixture was quenched with aqueous saturated $NH_4Cl$ (5 mL), extracted twice with $CH_2Cl_2$ (20 mL), washed with saturated aqueous $NaHCO_3$ (10 mL), washed with $H_2O$ (10 mL), and concentrated. Flash chromatography (7% EtOAc in hexanes, silica) resulted in 0.050 g of a white solid. MS calculated for $C_{15}H_{16}F_3NO_2$+H: 300, observed: 300.

N-Trifluoroacetyl-8-bromo-1-cyclopropyl-7-methoxy-2,3,4,5-tetrahydro-1H-3-benzazepine A solution of N-trifluoroacetyl-1-cyclopropyl-7-methoxy-2,3,4,5-tetrahydro-1H-3-benzazepine (0.025 g, 0.08 mmol) in acetonitrile (1 mL) was treated with N-bromosuccinimide (0.032 g, 0.18 mmol) and stirred for 2 hrs. at 50° C. The product mixture was concentrated and then purified by flash chromatography (10% EtOAc in hexanes, silica) resulting in 0.014 g of a white solid. MS calculated for $C_{15}H_{15}BrF_3NO_2$+H: 378, observed: 378.

8-bromo-1-cyclopropyl-7-methoxy-2,3,4,5-tetrahydro-1H-3-benzazepine

A solution of N-trifluoroacetyl-8-bromo-1-cyclopropyl-7-methoxy-2,34,5-tetrahydro-1H-3-benzazepine (0.014 g, 0.037 mmol) in methanol (1 mL) was treated with 15% aqueous NaOH (1 mL), and stirred for 2 hours at 50° C. The product mixture was diluted with brine (10 mL), extracted twice with EtOAc (10 mL), dried with MgSO$_4$, and concentrated to give 0.008 g of a clear oil. $^1$H NMR (400 MHz, CD$_3$OD) δ 7.26 (s, 1H), 6.78 (s, 1H), 3.83 (s, 3H), 3.02 (m, 2H), 2.92 (m, 2H), 2.67 (s, 2H), 0.91 (m, 2H), 0.85 (m, 2H). MS calculated for C$_{13}$H$_{16}$BrNO+H: 282, observed: 282.

Example 18

(R,S) 8-bromo-1-hydroxymethyl-7-methoxy-2,3,4,5-tetrahydro-1H-3-benzazepine

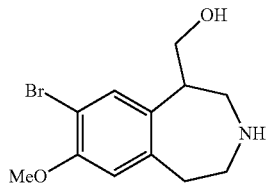 [SMILES: COc1cc2c(cc1Br)C(CO)CNCC2]

N-Trifluoroacetyl-1-hydroxymethyl-7-methoxy-2,3,4,5-tetrahydro-1H-3-benzazepine A solution of N-trifluoroacetyl-7-methoxy-1-methylene-2,3,4,5-tetrahydro-1H-3-benzazepine (0.100 g, 0.35 mmol) in tetrahydrofuran (1 mL) was treated with BH$_3$-THF complex (0.36 mL, 1M in THF), and stirred for 30 min. at 20° C. Water (0.5 mL), saturated aqueous NaHCO$_3$ (0.5 mL), and 30% H$_2$O$_2$ (0.2 mL) were added sequentially and the reaction stirred for 30 min. at 20° C. The product mixture was diluted with EtOAc (10 mL), washed with brine (10 mL), and concentrated. Flash chromatography (33% EtOAc in hexane, silica) resulted in 0.035 g of a clear oil. MS calculated for C$_{14}$H$_{16}$F$_3$NO$_3$+H: 304, observed: 304.

N-Trifluoroacetyl-8-bromo-1-hydroxymethyl-7-methoxy-2,3,4,5-tetrahydro-1H-3-benzazepine A solution of N-trifluoromethylacetyl-1-hydroxymethyl-7-methoxy-2,3,4,5-tetrahydro-1H-3-benzazepine (0.035 g, 0.12 mmol) in acetonitrile (1 mL) was treated with N-bromosuccinimide (0.025 g, 0.14 mmol), and stirred for 30 min. at 20° C. The product mixture was concentrated and then purified by flash chromatography (33% EtOAc in hexane, silica) resulting in 0.019 g clear oil. MS calculated for C$_{14}$H$_{15}$BrF$_3$NO$_3$+H: 382, observed: 382.

8-bromo-1-hydroxymethyl-7-methoxy-2,3,4,5-tetrahydro-1H-3-benzazepine

A solution of N-trifluoroacetyl-8-bromo-1-hydroxymethyl-7-methoxy-2,3,4,5-tetrahydro-1H-3-benzazepine (0.009 g, 0.024 mmol) in methanol (1 mL) was treated with 15% aqueous NaOH (1 mL), and stirred for 1 hour at 50° C. The product mixture was diluted with brine (5 mL), extracted twice with EtOAc (5 mL), dried with MgSO$_4$, and concentrated to give 0.006 g clear oil. $^1$H NMR (400 MHz, CD$_3$OD) δ 7.28 (s, 1H), 6.79 (s, 1H), 3.84 (m, 2H), 3.0-2.8 (m, 7H). MS calculated for C$_{12}$H$_{16}$BrNO$_2$+H: 286, observed: 286.

Example 19

(R,S) 8-Bromo-1-ethyl-7-methoxy-2,3,4,5-tetrahydro-1H-3-benzazepine

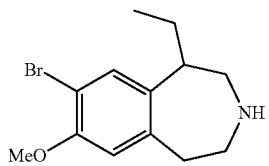 [SMILES: CCC1CNCCc2cc(OC)c(Br)cc21]

N-Crotyl, N-trifluoroacetyl-2-iodo-5-methoxyphenethylamine

A solution of N-trifluoroacetyl-2-iodo-5-methoxyphenethylamine (6.68 g, 17.9 mmol) in toluene (100 mL) was treated with K$_2$CO$_3$ (3.22 g, 23.3 mmol), KOH (3.01 g, 53.7 mmol), n-Bu$_4$NBr (0.580 g, 1.80 mmol) and crotyl bromide (3.15 g, 23.3 mmol). The mixture was stirred at 75° C. for 16 hours, cooled to 20° C., diluted with Et$_2$O (500 mL), washed with 10% aqueous HCl (500 mL) and concentrated. Flash chromatography (10% EtOAc in hexane, silica) resulted in 5.22 g of a clear oil. MS calculated for C$_{15}$H$_{17}$F$_{31}$NO$_2$+H: 428, observed: 428.

N-Trifluoroacetyl-1-ethylene-7-methoxy-2,3,4,5-tetrahydro-1H-3-benzazepine

A solution of N-crotyl, N-trifluoroacetyl-2-iodo-5-methoxyphenethylamine (5.20 g, 12.2 mmol) in dimethylformamide (80 mL) was treated with KOAc (3.59 g, 36.6 mmol), n-Bu$_4$NBr (3.93 g, 12.2 mmol), PPh$_3$ (0.320 g, 1.22 mmol), Pd(OAc)$_2$ (0.137 g, 0.61 mmol) and stirred overnight at 90° C. The product mixture was cooled to 20° C., diluted with water (200 mL), extracted twice with ether (500 mL), the combined organic phases washed twice with brine (200 mL), and concentrated. Flash chromatography (10% EtOAc in hexane, silica) resulted in 2.29 g of a clear oil, which consists of a mixture of olefinic isomers. MS calculated for C$_{15}$H$_{16}$F$_3$NO$_2$+H: 300, observed: 300.

N-Trifluoroacetyl-1-ethyl-7-methoxy-2,3,4,5-tetrahydro-1H-3-benzazepine

A solution of N-trifluoroacetyl-1-ethylene-7-methoxy-2,3,4,5-tetrahydro-1H-3-benzazepine (2.29 g, 7.65 mmol) in methanol (100 mL) was treated with 10% Pd/C (4.0 g, 0.77 mmol)) and stirred overnight under an atmosphere of hydrogen. The product mixture was filtered through a pad of celite and silica, and the solvent removed to give 2.14 g of a clear oil. MS calculated for C$_{15}$H$_{18}$F$_3$NO$_2$+H: 302, observed: 302.

N-Trifluoroacetyl-8-bromo-1-ethyl-7-methoxy-2,3,4,5-tetrahydro-1H-3-benzazepine A solution of N-trifluorolacetyl-1-ethyl-7-methoxy-2,3,4,5-tetrahydro-1H-3-benzazepine (0.710 g, 2.36 mmol) in acetonitrile (20 mL) was treated with N-bromosuccinimide (0.504 g, 2.83 mmol), and stirred overnight at 20° C. The product mixture was concentrated, diluted with EtOAc (100 mL), washed with water (50 mL) and brine (50 mL), dried with Na₂SO₄ and concentrated. Flash chromatography (10% EtOAc in hexanes, silica) resulted in 0.561 g of a clear oil. MS calculated for $C_{15}H_{17}BrF_3NO_2$+H: 380, observed: 380.

8-Bromo-1-ethyl-7-methoxy-2,3,4,5-tetrahydro-1H-3-benzazepine

A solution of N-trifluoroacetyl-8-bromo-1-ethyl-7-methoxy-2,3,4,5-tetrahydro-1H-3-benzazepine (0.561 g, 1.48 mmol) in methanol (30 mL) was treated with 15% aqueous NaOH (30 mL), and stirred overnight at 20° C. The product mixture was diluted with brine (100 mL), extracted twice with EtOAc (200 mL), dried with MgSO₄, and concentrated to give 0.412 g of a clear oil. ¹H NMR (400 MHz, CD₃OD) δ 7.24 (s, 1H), 6.76 (s, 1H), 3.83 (s, 3H), 3.02 (m, 3H), 2.91 (s, 1H), 2.85-2.76 (m, 3H), 2.63 (m, 1H), 1.78 (m, 1H), 1.72 (m, 1H), 0.94 (dd, J=8, 8 Hz, 3H). MS calculated for $C_{13}H_{18}BrNO$+H: 284, observed: 284.

Example 20

(R,S) 8-Chloro-1-ethyl-7-methoxy-2,3,4,5-tetrahydro-1H-3-benzazepine

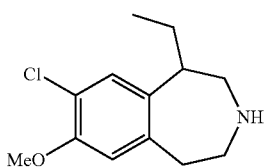 [SMILES: CCC1CNCCc2cc(OC)c(Cl)cc21]

N-Trifluoroacetyl-8-chloro-1-ethyl-7-methoxy-2,3,4,5-tetrahydro-1H-3-benzazepine A solution of N-trifluorolacetyl-1-ethyl-7-methoxy-2,3,4,5-tetrahydro-1H-3-benzazepine (0.600 g, 1.99 mmol) in acetonitrile (20 mL) was treated with N-chlorosuccinimide (0.057 g, 0.32 mmol), and stirred overnight at 60° C. The product mixture was concentrated, diluted with EtOAc (100 mL), washed with water (50 mL) and brine (50 mL), dried with Na₂SO₄ and concentrated. Flash chromatography (10% EtOAc in hexanes, silica) resulted in 0.421 g of a clear oil. MS calculated for $C_{15}H_{17}ClF_3NO_2$+H: 336, observed: 336.

8-Chloro-1-ethyl-7-methoxy-2,3,4,5-tetrahydro-1H-3-benzazepine

A solution of N-trifluoroacetyl-8-chloro-1-ethyl-7-methoxy-2,3,4,5-tetrahydro-1H-3-benzazepine (0.421 g, 1.25 mmol) in methanol (30 mL) was treated with 15% aqueous NaOH (30 mL), and stirred overnight at 20° C. The product mixture was diluted with brine (100 mL), extracted twice with EtOAc (200 mL), dried with MgSO₄, and concentrated to give 0.241 g of a clear oil. ¹H NMR (400 MHz, CD₃OD) δ 7.05 (s, 1H), 6.79 (s, 1H), 3.84 (s, 3H), 3.03 (m, 3H), 2.91 (s, 1H), 2.86-2.76 (m, 3H), 2.64 (m, 1H), 1.81 (m, 1H), 1.72 (m, 1H), 0.93 (dd, J=8, 8 Hz, 3H). MS calculated for $C_{13}H_{18}ClNO$+H: 240, observed: 240.

Example 21

(R,S) 8-Bromo-1-isopropyl-7-methoxy-2,3,4,5-tetrahydro-1H-3-benzazepine

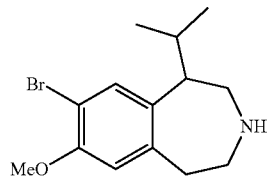 [SMILES: COc1cc2c(cc1Br)C(C(C)C)CNCC2]

N-(3-methylbut-2-enyl), N-trifluoroacetyl-2-iodo-5-methoxyphenethylamine

A solution of N-trifluoroacetyl-2-iodo-5-methoxyphenethylamine (0.700 g, 1.88 mmol) in toluene (25 mL) was treated with K₂CO₃ (0.340 g, 2.4 mmol), KOH (0.210 g, 3.76 mmol), n-Bu₄NBr (0.060 g, 0.19 mmol) and 4-bromo-2-methyl-2-butene (0.364 g, 2.44 mmol). The mixture was stirred at 80° C. for 3 hours, cooled to 20° C., diluted with ether (100 mL), washed with 10% HCl (50 mL) and concentrated. Flash chromatography (10% EtOAc in hexane, silica) resulted in 0.272 g of a clear oil. ¹H NMR (400 MHz, CDCl₃, mixture of rotamers) δ 7.65 (m, 1H), 6.75 (m, 1H), 6.54 (m, 1H), 5.20 (m, 4H), 5.0 (m, 6H), 4.10 (m, 1H), 3.82 (m, 1H), 3.76 (d, 2H), 3.50 (m, 2H), 3.02 (m, 2H), 1.75 (m, 3H), 1.66 (m, 3H).

N-Trifluoroacetyl-1-isopropylene-7-methoxy-2,3,4,5-tetrahydro-1H-3-benzazepine A solution of N-(3-methylbut-2-enyl), N-trifluoroacetyl-2-iodo-5-methoxyphenethylamine (0.0272 g, 0.62 mmol) in dimethylformamide (12 mL) was treated with KOAc (0.183 g, 1.86 mmol), n-Bu₄NBr (0.200 g, 0.062 mmol), PPh₃ (0.016 g, 0.062 mmol), Pd(OAc)₂ (0.183 g, 1.86 mmol) and stirred overnight at 90° C. The product mixture was cooled to 20° C., diluted with water (50 mL), extracted twice with ether (50 mL), the combined organic phases were washed with brine (50 mL), and concentrated. Flash chromatography (10% EtOAc in hexane, silica) resulted in 0.096 g of a clear oil. MS calculated for $C_{16}H_{15}F_3NO_2$+H: 314, observed: 314.

N-Trifluoroacetyl-1-isopropyl-7-methoxy-2,3,4,5-tetrahydro-1H-3-benzazepine

A solution of N-trifluoroacetyl-1-isopropylene-7-methoxy-2,3,4,5-tetrahydro-1H-3-benzazepine (0.096 g, 0.31 mmol) in ethanol (2 mL) was treated with 10% Pd/C (0.033 g, 0.031 mmol)) and stirred overnight under an atmosphere of hydrogen. The product mixture was filtered through a pad of celite and silica, and the solvent removed to give 0.091 g of a clear oil. MS calculated for $C_{16}H_{20}F_3NO_2$+H: 316, observed: 316.

N-Trifluoroacetyl-8-bromo-1-isopropyl-7-methoxy-2,3,4,5-tetrahydro-1H-3-benzazepine A solution of N-trifluorolacetyl-1-isopropyl-7-methoxy-2,3,4,5-tetrahydro-1H-3-benzazepine (0.091 g, 0.29 mmol) in acetonitrile (3 mL) was treated with N-bromosuccinimide (0.057 g, 0.32 mmol), and stirred overnight at 20° C. After removing the solvent, flash chromatography (10% EtOAc in hexanes, silica) resulted in 0.056 g of a clear oil. MS calculated for $C_{16}H_{19}BrF_3NO_2$+H: 394, observed: 394.

8-Bromo-1-isopropyl-7-methoxy-2,3,4,5-tetrahydro-1H-3-benzazepine

A solution of N-trifluoroacetyl-8-bromo-1-isopropyl-7-methoxy-2,3,4,5-tetrahydro-1H-3-benzazepine (0.013 g, 0.03 mmol) methanol (0.5 mL) was treated with 15% aqueous NaOH (0.5 mL), and stirred overnight at 20° C. The product mixture was diluted with brine (5 mL), extracted twice with EtOAc (5 mL), dried with MgSO$_4$, and concentrated to give 0.10 g of a clear oil. $^1$H NMR (400 MHz, CD$_3$OD) δ 7.08 (s, 1H), 6.64 (s, 1H), 3.72 (s, 3H), 3.2-3.10 (m, 3H), 2.7-2.5 (m, 3H), 2.3-2.1 (m, 2H), 0.96 (d, 3H), 0.63 (d, 3H). MS calculated for $C_{14}H_{20}BrNO$+H: 298, observed: 298.

Example 22

(R,S) 8-Bromo-7-hydroxy-1-isopropyl-2,3,4,5-tetrahydro-1H-3-benzazepine

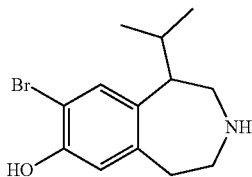 [SMILES: CC(C)C1CNCCc2cc(O)c(Br)cc21]

N-Trifluoroacetyl-8-bromo-7-hydroxy-1-isopropyl-2,3,4,5-tetrahydro-1H-3-benzazepine A solution of N-trifluoroacetyl-8-bromo-1-isopropyl-7-methoxy-2,3,4,5-tetrahydro-1H-3-benzazepine (0.041 g, 0.10 mmol) in dichloromethane (1 mL) was treated with BBr$_3$ (0.32 ml, 1.0 M solution in CH$_2$Cl$_2$) and stirred overnight at 20° C. The excess BBr$_3$ is quenched with water and the resulting mixture diluted with ether (50 mL), washed twice with saturated aqueous Na$_2$CO$_3$ (20 mL) and concentrated. Flash chromatography (20% EtOAc in hexanes, silica) resulted in 0.037 g clear oil. MS calculated for $C_{15}H_{17}BrF_3NO_2$+H: 380, observed: 380.

8-Bromo-7-hydroxy-1-isopropyl-2,3,4,5-tetrahydro-1H-3-benzazepine

A solution of N-trifluoroacetyl-8-bromo-7-hydroxy-1-isopropyl-2,3,4,5-tetrahydro-1H-3-benzazepine (0.018 g, 0.047 mmol) in methanol (1 mL) was treated with 15% aqueous NaOH (1 mL), and stirred for 3 hours at 50° C. The product mixture was brought to pH 7-8 with 10% aqueous HCl, extracted three times with EtOAc (50 mL), dried with MgSO$_4$, and concentrated to give 0.013 g of a white solid. $^1$H NMR (400 MHz, CD$_3$OD) δ 7.10 (s, 1H), 6.60 (s, 1H), 3.30 (m, 1H), 3.2-3.0 (m, 2H), 2.78 (m, 1H), 2.7-2.5 (m, 2H), 2.3-2.1 (m, 2H), 1.05 (d, 3H), 0.73 (d, 3H). MS calculated for $C_{13}H_{18}BrNO$+H: 284, observed: 284.

Example 23

(R,S) 7-Allyloxy-8-bromo-1-isopropyl-2,3,4,5-tetrahydro-1H-3-benzazepine

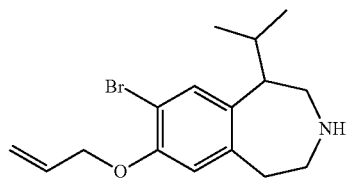 [SMILES: C=CCOc1cc2c(cc1Br)C(C(C)C)CNCC2]

N-Trifluoroacetyl-7-allyloxy-8-bromo-1-isopropyl-2,3,4,5-tetrahydro-1H-3-benzazepine A solution of N-trifluoroacetyl-8-bromo-7-hydroxy-1-isopropyl-2,3,4,5-tetrahydro-1H-3-benzazepine (0.017 g, 0.045 mmol) in dichloromethane (1 mL) was treated with N'''-tert-butyl-N,N,N',N',N'',N''-hexamethylphosphorimidic triamide (0.016 g, 0.068 mmol), allyl bromide (0.011 g, 0.09 mmol) and stirred for 3 hours at 20° C. The product mixture was diluted with 10% aqueous HCl, extracted twice with dichloromethane (20 mL), and concentrated. Flash chromatography (10% EtOAc in hexanes, silica) resulted in 0.011 g of a clear oil. MS calculated for $C_{18}H_{21}BrF_3NO_2$+H: 420, observed: 420.

7-Allyloxy-8-bromo-1-isopropyl-2,3,4,5-tetrahydro-1H-3-benzazepine

A solution of N-trifluoroacetyl-7-allyloxy-8-bromo-1-isopropyl-2,3,4,5-tetrahydro-1H-3-benzazepine (0.011 g, 0.026 mmol) in methanol (0.5 mL) was treated with of 15% aqueous NaOH (0.5 mL), and stirred for 3 hours at 50° C. The product mixture was diluted with brine (5 mL), extracted twice with EtOAc (5 mL), dried with MgSO$_4$, and concentrated to give 0.010 g of a clear oil. $^1$H NMR (400 MHz, CD$_3$OD) 7.09 (s, 1H), 6.62 (s, 1H), 5.94 (m, 1H), 5.32 (dd, 1H), 5.12 (dd, 1H), 4.46 (d, 2H), 3.19 (m, 1H), 3.05 (m, 2H), 2.66 (m, 1H), 2.5 (bm, 2H), 2.3-2.1 (m, 2H), 0.95 (d, 3H), 0.63 (d, 3H). MS calculated for $C_{16}H_{22}BrNO$+H: 324, observed: 324.

Example 24

8-Bromo-7-methoxy-1,4-dimethyl-2,3,4,5-tetrahydro-1H-3-benzazepine

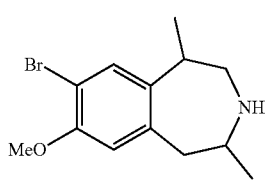 [SMILES: COc1cc2c(cc1Br)C(C)CNC(C)C2]

N-Trifluoroacetyl-1-(3-methoxyphenyl)-2-propylamine

A solution of 1-(3-methoxyphenyl)-2-propylamine (3.59 g, 21.7 mmol) in dichloromethane (75 mL) at 0° C., was treated with pyridine (2.1 mL, 28.2 mmol), trifluoracetic anhydride (5.9 g, 28.2 mmol), and then stirred for 3 hours while warming to 20° C. The product mixture was diluted with EtOAc (300 mL), washed sequentially with 10% aqueous HCl (100 mL), water (100 mL), brine (100 mL), dried with $Na_2SO_4$ and concentrated. Flash chromatography (20% EtOAc in hexane, silica) resulted in 4.29 g of a yellow solid. $^1$H NMR (400 MHz, $CD_3OD$) δ 7.17 (dd, J=8, 8 Hz, 1H), 6.76 (m, 3H), 4.19 (m, 1H), 3.77 (s, 3H), 2.78 (m, 2H), 1.21 (d, J=7 Hz, 2H).

N-Trifluoroacetyl-1-(2-iodo-5-methoxyphenyl)-2-propylamine

A solution of N-trifluoroacetyl-1-(3-methoxyphenyl)-2-propylamine (4.29 g, 15.7 mmol) in methanol (100 mL) was cooled to −78° C. and treated with $CaCO_3$ (3.17 g, 31.4 mmol), followed by a solution of ICl (6.37 g, 39.3 mmol) in methanol (50 mL). The reaction was allowed to warm to 20° C. while stirring overnight. The product mixture was filtered, concentrated, dissolved in EtOAc (200 mL), washed twice with 5% aqueous sodium bisulfite (100 mL), once with brine (100 mL), dried with $Na_2SO_4$ and concentrated to give 6.72 g of a white solid powder. MS calculated for $C_{12}H_{13}F_3INO_2$+H: 388, observed: 388.

N-Allyl, N-trifluoroacetyl-1-(2-iodo-5-methoxyphenyl)-2-propylamine

A solution of N-trifluoroacetyl-1-(2-iodo-5-methoxyphenyl)-2-propylamine (6.09 g, 15.7 mmol) in toluene (450 mL) was treated with $K_2CO_3$ (2.82 g, 20.4 mmol), KOH (2.45 g, 47.1 mmol), n-$Bu_4$NBr (0.506 g, 1.57 mmol) and allyl bromide (2.47 g, 20.4 mmol), and stirred overnight at 80° C. The product mixture was acidified with 10% aqueous HCl, separated, the aqueous phase extracted with ether (500 mL), the combined organic phases were washed with brine (200 mL), dried with $Na_2SO_4$ and concentrated to give 4.45 g of a brown oil.

N-Trifluoroacetyl-7-methoxy-4-methyl-1-methylene-2,3,4,5-tetrahydro-1H-3-benzazepine A solution of N-allyl, N-trifluoroacetyl-1-(2-iodo-5-methoxyphenyl)-2-propylamine (4.45 g, 10.8 mmol) in dimethylformamide (120 mL) was treated with KOAc (3.17 g, 32.3 mmol), n-$Bu_4$NBr (3.47 g, 10.8 mmol), $PPh_3$ (0.283 g, 1.08 mmol), $Pd(OAc)_2$ (0.242 g, 1.08 mmol) and stirred overnight at 80° C. The product mixture was cooled to 20° C., filtered, diluted with water (200 mL), extracted with ether (3×200 mL), the combined organic phases washed with water (100 mL), brine (100 mL), dried with $Na_2SO_4$ and concentrated. Flash chromatography (10% EtOAc in hexane, silica) resulted in 1.39 g of a yellow oil.

N-Trifluoroacetyl-1,4-dimethyl-7-methoxy-2,3,4,5-tetrahydro-1H-3-benzazepine

A solution of N-trifluoroacetyl-7-methoxy-4-methyl-1-methylene-2,3,4,5-tetrahydro-1H-3-benzazepine (1.39 g, 4.64 mmol) in ethanol (40 mL) was treated with 10% Pd/C (0.49 g, 0.46 mmol) and stirred overnight under an atmosphere of hydrogen. The product mixture was filtered through a pad of celite and silica and then concentrated. Flash chromatography (20% EtOAc in hexane, silica) resulted in 0.77 g of a clear oil. $^1$H NMR (400 MHz, $CDCl_3$, mixture of rotamers) δ 7.06 (m, 1H), 6.71 (m, 1H), 6.63 (m, 1H), 4.38 (bm, 1H), 3.8 (s, 3H), 3.6 (m, 1H), 3.25 (m, 1H), 3.18 (bm, 2H), 2.72 (m, 1H), 1.34 (m, 3H) 1.22 (m, 3H).

N-Trifluoroacetyl-8-bromo-1,4-dimethyl-7-methoxy-2,3,4,5-tetrahydro-1H-3-benzazepine A solution N-trifluoroacetyl-1,4-dimethyl-7-methoxy-2,3,4,5-tetrahydro-1H-3-benzazepine (0.452 g, 1.50 mmol) in acetonitrile (20 mL) was treated with N-bromosuccinimide (0.294 g, 1.65 mmol) and stirred overnight at 20° C. The product mixture was diluted with EtOAc (100 mL), washed with sodium bisulfite (50 mL) and brine (50 mL), dried with $Na_2SO_4$ and concentrated. Flash chromatography (20% EtOAc in hexane, silica) resulted in a clear oil. $^1$H NMR (400 MHz, $CDCl_3$, mixture of rotamers) δ 7.32 (s, 1H), 6.62 (m, 1H), 4.37 (m, 1H), 3.87 (s, 3H), 3.81 (m, 1H), 3.28-3.10 (m, 3H), 2.73 (m, 1H), 1.31 (m, 3H), 1.25 (m, 3H).

8-Bromo-1,4-dimethyl-7-methoxy-2,3,4,5-tetrahydro-1H-3-benzazepine

A solution of N-trifluoroacetyl-8-bromo-1,4-dimethyl-7-methoxy-2,3,4,5-tetrahydro-1H-3-benzazepine (21 mg, 0.055 mmol) in methanol (2 mL) was treated with 15% aqueous NaOH (2 mL), and stirred overnight at 20° C. The product mixture was diluted with water (5 mL), extracted twice with EtOAc (10 mL), the combined organic phases were washed with brine (10 mL), dried with $Na_2SO_4$ and concentrated to give 11 mg of a clear oil. $^1$H NMR (400 MHz, $CDCl_3$) δ 7.29 (s, 1H), 6.64 (s, 1H), 3.88 (s, 3H), 3.02 (m, 2H), 2.89 (dd, J=9, 14 Hz, 1H), 2.80 (m, 1H), 2.67 (d, J=14 Hz, 1H), 2.53 (dd, J=10, 13, 1H) 1.30 (d, J=7 Hz, 3H), 1.19 (d, J=6 Hz, 3H). MS calculated for $C_{13}H_{18}$BrNO+H: 284, observed: 284.

Example 25

7-Allyloxy-8-bromo-1,4-dimethyl-2,3,4,5-tetrahydro-1H-3-benzazepine

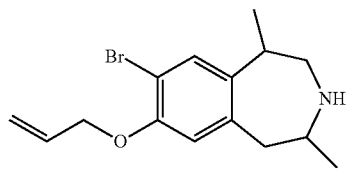 [SMILES: C=CCOc1cc2c(cc1Br)C(C)CNC(C)C2]

N-Trifluoroacetyl-8-bromo-1,4-dimethyl-7-hydroxy-2,3,4,5-tetrahydro-1H-3-benzazepine A solution of N-trifluoroacetyl-8-bromo-1,4-dimethyl-7-methoxy-2,3,4,5-tetrahydro-1H-3-benzazepine (0.383 g, 1.01 mmol) in dichloromethane (30 mL) was treated with $BBr_3$ (2.35 mL of a 1.0M solution in $CH_2Cl_2$, 2.35 mmol) and stirred overnight while warming to 20° C. The excess $BBr_3$ is quenched with water, and the resulting mixture was diluted with ether (100 mL), washed with saturated aqueous $Na_2CO_3$ (50 mL) and brine (50 mL), dried with $Na_2SO_4$ and concentrated. Flash chromatography (15% EtOAc in hexane, silica) resulted in 0.302 g of a white solid. $^1$H NMR (400 MHz, $CDCl_3$, mixture of rotamers) δ 7.22 (m, 1H), 6.77 (m, 1H), 5.34 (s, 1H), 4.35 (m, 1H), 3.62 (m, 1H), 3.24 (m, 1H), 3.13 (m, 2H), 2.69 (m, 1H), 1.31 (m, 3H), 1.22 (m, 3H).

N-Trifluoroacetyl-7-allyloxy-8-bromo-1,4-dimethyl-2,3,4,5-tetrahydro-1H-3-benzazepine A solution N-trifluoroacetyl-8-bromo-1,4-dimethyl-7-hydroxy-2,3,4,5-tetrahydro-1H-3-benzazepine (0.030 g, 0.082 mmol) in dichloromethane (2 mL) was treated with allyl bromide (0.030 g, 0.246 mmol), DBU (0.037 g, 0.246 mmol) and stirred 2 hours at 20° C. The product mixture was diluted with EtOAc (10 mL), washed with 5% aqueous HCl (2 mL), brine (5 mL), dried with $Na_2SO_4$ and concentrated. Flash chromatography (15% EtOAc in hexane, silica) resulted In 0.028 g of a clear oil. $^1$H NMR (400 MHz, $CDCl_3$, mixture of rotamers) δ 7.32 (s, 1H), 6.62 (m, 1H), 6.02 (m, 1H), 5.45 (d, J=17 Hz, 1H), 5.30 (d, J=11 Hz, 1H), 4.58 (s, 2H), 4.36 (m, 1H), 3.62 (m, 1H), 3.23 (m, 1H), 3.11 (m, 1H), 2.81 (d, J=10 Hz, 1H), 2.70 (m, 1H), 1.34 (m, 3H), 1.21 (m, 3H).

7-Allyloxy-8-bromo-1,4-dimethyl-2,3,4,5-tetrahydro-1H-3-benzazepine

A solution of N-trifluoroacetyl-7-allyloxy-8-bromo-1,4-dimethyl-2,3,4,5-tetrahydro-1H-3-benzazepine (0.028 g, 0.069 mmol) in methanol (2 mL) was treated with 15% aqueous NaOH (2 mL), and stirred for 3 hours at 20° C. The product mixture was diluted with water (10 mL), extracted twice with EtOAc (10 mL), the combined organic phases were washed with brine (10 mL), dried with $Na_2SO_4$ and concentrated to give 0.020 g of a clear oil. $^1$H NMR (400 MHz, $CDCl_3$) δ 7.30 (s, 1H), 6.64 (s, 1H), 6.06 (m, 1H), 5.47 (d, J=17 Hz, 1H), 5.30 (d, J=11 Hz, 1H), 4.56 (s, 2H), 3.03 (m, 2H), 2.90 (dd, J=9, 14 Hz, 1H), 2.80 (m, 1H), 2.65 (d, J=14 Hz, 1H), 2.55 (dd, J=10, 14 Hz, 1H), 1.77 (bs, 1H), 1.30 (d, J=7 Hz, 3H), 1.20 (d, J=6 Hz, 3H).

Example 26

(R,S) 8-Chloro-1-methyl-2,3,4,5-tetrahydro-9H-3-benzazepine

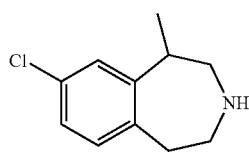

N-Trifluoroacetyl-4-chlorophenethylamine

A solution of 4-chlorophenethylamine (1.0 g, 6.4 mmol) in dichloromethane (20 mL) was cooled to 0° C., treated with pyridine (1.0 mL, 12.8 mmol), trifluoracetic anhydride (1.6 g, 7.7 mmol) and then stirred for 1 hour while warming to 20° C. The product mixture was diluted with EtOAc (100 mL), washed sequentially with 10% aqueous HCl (50 mL), water (50 mL), brine (50 mL), dried with $Na_2SO_4$ and concentrated to give 1.6 g of a white solid.

N-Trifluoroacetyl-2-iodo-4-chlorophenethylamine

A solution of N-trifluoroacetyl-4-chlorophenethylamine (1.6 g, 6.4 mmol) in dichloromethane (20 mL) was treated with bis(pyridine)iodonium(I)tetrafluoroborate (2.6 g, 7.0 mmol), $CF_3SO_3H$ (2.1 g, 14.1 mmol) and stirred overnight at 20° C. The product mixture was concentrated, dissolved in EtOAc (100 mL), washed twice with 5% aqueous sodium bisulfite (50 mL), twice with saturated aqueous $NaHCO_3$, (50 mL) once with brine (50 mL), dried with $Na_2SO_4$ and concentrated to give 0.94 g of a clear oil. MS calculated for $C_{10}H_8ClF_3INO+H$: 378, observed: 378.

N-Allyl, N-trifluoroacetyl-2-iodo-4-chlorophenethylamine

A solution of N-trifluoroacetyl-2-iodo-4-chlorophenethylamine (0.94 g, 2.4 mmol) in toluene (25 mL) was treated with $K_2CO_3$ (0.43 g, 3.12 mmol), KOH (0.40 g, 7.2 mmol), n-$Bu_4NBr$ (0.077 g, 0.24 mmol) and allyl bromide (0.43 g, 3.6 mmol) sequentially. The mixture was stirred at 80° C. for 3.5 hours, cooled to 20° C. and acidified with 10% aqueous HCl. The phases were separated, the aqueous phase extracted with ether (100 mL), the combined organic phases were washed with brine (50 mL), dried with $Na_2SO_4$ and concentrated to give 0.76 g of a clear oil. MS calculated for $C_{13}H_{12}ClF_3INO+H$: 418, observed: 418.

N-Trifluoroacetyl-8-chloro-1-methylene-2,3,4,5-tetrahydro-1H-3-benzazepine

A solution of N-allyl, N-trifluoroacetyl-2-iodo-4-chlorophenethylamine (0.76 g, 1.8 mmol) in dimethylformamide (20 mL) was treated with KOAc (0.53 g, 5.4 mmol), n-$Bu_4NBr$ (0.58 g, 1.8 mmol), $PPh_3$ (0.047 g, 0.18 mmol), $Pd(OAc)_2$ (0.041 g, 0.18 mmol) and stirred overnight at 105° C. The product mixture was cooled to 20° C., filtered, diluted with water (100 mL), extracted with ether (3×100 mL), the combined organic phases washed with water (100 mL), brine (100 mL), dried with $Na_2SO_4$ and concentrated. Flash chromatography (10% EtOAc in hexane, silica) resulted in 0.228 g of a clear oil. $^1$H NMR (400 MHz, $CDCl_3$) δ 7.29 (s, 1H), 7.18 (m, 1H), 7.04 (m, 1H), 5.38 (m, 2H), 5.40 (d, J=16 Hz, 2H), 3.80 (m, 2H), 3.00 (m, 2H). MS calculated for $C_{13}H_{11}ClF_3NO+H$: 290, observed: 290.

N-Trifluoroacetyl-8-chloro-1-methyl-2,3,4,5-tetrahydro-1H-3-benzazepine

A solution of N-trifluoroacetyl-8-chloro-1-methylene-2,3,4,5-trihydro-1H-3-benzazepine (0.16 g, 0.55 mmol) in methanol (10 mL) was treated with 10% Pd/C (0.02 g) and stirred 30 minutes under an atmosphere of hydrogen. The product mixture was filtered, concentrated and purified by flash chromatography (5% EtOAc in hexane, silica) resulting in 0.057 g of a white solid. MS calculated for $C_{13}H_{13}ClF_3NO+H$: 292, observed: 292.

8-Chloro-1-methyl-2,3,4,5-tetrahydro-1H-3-benzazepine

A solution of N-trifluoroacetyl-8-chloro-1-methyl-2,3,4,5-tetrahydro-1H-3-benzazepine (65 mg, 0.22 mmol) in methanol (2 mL) was treated with 15% aqueous NaOH (2 mL), and stirred for 3.5 hours at 60° C. The product mixture was concentrated, extracted 3 times with $CH_2Cl_2$ (5 mL), dried with $Na_2SO_4$ and concentrated to give 35 mg of a clear oil. $^1$H NMR (400 MHz, $CDCl_3$) δ 7.11 (s, 1H), 7.05 (d, J=8 Hz, 1H), 6.98 (d, J=8 Hz, 1H), 3.1-2.9 (m, 6H), 2.71 (m, 1H), 2.68 (bs, 1H), 1.32 (d, J=8 Hz, 3H). MS calculated for $C_{11}H_{14}ClN+H$: 196, observed: 196.

An additional synthesis has been reported for the preparation of the title compound and the HCl salt in PCT publication WO2005/019179.

Example 27

(R,S) 7-(2-Methyl-2H-pyrazol-3-yl)-1-methyl-2,3,4,5-tetrahydro-1H-3-benzazepine

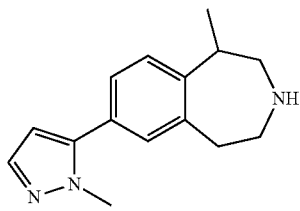 [SMILES: CC1CNCCc2cc(-c3ccnn3C)ccc21]

N-Trifluoroacetyl-7-hydroxy-1-methyl-2,3,4,5-tetrahydro-1H-3-benzazepine

A solution of N-trifluoroacetyl-7-methoxy-1-methyl-2,3,4,5-tetrahydro-1H-3-benzazepine (0.506 g, 1.76 mmol) in dichloromethane (20 mL) was treated with $BBr_3$ (4.1 mL of a 1.0M solution in $CH_2Cl_2$, 4.1 mmol) and stirred overnight while warming to 20° C. The excess $BBr_3$ was quenched with water, and the resulting mixture was diluted with ether (200 mL), washed with $Na_2CO_3$ (100 mL) and brine (100 mL), dried with $Na_2SO_4$ and concentrated. Flash chromatography (15% EtOAc in hexane, silica) resulted in 0.460 g of a white solid foam. MS calculated for $C_{13}H_{14}F_3NO_2$+H: 274, observed: 274.

N-Trifluoroacetyl-7-hydroxy-1-methyl-2,3,4,5-tetrahydro-1H-3-benzazepine, O-trifluoromethanesulfonate A solution of N-trifluoroacetyl-7-hydroxy-1-methyl-2,3,4,5-tetrahydro-1H-3-benzazepine (460 mg, 1.76 mmol) in dichloromethane (15 mL) was treated with pyridine (417 mg, 5.27 mmol), trifluoromethanesulfonic anhydride (991 mg, 3.52 mmol) and stirred 1.5 hours at 20° C. The product mixture was diluted with dichloromethane (100 mL), washed with water (50 mL), 5% aqueous HCl (50 mL), saturated aqueous $NaHCO_3$ (50 mL), brine (50 mL), dried with $Na_2SO_4$ and concentrated. Flash chromatography (15% EtOAc in hexane, silica) resulted in 658 mg of a clear oil. MS calculated for $C_{14}H_{13}F_6NO_4S$+H: 406, observed: 406.

N-Trifluoroacetyl-7-(2-Methyl-2H-pyrazol-3-yl)-1-methyl-2,3,4,5-tetrahydro-1H-3-benzazepine To a solution of N-trifluoroacetyl-7-hydroxy-1-methyl-2,3,4,5-tetrahydro-1H-3-benzazepine, O-trifluoromethanesulfonate (100 mg, 0.25 mmol) in dimethylformamide (2 mL) was treated with (2-methyl-2H-pyrazol-3-yl)-tri-n-butyltin (138 mg, 0.37 mmol), LiCl (21 mg, 0.50 mmol), Pd (PPh$_3$)$_2$Cl$_2$ (35 mg, 0.05 mmol) and stirred at 100° C. for 4 hours. The product mixture was diluted with EtOAc (20 mL), washed twice with water (10 mL), once with brine (10 mL), dried with $Na_2SO_4$ and concentrated. Flash chromatography (30% EtOAc in hexane, silica) resulted in 80 mg of a clear oil. MS calculated for $C_{17}H_{18}F_3N_3O$+H: 338, observed: 338.

7-(2-Methyl-2H-pyrazol-3-yl)-1-methyl-2,3,4,5-tetrahydro-1H-3-benzazepine

A solution of N-trifluoroacetyl-7-(2-Methyl-2H-pyrazol-3-yl)-1-methyl-2,3,4,5-tetrahydro-1H-3-benzazepine (48 mg, 0.14 mmol) in methanol (2 mL) was treated with 15% aqueous NaOH (2 mL), and the solution stirred overnight at 20° C. The product mixture was concentrated, extracted 3 times with $CH_2Cl_2$ (5 mL), dried with $Na_2SO_4$ and the solvent evaporated. Flash chromatography (0-15% MeOH in $CH_2Cl_2$, silica) resulted in 30 mg of a clear oil. $^1$H NMR (400 MHz, CDCl$_3$) δ 7.48 (s, 1H), 7.21 (m, 2H), 7.13 (s, 1H), 6.27 (s, 1H), 3.89 (s, 3H), 3.3-2.9 (m, 9H), 2.79 (dd, J=7, 14 Hz, 1H), 1.40 (d, J=8 Hz, 3H). MS calculated for $C_{15}H_{19}N_3$+H: 242, observed: 242.

Example 28

(R,S) 7-(4-Bromo-2-methyl-2H-pyrazol-3-yl)-1-methyl-2,3,4,5-tetrahydro-1H-3-benzazepine

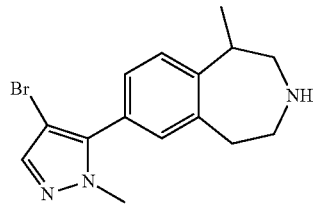 [SMILES: CC1CNCCc2cc(-c3c(Br)cnn3C)ccc21]

N-Trifluoroacetyl-7-(4-bromo-2-Methyl-2H-pyrazol-3-yl)-1-methyl-2,3,4,5-tetrahydro-1H-3-benzazepine To a solution of N-trifluoroacetyl-7-(2-Methyl-2H-pyrazol-3-yl)-1-methyl-2,3,4,5-tetrahydro-1H-3-benzazepine (30 mg, 0.082 mmol) in dichloromethane (1 mL) was treated with N-bromosuccinimide (15.3 mg, 0.086 mmol) and stirred overnight at 20° C. The product mixture was absorbed on silica and purified by flash chromatography (2-5% MeOH in $CH_2Cl_2$, silica) resulting in 37 mg of a white crystalline solid. MS calculated for $C_{17}H_{17}BrF_3N_3O$+H: 416, observed: 416.

7-(4-Bromo-2-methyl-2H-pyrazol-3-yl)-1-methyl-2,3,4,5-tetrahydro-1H-3-benzazepine A solution of N-trifluoroacetyl-7-(4-bromo-2-Methyl-2H-pyrazol-3-yl)-1-methyl-2,3,4,5-tetrahydro-1H-3-benzazepine (37 mg, 0.089 mmol) in methanol (2 mL) was treated with of 15% aqueous NaOH (2 mL), and stirred overnight at 20° C. The product mixture was concentrated, extracted 3 times with $CH_2Cl_2$ (5 mL), dried with $Na_2SO_4$ and the solvent evaporated. Flash chromatography (0-15% MeOH in $CH_2Cl_2$, silica) resulted in 28 mg of a clear oil. $^1$H NMR (400 MHz, CDCl$_3$) δ 7.50 (s, 1H), 7.25 (d, J=8 Hz, 1H), 7.17 (d, J=8 Hz, 1H), 7.10 (s, 1H), 3.83 (s, 3H), 3.17 (m, 1H), 3.1-2.9 (m, 8H), 2.80 (dd, J=7, 13 Hz, 1H), 2.48 (bs, 1H), 1.40 (d, J=8 Hz, 3H). MS calculated for $C_{15}H_{18}BrN_3$+H: 320, observed: 320.

Example 29

(R,S) 7-(3-Chlorophenyl)-1-methyl-2,3,4,5-tetrahydro-1H-3-benzazepine

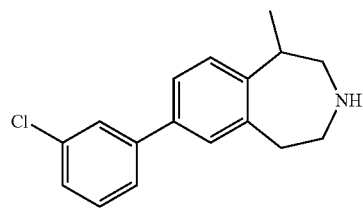 [SMILES: CC1CNCCc2cc(-c3cccc(Cl)c3)ccc21]

A solution of N-trifluoroacetyl-7-hydroxy-1-methyl-2,3,4,5-tetrahydro-1H-3-benzazepine, O-trifluoromethanesulfonate (50 mg, 0.123 mmol) in 1,4-dioxane (1.5 mL) was treated with 2-chlorophenylboronic acid (39 mg, 0.243 mmol), CsF (56 mg, 0.37 mmol), water (50 mg, 2.78 mmol), Pd(PPh$_3$)$_4$ (29 mg, 0.025 mmol) and stirred overnight at 75° C. The product mixture was diluted with EtOAc (20 mL), washed with water (10 mL), brine (10 mL), dried with Na$_2$SO$_4$ and concentrated. Flash chromatography (10-20% EtOAc in hexane, silica) resulted in 45 mg of a clear oil. MS calculated for C$_{19}$H$_{17}$ClF$_3$NO+H: 368, observed: 368. The product (27 mg, 0.073 mmol) was dissolved in methanol (2 mL) treated with 15% aqueous NaOH (2 mL), and stirred overnight at 20° C. The product mixture was concentrated, extracted 3 times with CH$_2$Cl$_2$ (5 mL), dried with Na$_2$SO$_4$ and the solvent evaporated to give 18 mg of a clear oil. $^1$H NMR (400 MHz, CDCl$_3$) δ 7.54 (s, 1H), 7.42 (d, J=6 Hz, 1H), 7.35-7.21 (m, 5H), 3.14 (m, 1H), 3.1-2.9 (m, 8H), 2.80 (bm, 2H), 1.38 (d, J=8 Hz, 3H). MS calculated for C$_{17}$H$_{18}$ClN$_3$+H: 272, observed: 272.

Example 30

(R,S) 7-(2-Chlorophenyl)-1-methyl-2,3,4,5-tetrahydro-1H-3-benzazepine

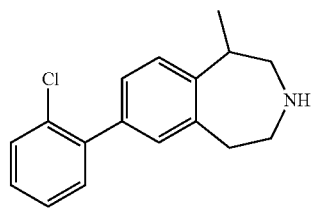 [SMILES: CC1CNCCc2cc(-c3ccccc3Cl)ccc21]

A solution of N-trifluoroacetyl-7-hydroxy-1-methyl-2,3,4,5-tetrahydro-1H-3-benzazepine, O-trifluoromethanesulfonate (50 mg, 0.123 mmol) in 1,4-dioxane (1.5 mL) was treated with 2-chlorophenylboronic acid (39 mg, 0.243 mmol), CsF (56 mg, 0.37 mmol), water (50 mg, 2.78 mmol), Pd(PPh$_3$)$_4$ (29 mg, 0.025 mmol) and stirred overnight at 75° C. The product mixture was diluted with EtOAc (20 mL), washed with water (10 mL), brine (10 mL), dried with Na$_2$SO$_4$ and concentrated. Flash chromatography (10-20% EtOAc in hexane, silica) resulted in 36 mg of a clear oil. MS calculated for C$_{19}$H$_{17}$ClF$_3$NO+H: 368, observed: 368. The product (27 mg, 0.073 mmol) was dissolved in methanol (2 mL) treated with 15% aqueous NaOH (2 mL), and stirred overnight at 20° C. The product mixture was concentrated, extracted 3 times with CH$_2$Cl$_2$ (5 mL), dried with Na$_2$SO$_4$ and the solvent evaporated to give 24 mg of a clear oil. $^1$H NMR (400 MHz, CDCl$_3$) δ 7.44 (d, J=8 Hz, 1H), 7.35-7.22 (m, 5H), 7.15 (s, 1H), 3.14 (m, 1H), 3.1-2.9 (m, 8H), 2.80 (dd, J=13, Hz, 1H), 2.51 (bs, 1H), 1.38 (d, J=8 Hz, 3H). MS calculated for C$_{17}$H$_{18}$ClN$_3$+H: 272, observed: 272.

Example 31

(R,S) 8-Chloro-1-hydroxy-2,3,4,5-tetrahydro-1H-3-benzazepine

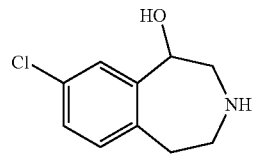 [SMILES: OC1CNCCc2ccc(Cl)cc21]

N-Trifluoroacetyl-8-chloro-1-oxo-,3,4,5-trihydro-1H-3-benzazepine

A solution of N-trifluoroacetyl-8-chloro-1-methylene-3,4,5-trihydro-1H-3-benzazepine (0.23 g, 0.80 mmol) in 1:1 methanol/dichloromethane (45 mL) was cooled to −78° C., treated with ozone until the solution turned blue (about 20 minutes), PPh$_3$ (0.21 g, 0.80 mmol) was added and the resulting solution was stirred 90 minutes while warming to 20° C. The product mixture was concentrated and purified by flash chromatography (30% EtOAc in hexane, silica) resulting in 0.215 g of a white solid. MS calculated for C$_{12}$H$_9$ClF$_3$NO$_2$+H: 292, observed: 292.

8-Chloro-1-hydroxy-2,3,4,5-tetrahydro-4H-3-benzazepine

A solution of N-trifluoroacetyl-8-chloro-1-oxo-3,4,5-trihydro-1H-3-benzazepine (50 mg, 0.17 mmol) in methanol (2 mL) was treated with NaBH$_4$ and the resulting mixture was stirred 16 hours at 20° C. The white solid product was collected by filtration, washed with water and dried, resulting in 30 mg of a white solid. $^1$H NMR (400 MHz, CD$_3$OD) δ 7.39 (s, 1H), 7.12 (d, J=8 Hz, 1H), 7.06 (d, J=8 Hz, 1H), 4.74 (d, J=8 Hz, 1H), 3.1-2.7 (m, 6H). MS calculated for C$_{10}$H$_{12}$ClNO+H: 198, observed: 198.

Example 32

(R,S) 8-Bromo-1-methyl-2,3,4,5-tetrahydro-1H-3-benzazepine

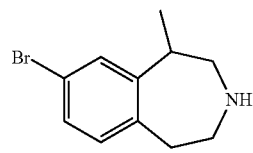

By the same general procedure as in example 26, (R,S) 8-bromo-1-methyl-2,3,4,5-tetrahydro-1H-3-benzazepine was obtained from 4-bromophenethylamine as a colorless oil. $^1$H NMR (400 MHz, CDCl$_3$) δ 7.27 (s, 1H), 7.22 (d, J=8 Hz, 1H), 6.94 (d, J=8 Hz, 1H), 3.1-2.85 (m, 6H), 2.72 (m, 1H), 2.25 (bs, 1H), 1.33 (d, J=7 Hz, 3H). MS calculated for $C_{11}H_{14}BrN+H$: 240, observed: 240.

Example 33

(R,S) 8-Fluoro-1-methyl-2,3,4,5-tetrahydro-1H-3-benzazepine

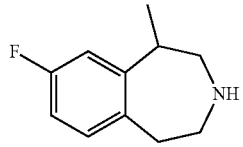

By the same general procedure as in example 26, (R,S) 8-fluoro-1-methyl-2,3,4,5-tetrahydro-1H-3-benzazepine was obtained from 4-fluorophenethylamine as a colorless oil. $^1$H NMR (400 MHz, CDCl$_3$) δ 7.00 (dd, J=8, 10 Hz, 1H), 6.86 (d, J=10 Hz, 1H), 6.76 (d, J=8 Hz, 1H), 3.08-2.56 (m, 7H), 1.85 (bs, 1H), 1.31 (d, J=7 Hz, 3H). MS calculated for $C_{11}H_{14}FN+H$: 180, observed: 180.

Example 34

(R,S) 7-Fluoro-1-methyl-2,3,4,5-tetrahydro-1H-3-benzazepine

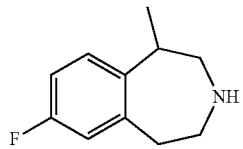

By the same general procedure as in example 26, (R,S) 7-fluoro-1-methyl-2,3,4,5-tetrahydro-1H-3-benzazepine was obtained from 3-fluorophenethylamine as a colorless oil. $^1$H NMR (400 MHz, CDCl$_3$) δ 7.09 (dd, J=6, 8 Hz, 1H), 6.85-6.78 (m, 2H), 3.10-2.89 (m, 6H), 2.71 (dd, J=7, 13 Hz, 1H), 1.91 (bs, 1H), 1.33 (d, J=7 Hz, 3H). MS calculated for $C_{11}H_{14}FN+H$: 180, observed: 180.

Example 35

(R,S) 7-Chloro-1-methyl-2,3,4,5-tetrahydro-1H-3-benzazepine

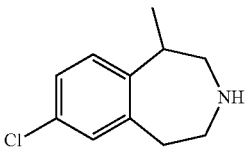

By the same general procedure as in example 26, (R,S) 7-chloro-1-methyl-2,3,4,5-tetrahydro-1H-3-benzazepine was obtained from 3-chlorophenethylamine as a colorless oil. $^1$H NMR (400 MHz, CDCl$_3$) δ 7.10 (d, J=8 Hz, 1H), 7.06 (m, 2H), 3.1-2.9 (m, 6H), 2.70 (dd, J=13, 7 Hz, 1H), 1.89 (bs, 1H), 1.31 (d, J=7 Hz, 3H). MS calculated for $C_{11}H_{14}ClN+H$: 196, observed: 196.

Example 36

(R,S) 7,8-Dichloro-1-m

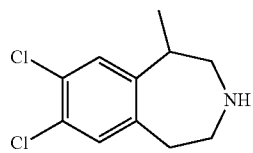

By the same general procedure as in example 26, (R,S) 7,8-dichloro-1-methyl-2,3,4,5-tetrahydro-1H-3-benzazepine was obtained from 3,4-dichlorophenethylamine as a colorless oil. $^1$H NMR (400 MHz, CDCl$_3$) δ 7.20 (s, 1H), 7.16 (s, 1H), 3.05-2.86 (m, 6H), 2.71 (dd, J=7, 13 Hz, 1H), 1.83 (bs, 1H), 1.33 (d, J=7 Hz, 3H). MS calculated for $C_{11}H_{13}Cl_2N+H$: 230, observed: 230.

Example 37

(R,S) N-Methyl-8-chloro-1-methyl-2,3,4,5-tetrahydro-1H-3-benzazepine

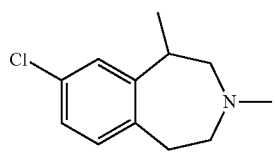

By the same general procedure as in example 9, (R,S) N-methyl-8-chloro-1-methyl-2,3,4,5-tetrahydro-1H-3-benzazepine was obtained from (R,S) 8-chloro-1-methyl-2,3,4,5-tetrahydro-1H-3-benzazepine as a colorless oil. MS calculated for $C_{12}H_{16}ClN+H$: 210, observed: 210.

Example 38

(R,S) 1-Methyl-7-trifluoromethoxy-2,3,4,5-tetrahydro-1H-3-benzazepine

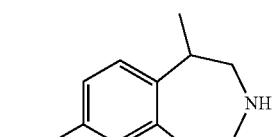

By the same general procedure as in example 26, (R,S) 1-methyl-7-trifluoromethoxy-2,3,4,5-tetrahydro-1H-3-benzazepine was obtained from 3-trifluoromethoxyphenethylamine as a colorless oil. $^1$H NMR (400 MHz, CD$_3$OD) δ 7.39 (d, J=8 Hz, 1H), 7.19 (m, 1H), 3.46 (m, 2H), 3.38 (d, J=13 Hz, 1H), 3.29 (m, 1H), 3.16 (m, 2H), 3.05 (dd, J=13, 9 Hz, 1H), 1.50 (d, J=8 Hz, 3H). MS calculated for $C_{12}H_{14}F_3NO+H$: 246, observed: 246.

Example 39

(R,S) 8-Iodo-1-methyl-7-trifluoromethoxy-2,3,4,5-tetrahydro-1H-3-benzazepine

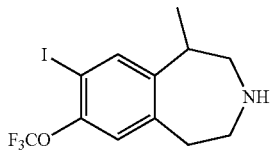

By the same general procedure as in example 3, (R,S) 8-iodo-1-methyl-7-trifluoromethoxy-2,3,4,5-tetrahydro-1H-3-benzazepine was obtained from N-trifluoroacetyl-1-methyl-7-trifluoromethoxy-2,3,4,5-tetrahydro-1H-3-benzazepine as a colorless oil. $^1$H NMR (400 MHz, CD$_3$OD) δ 7.79 (s, 1H), 7.25 (s, 1H), 3.46-3.40 (m, 3H), 3.28-3.12 (m, 3H), 3.07 (dd, J=13, 9 Hz, 1H), 1.47 (d, J=7 Hz, 3H). MS calculated for $C_{12}H_{14}F_3INO+H$: 372, observed: 372.

Example 40

(R,S) N-Propyl-8-iodo-7-methoxy-1-methyl-2,3,4,5-tetrahydro-1H-3-benzazepine

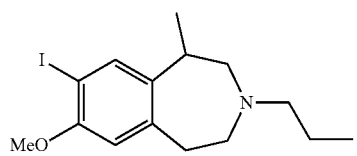 [SMILES: CCCN1CCc2cc(OC)c(I)cc2C(C)C1]

By the same general procedure as in example 10, (R,S) N-Propyl-8-iodo-7-methoxy-1-methyl-2,3,4,5-tetrahydro-1H-3-benzazepine was obtained from (R,S) 8-iodo-7-methoxy-1-methyl-1,2,4,5-tetrahydro-3H-3-benzazepine as a colorless oil. MS calculated for $C_{15}H_{22}INO+H$: 360, observed: 360.

Example 41

(R,S) 1-Ethyl-8-iodo-7-methoxy-2,3,4,5-tetrahydro-1H-3-benzazepine

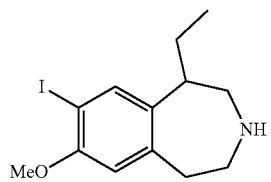 [SMILES: CCC1CNCCc2cc(OC)c(I)cc21]

By the same general procedure as in example 19, (R,S) 1-ethyl-8-iodo-7-methoxy-2,3,4,5-tetrahydro-1H-3-benzazepine was obtained from N-trifluorolacetyl-1-ethyl-7-methoxy-2,3,4,5-tetrahydro-1H-3-benzazepine as a colorless oil. $^1$H NMR (400 MHz, CDCl$_3$) δ 7.47 (s, 1H), 6.54 (s, 1H), 3.86 (s, 3H), 3.20-2.97 (m, 4H), 2.93-2.75 (m, 3H), 2.64 (m, 1H), 1.78 (m, 2H), 0.95 (dd, J=8, 8 Hz, 3H). MS calculated for $C_{13}H_{18}INO+H$: 332, observed: 332.

Example 42

(R,S) 7-(3-Methoxyphenyl)-1-methyl-2,3,4,5-tetrahydro-1H-3-benzazepine

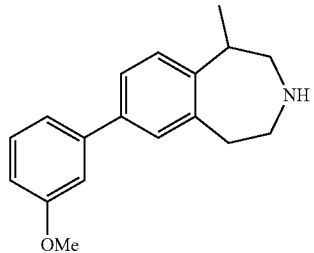 [SMILES: COc1cccc(-c2ccc3c(c2)CCNCC3C)c1]

By the same general procedure as in example 29, (R,S) 7-(3-Methoxyphenyl)-1-methyl-2,3,4,5-tetrahydro-1H-3-benzazepine was obtained from N-trifluoroacetyl-7-hydroxy-1-methyl-2,3,4,5-tetrahydro-1H-3-benzazepine, O-trifluoromethanesulfonate as a colorless oil. $^1$H NMR (400 MHz, CDCl$_3$) δ 7.37 (dd, J=7, 7 Hz, 1H), 7.30 (m, 2H), 7.21 (d, J=7 Hz, 1H), 7.14 (d, J=7 Hz, 1H), 7.09 (s, 1H), 6.86 (d, J=8 Hz, 1H), 3.85 (s, 3H), 3.2-2.9 (m, 6H), 2.80 (m, 1H), 2.64 (bs, 1H), 1.38 (d, J=7 Hz, 3H). MS calculated for $C_{18}H_{21}NO+H$: 268, observed: 268.

Example 43

(R,S) 7-(2,6-difluorophenyl)-1-methyl-2,3,4,5-tetrahydro-1H-3-benzazepine

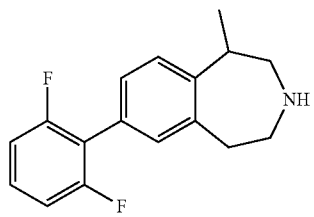 [SMILES: CC1CNCCc2cc(-c3c(F)cccc3F)ccc21]

By the same general procedure as in example 29, (R,S) 7-(2,6-difluorophenyl)-1-methyl-2,3,4,5-tetrahydro-1H-3-benzazepine was obtained from N-trifluoroacetyl-7-hydroxy-1-methyl-2,3,4,5-tetrahydro-1H-3-benzazepine, O-trifluoromethanesulfonate as a colorless oil. $^1$H NMR (400 MHz, CDCl$_3$) δ 7.35-7.10 (m, 5H), 6.95 (dd, J=7, 8 Hz, 1H), 3.2-2.9 (m, 6H), 2.79 (dd, J=8, 13 Hz, 1H), 2.70 (bs, 1H), 1.38 (d, J=8 Hz, 3H). MS calculated for $C_{17}H_{17}F_2N+H$: 274, observed: 274.

Example 44

(R,S) 7-(2-fluorophenyl)-8-chloro-1-methyl-2,3,4,5-tetrahydro-1H-3-benzazepine

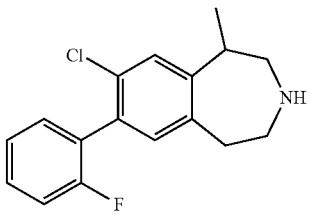 [SMILES: CC1CNCCc2cc(-c3ccccc3F)c(Cl)cc21]

By the same general procedure as in example 29, (R,S) 7-(2-fluorophenyl)-8-chloro-1-methyl-2,3,4,5-tetrahydro-1H-3-benzazepine was obtained from N-trifluoroacetyl-8-chloro-7-hydroxy-1-methyl-2,3,4,5-tetrahydro-1H-3-benzazepine as a colorless oil. $^1$H NMR (400 MHz, CDCl$_3$) δ 7.35-7.23 (m, 3H), 7.19-7.09 (m, 2H), 7.03 (s, 1H), 3.15-2.85 (m, 7H), 2.76 (dd, J=8, 13 Hz, 1H), 1.36 (d, J=8 Hz, 3H). MS calculated for C$_{17}$H$_{17}$ClFN+H: 290, observed: 290.

Example 45

(R,S) 7-(2-Trifluoromethylphenyl)-1-methyl-2,3,4,5-tetrahydro-1H-3-benzazepine

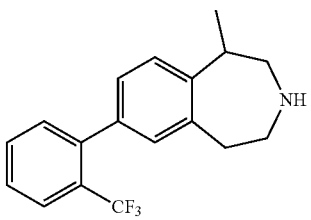 [SMILES: CC1CNCCc2cc(-c3ccccc3C(F)(F)F)ccc21]

By the same general procedure as in example 29, (R,S) 7-(2-trifluoromethylphenyl)-1-methyl-2,3,4,5-tetrahydro-1H-3-benzazepine was obtained from N-trifluoroacetyl-7-hydroxy-1-methyl-2,3,4,5-tetrahydro-1H-3-benzazepine, O-trifluoromethanesulfonate as a colorless oil. $^1$H NMR (400 MHz, CDCl$_3$) δ 7.71 (d, J=8 Hz, 1H), 7.52 (dd, J=7, 8 Hz, 1H), 7.42 (dd, J=7, 8 Hz, 1H), 7.31 (d, J=7 Hz, 1H), 7.17 (d, J=8 Hz, 1H), 7.11 (d, J=8 Hz, 1H), 3.15 (m, 1H), 3.1-2.9 (m, 5H), 2.76 (dd, J=8, 13 Hz, 1H), 2.37 (bs, 1H), 1.38 (d, J=8 Hz, 3H). MS calculated for C$_{18}$H$_{18}$F$_3$N+H: 306, observed: 306.

Example 46

(R,S) 7-(3-Trifluoromethylphenyl)-1-methyl-2,3,4,5-tetrahydro-1H-3-benzazepine

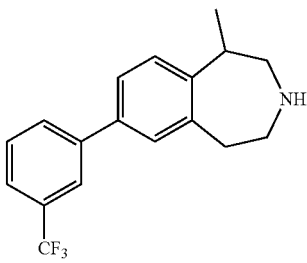 [SMILES: CC1CNCCc2cc(-c3cccc(C(F)(F)F)c3)ccc21]

By the same general procedure as in example 29, (R,S) 7-(3-trifluoromethylphenyl)-1-methyl-2,3,4,5-tetrahydro-1H-3-benzazepine was obtained from N-trifluoroacetyl-7-hydroxy-1-methyl-2,3,4,5-tetrahydro-1H-3-benzazepine, O-trifluoromethanesulfonate as a colorless oil. $^1$H NMR (400 MHz, CDCl$_3$) δ 7.80 (s, 1H), 7.73 (d, J=8 Hz, 1H), 7.57-7.48 (m, 2H), 7.38 (d, J=8 Hz, 1H), 7.30 (s, 1H), 7.24 (d, J=7 Hz, 1H), 3.16 (m, 1H), 3.1-2.9 (m, 6H), 2.79 (dd, J=8, 13 Hz, 1H), 1.38 (d, J=8 Hz, 3H). MS calculated for C$_{18}$H$_{18}$F$_3$N+H: 306, observed: 306.

Example 47

(R,S) 7-(4-Trifluoromethylphenyl)-1-methyl-2,3,4,5-tetrahydro-1H-3-benzazepine

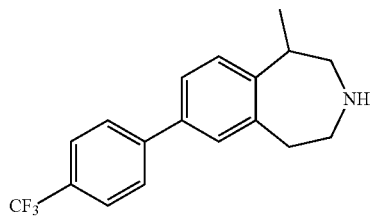 [SMILES: CC1CNCCc2cc(-c3ccc(C(F)(F)F)cc3)ccc21]

By the same general procedure as in example 29, (R,S) 7-(4-trifluoromethylphenyl)-1-methyl-2,3,4,5-tetrahydro-1H-3-benzazepine was obtained from N-trifluoroacetyl-7-hydroxy-1-methyl-2,3,4,5-tetrahydro-1H-3-benzazepine, O-trifluoromethanesulfonate as a colorless oil. $^1$H NMR (400 MHz, CDCl$_3$) δ 7.65 (s, 4H), 7.38 (d, J=8 Hz, 1H), 7.31 (s, 1H), 7.24 (d, J=8 Hz, 1H), 3.15 (m, 1H), 3.1-2.9 (m, 5H), 2.80 (dd, J=8, 13 Hz, 1H), 2.48 (bs, 1H), 1.38 (d, J=8 Hz, 3H). MS calculated for C$_{18}$H$_{18}$F$_3$N+H: 306, observed: 306.

Example 48

(R,S) 8-(2-Chlorophenyl)-1-methyl-2,3,4,5-tetrahydro-1H-3-benzazepine

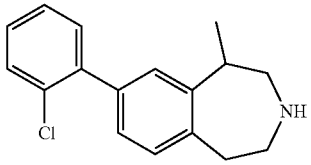 [SMILES: CC1CNCCc2ccc(-c3ccccc3Cl)cc21]

A solution of N-trifluoroacetyl-8-bromo-1-methyl-2,3,4,5-tetrahydro-1H-3-benzazepine (84 mg, 0.229 mmol) in dimethylformamide (2.5 mL) was treated with 2-chlorophenylboronic acid (43 mg, 0.275 mmol), CsF (52 mg, 0.34 mmol), water (70 mg, 3.9 mmol), Pd(PPh$_3$)$_4$ (27 mg, 0.023 mmol) and stirred overnight at 75° C. The product mixture was diluted with EtOAc (20 mL), washed with water (10 mL), brine (10 mL), dried with Na$_2$SO$_4$ and concentrated. Flash chromatography (10-20% EtOAc in hexane, silica) resulted in 36 mg of a clear oil. MS calculated for C$_{19}$H$_{17}$ClF$_3$NO+H: 368, observed: 368. The product (39 mg, 0.106 mmol) was dissolved in methanol (2 mL) treated with 15% aqueous NaOH (2 mL), and stirred overnight at 20° C. The product mixture was concentrated, extracted 3 times with CH$_2$Cl$_2$ (5 mL), dried with Na$_2$SO$_4$ and the solvent evaporated to give 18 mg of a clear oil. $^1$H NMR (400 MHz, CDCl$_3$) δ 7.44 (d, J=8 Hz, 1H), 7.35-7.17 (m, 5H), 7.12 (d, J=8 Hz, 1H), 3.14 (m, 1H), 3.1-2.9 (m, 5H), 2.79 (dd, J=7, 13 Hz, 1H), 2.36 (bs, 1H), 1.36 (d, J=7 Hz, 3H). MS calculated for $C_{17}H_{18}ClN_3$+H: 272, observed: 272.

Example 49

(R,S) 7-Methoxy-1-methyl-8-trifluoromethyl-2,3,4,5-tetrahydro-1H-3-benzazepine

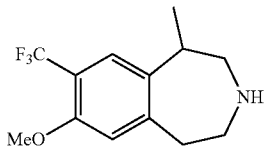 [SMILES: COc1cc2c(cc1C(F)(F)F)C(C)CNCC2]

A solution of N-trifluoromethylacetyl-8-iodo-7-methoxy-1-methyl-1,2,4,5-tetrahydro-3H-3-benzazepine (135 mg, 0.327 mmol) in dimethylformamide (3 mL) and toluene (0.5 mL) was treated with sodium trifluoroacetate (133 mg, 0.981 mmol), copper (I) iodide (124 mg, 0.654 mmol) and the toluene distilled off to remove any residual water. The reaction mixture was stirred at 155° C. for 3.5 hours, diluted with EtOAc, filtered, absorbed on silica and purified by flash chromatography (10% EtOAc in hexane, silica) resulting in 26 mg of a colorless oil. MS calculated for $C_{15}H_{15}F_6NO_2$+H: 356, observed: 356. The intermediate (26 mg, 0.073 mmol) in methanol (2 mL) was treated with 15% aqueous NaOH (2 mL), and stirred 0.5 hours at 50° C. The product mixture was diluted with water (5 mL), extracted twice with EtOAc (5 mL), the combined organic phases were washed with brine (5 mL), dried with $Na_2SO_4$ and concentrated to give 14 mg of a colorless oil. $^1$H NMR (400 MHz, $CDCl_3$) δ 7.32 (s, 1H), 6.73 (s, 1H), 3.89 (s, 3H), 3.1-2.9 (bm, 6H), 2.75 (bm, 1H), 2.23 (bs, 1H), 1.36 (d, J=8 Hz, 3H). MS calculated for $C_{13}H_{16}F_3NO$+H: 260, observed: 260.

Example 50

(R,S) 7-Methoxy-1-methyl-8-pentafluoroethyl-2,3,4,5-tetrahydro-1H-3-benzazepine

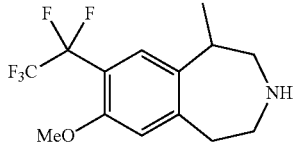 [SMILES: COc1cc2c(cc1C(F)(F)C(F)(F)F)C(C)CNCC2]

A solution of N-trifluoromethylacetyl-8-iodo-7-methoxy-1-methyl-1,2,4,5-tetrahydro-3H-3-benzazepine (100 mg, 0.242 mmol) in dimethylformamide (3 mL) and toluene (1 mL) was treated with sodium pentafluoropropionate (64 mg, 0.344 mmol), copper (I) iodide (92 mg, 0.484 mmol) and the toluene distilled off to remove any residual water. The reaction mixture was stirred at 160° C. for 3.5 hours, diluted with EtOAc, filtered, absorbed on silica and purified by flash chromatography (10% EtOAc in hexane, silica) resulting in 22 mg of a colorless oil. MS calculated for $C_{16}H_{15}F_8NO_2$+H: 406, observed: 406. The intermediate (22 mg, 0.054 mmol) in methanol (2 mL) was treated with 15% aqueous NaOH (2 mL), and stirred 0.5 hours at 50° C. The product mixture was diluted with water (5 mL), extracted twice with EtOAc (5 mL), the combined organic phases were washed with brine (5 mL), dried with $Na_2SO_4$ and concentrated to give 14 mg of a colorless oil. $^1$H NMR (400 MHz, $CDCl_3$) δ 7.25 (s, 1H), 6.74 (s, 1H), 3.85 (s, 3H), 3.1-2.9 (bm, 6H), 2.76 (bm, 1H), 2.37 (bs, 1H), 1.35 (d, J=8 Hz, 3H). MS calculated for $C_{14}H_{16}F_5NO$+H: 310, observed: 310.

Example 51

(R,S) 8-Trifluoromethyl-1-methyl-2,3,4,5-tetrahydro-1H-3-benzazepine

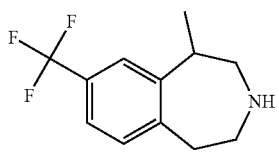 [SMILES: CC1CNCCc2ccc(C(F)(F)F)cc21]

By the same general procedure as in example 26, (R,S) 8-trifluoromethyl-1-methyl-2,3,4,5-tetrahydro-1H-3-benzazepine was obtained from 4-trifluoromethylphenethylamine as a colorless oil. $^1$H NMR (400 MHz, DMSO) δ 7.55 (d, J=8 Hz, 1H), 7.49 (s, 1H), 7.43 (d, J=8 Hz, 1H), 3.55-3.50 (m, 1H) 3.43-3.23 (m, 7H), 3.13 (dd, J=16, 7 Hz, 1H), 3.0-2.91 (m, 2H), 1.36 (d, J=7 Hz, 3H). MS calculated for $C_{12}H_{14}F_3N$+H, 230.19, observed: 230.4

Example 52

(R,S) 8-bromo-1-methoxymethyl-7-methoxy-2,3,4,5-tetrahydro-1H-3-benzazepine

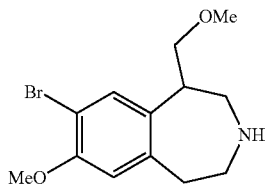 [SMILES: COCC1CNCCc2cc(OC)c(Br)cc21]

A solution of 8-bromo-1-hydroxymethyl-7-methoxy-2,3,4,5-tetrahydro-1H-3-benzazepine (0.075 g, 0.26 mmol) in dichloromethane (2 mL) was treated with $BOC_2O$ (0.062 g, 0.29 mmol), and stirred overnight at 20° C. The product was absorbed on silica and purified by flash chromatography (33% EtOAc in hexane, silica) resulting in 0.034 g of a clear oil. MS calculated for $C_{17}H_{24}BrNO_4$+H: 386, observed: 386. The BOC-protected intermediate was dissolved in dimethylformamide (1 mL), treated with excess NAH and excess iodomethane sequentially, and then stirred for 1 hour at 20° C. The reaction mixture was quenched with water (5 mL), extracted twice with EtOAc (5 mL), the combined organic phases were washed with brine (5 mL), dried with $Na_2SO_4$ and concentrated to give 0.019 g of a clear oil. MS calculated for $C_{18}H_{26}BrNO_4$+H: 400, observed: 400. The N—BOC protected methylether was then treated with 4M HCl in dioxane (1 mL) and stirred 2 hours at 20° C. Evaporation resulted in 0.009 g of the desired product as a clear oil. $^1$H NMR (400

MHz, CD₃OD) δ 7.30 (s, 1H), 6.92 (s, 1H), 3.87 (s, 3H), 3.65 (s, 3H) 3.5-3.1 (m, 9H). MS calculated for C$_{13}$H$_{16}$BrNO$_2$+H: 300, observed: 300.

Example 53

(R,S) 8-Chloro-1-ethyl-2,3,4,5-tetrahydro-1H-3-benzazepine

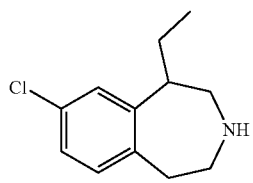

N-Crofyl, N-trifluoroacetyl-2-iodo-4-chlorophenethylamine

A solution of N-trifluoroacetyl-2-iodo-4-chlorophenethylamine (6.2 g, 15.8 mmol) in dimethylformamide (350 mL) was treated with K$_2$CO$_3$ (15.8 g, 114 mmol) and crotyl bromide (6.0 g, 44 mmol) sequentially, the mixture was stirred at 60° C. for 16 hours and then cooled to 20° C. The mixture was diluted with EtOAc (350 mL), washed with water (3×300 mL), dried with Na$_2$SO$_4$ and concentrated. Flash chromatography (5-15% EtOAc in hexane) resulted in 2.5 g of a clear oil. MS calculated for C$_{14}$H$_{14}$ClF$_3$INO+H: 432, observed: 432.

N-Trifluoroacetyl-8-chloro-1-ethyl-2,3,4,5-tetrahydro-1H-3-benzazepine

A solution of N-crotyl, N-trifluoroacetyl-2-iodo-4-chlorophenethylamine (2.5 g, 5.8 mmol) in dimethylformamide (250 mL) was treated with KOAc (1.07 g, 10.9 mmol), n-Bn$_2$Et$_2$NBr (1.33 g, 5.84 mmol), Pd(OAc)$_2$ (0.063 g, 0.28 mmol) and stirred overnight at 77° C. The product mixture was cooled to 20° C., filtered, diluted with water (100 mL), extracted with EtOAc (3×100 mL), the combined organic phases washed with water (100 mL), brine (100 mL), dried with Na$_2$SO$_4$ and concentrated. Flash chromatography (2-20% EtOAc in hexane, silica) resulted in 0.339 g of a clear oil. The product, which was assumed to be a mixture of double-bond isomers, was dissolved in methanol (50 mL) treated with Et$_3$N (0.2 mL), 10% Pd/C (0.10 g) and stirred 16 hours under 100 psi of hydrogen. The product mixture was filtered, concentrated and purified by flash chromatography (5% EtOAc in hexane, silica) resulting in 0.20 g of a white solid. MS calculated for C$_{14}$H$_{15}$ClF$_3$NO+H: 306, observed: 306.

8-Chloro-1-ethyl-2,3,4,5-tetrahydro-1H-3-benzazepine

A solution of N-trifluoroacetyl-8-chloro-1-ethyl-2,3,4,5-tetrahydro-1H-3-benzazepine (63 mg, 0.207 mmol) in methanol (2 mL) was treated with 15% aqueous NaOH (2 mL), and stirred for 3.5 hours at 60° C. The product mixture was concentrated, extracted 3 times with CH$_2$Cl$_2$ (5 mL), dried with Na$_2$SO$_4$ and concentrated to give 35 mg of a clear oil. ¹H NMR (400 MHz, DMSO-d$_6$) δ 7.2 (m, 3H), 3.3-3.0 (m, 7H), 1.9-1.6 (m, 2H), 0.91 (t, J=7 Hz, 3H). MS calculated for C$_{12}$H$_{16}$ClN+H: 210, observed: 210.

Example 54

(R,S) 8-Chloro-7-fluoro-1-methyl-2,3,4,5-tetrahydro-1H-3-benzazepine

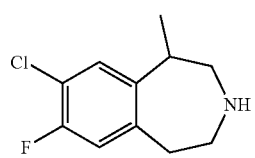

N-Trifluoroacetyl-8-chloro-7-fluoro-1-methyl-2,3,4,5-tetrahydro-1H-3-benzazepine A solution of N-trifluoroacetyl-8-chloro-1-methyl-2,3,4,5-tetrahydro-1H-3-benzazepine (2.5 g, 8.5 mmol) in 1,2-dichloroethane (15 mL) was treated with Selectfluor (3.9 g, 11 mmol), trifluoromethanesulfonic acid (8 mL, 90 mmol) and stirred 60 hours at 75° C. The product mixture was poured into water (200 mL), extracted with EtOAc (200 mL), the organic phase washed with saturated aqueous NaHCO$_3$ (2×100 mL), brine (100 mL), dried with Na$_2$SO$_4$ and concentrated. The crude product was purified by flash chromatography (6% EtOAc in hexane, silica) resulting in 1.6 g of a white solid. MS calculated for C$_{13}$H$_{12}$ClF$_4$NO+H: 310, observed: 310.

8-Chloro-7-fluoro-1-methyl-2,3,4,5-tetrahydro-1H-3-benzazepine

A solution of N-trifluoroacetyl-8-chloro-7-fluoro-1-methyl-2,3,4,5-tetrahydro-1H-3-benzazepine (160 mg, 0.22 mmol) in methanol (3 mL) was treated with 15% aqueous NaOH (2 mL), and stirred for 3.5 hours at 25° C. The product mixture was concentrated, extracted 3 times with CH$_2$Cl$_2$ (5 mL), dried with Na$_2$SO$_4$ and concentrated to give 93 mg of a clear oil. ¹H NMR (400 MHz, CDCl$_3$) δ 7.11 (m, 1H), 6.85 (m, 1H), 3.05-2.95 (m, 3H), 2.95-2.80 (m, 3H), 2.68 (m, 1H), 2.38 (bm, 1H), 1.31 (m, 3H). MS calculated for C$_{11}$H$_{13}$ClFN+H: 214, observed: 214.

Example 55

Separation of Enantiomers for Selected Compounds of the Invention

The following compounds were separated into their respective enantiomers using a Varian ProStar HPLC system with a 20 mm×250 mm Chiralcel OD chiral column, eluting with 0.2% diethylamine in various concentrations of isopropanol (IPA) in hexanes, see Table 2 below. In some cases, the separations were performed on the intermediate trifluoroacetamide protected amines.

TABLE 2

| Example | Enantiomer | Retention time for the free amine (mins) | Retention time for the trifluoro-acetamide | Conditions |
|---|---|---|---|---|
| 1 | 1 | 21.9 | | 5% IPA in hexane |
| | 2 | 24.5 | | 10 mL/min |
| 2 | 1 | 42 | | 5% IPA in hexane |
| | 2 | 47 | | 9 mL/min |
| 3 | 1 | 20.8 | | 5% IPA in hexane |
| | 2 | 24.2 | | 10 mL/min |
| 19 | 1 | 34.9 | | 1% IPA in hexane |
| | 2 | 39.5 | | 9 mL/min |
| 26 | 1 | | 23.8 [1] | 5% IPA in hexane |
| | 2 | | 29.2 [2] | 7 mL/min |
| 37 | 1 | | 23.8 [3] | 5% IPA in hexane |
| | 2 | | 29.2 [4] | 7 mL/min |
| 51 | 1 | | 18.6 [5] | 1% IPA in hexane |
| | 2 | | 21.4 [6] | 9 mL/min |
| 53 | 1 | | 13.7 [7] | 5% IPA in hexane |
| | 2 | | 20.2 [8] | 10 mL/min |

[1] The separated trifluoroacetamide enantiomer was hydrolyzed to give Enantiomer 1 of Compound 26.
[2] The separated trifluoroacetamide enantiomer was hydrolyzed to give Enantiomer 2 of Compound 26.
[3] The separated trifluoroacetamide enantiomer was hydrolyzed and subsequently N-methylated to give Enantiomer 1 of Compound 37.
[4] The separated trifluoroacetamide enantiomer was hydrolyzed and subsequently N-methylated to give Enantiomer 2 of Compound 37.
[5] The separated trifluoroacetamide enantiomer was hydrolyzed to give Enantiomer 1 of Compound 51.
[6] The separated trifluoroacetamide enantiomer was hydrolyzed to give Enantiomer 2 of Compound 51.
[7] The separated trifluoroacetamide enantiomer was hydrolyzed to give Enantiomer 1 of Compound 53.
[8] The separated trifluoroacetamide enantiomer was hydrolyzed to give Enantiomer 2 of Compound 53.

Example 56

Intracellular IP$_3$ Accumulation Assay

HEK293 cells were transfected in 15 cm sterile dishes with or without (control) 16 μg of human 5-HT$_{2C}$ receptor cDNA using 25 μl of lipofectamine. Cells were then incubated for 3-4 hours at 37° C./5% CO$_2$ and then transfection media was removed and replaced with 100 μl of DMEM. Cells were then plated onto 100 cm sterile dishes. The next day cells were plated into 96 well PDL microtiter plates at a density of 55K/0.2 ml. Six hours latter, media was exchanged with [$^3$H] inositol (0.25 μCi/well) in inositol free DMEM and plates were incubated at 37° C./5% CO$_2$ overnight. The next day, wells were aspirated and 200 μl of DMEM containing test compound, 10 μM pargyline, and 10 mM LiCl was added to appropriate wells. Plates were then incubated at 37° C./5% CO$_2$ for three hours followed aspiration and by addition of fresh ice cold stop solution (1M KOH, 19 mM Na-borate, 3.8 mM EDTA) to each well. Plates were kept on ice for 5-10 min and the wells were neutralized by addition of 200 μl of fresh ice cold neutralization solution (7.5% HCl). Plates were then frozen until further processing is desired. The lysate was then transferred into 1.5 ml Eppendorf tubes and 1 ml of chloroform/methanol (1:2) was added/tube. The solution was vortexed for 15 seconds and the upper phase was applied to a Biorad AG1-X8™ anion exchange resin (100-200 mesh). First, the resin was washed with water at 1:1.25 W/V and 0.9 ml of upper phase was loaded onto the column. The column was then washed with 10 ml of 5 mM myo-inositol and 10 ml of 5 mM Na-borate/60 mM Na-formate. The inositol tris phosphates were eluted into scintillation vials containing 10 ml of scintillation cocktail with 2 ml of 0.1 M formic acid/1 M ammonium formate. The columns were regenerated by washing with 10 ml of 0.1 M formic acid/3M ammonium formate and rinsed twice with dd H$_2$O and stored at 4° C. in water.

The biological activities in the IP Accumulation Assay for several representative compounds are shown in Table 3 below:

TABLE 3

| Compound (Example Number) | 5-HT$_{2C}$ (EC$_{50}$)* IP Accumulation Assay (nM) |
|---|---|
| 1 | 4.2 |
| 2 | 4.5 |
| 3 | 1.4 |
| 4 | 2.1 |
| 5 | 12.1 |
| 12 | 6.3 |
| 19 | 18 |
| 26 | 5.8 |
| 32 | 2.1 |

*Reported values are averages of at least two trials.

The majority of the other compounds of the Examples were tested at least once, and they showed activities in the IP Accumulation Assay in the range between ~1.4 nM and ~5 μM.

Example 57

Inhibition of Food Intake in Food-Deprived Rats

Male Sprague-Dawley rats (250-350 g) were deprived of food overnight prior to testing. Prior to food deprivation, the animals were weighed and separated into treatment groups in order to balance groups according to body weight. On the test day, animals were placed into individual cages (no bedding) at 9:00 am with free access to water. At 10:00 am, animals were injected with test compound (p.o., i.p., or s.c.) and then presented with a pre-weighed amount of food in a dish either 60 min (p.o.) or 30 min (i.p. and s.c.) after drug administration. Food consumption over different time points was then determined by weighing the food cup at 1, 2, 4, and 6 hr after the food was presented. Thus, food consumption was measured at 2, 3, 5, and 7 hr post-injection in p.o. studies, and at 1.5, 2.5, 4.5, and 6.5 hr post-injection in i.p. and s.c. studies.

FIGS. 1A-G illustrate the effects of seven different compounds on food intake in food-deprived rats. All compounds inhibited food intake dose-dependently. This effect was consistently most pronounced over the first 1 hr after food presentation. Some compounds (FIGS. 1A, 1C, and 1E) maintained an inhibitory effect on food intake relative to vehicle-treated controls at 6 hr after food presentation. Compounds were also shown to be effective via all routes of administration including p.o.

Example 58

Inhibition of Food Intake in Food-Deprived Rats Using a Selective 5Ht-2C Receptor Agonist Alone, Phentermine Alone, or a Combination of the Two Compounds Male SD rats, weight 250-275 g, were purchased from Harlan and housed 4 per cage in an animal facility in reverse day-light. Water and Chow was available (LabDiet 8604) ad libitum for two weeks. The animals were handled for 2 occasions during this time. On the morning of the study, the animals were single-housed with no food or bedding and dosed perorally with 1 ml/kg of compound or vehicle 30 minutes prior to lights out. At lights out, the animals were given a pre-weighed amount of chow and placed near the food bowl. Two hours later the remaining chow was weighed and the study concluded.

Figure 2:
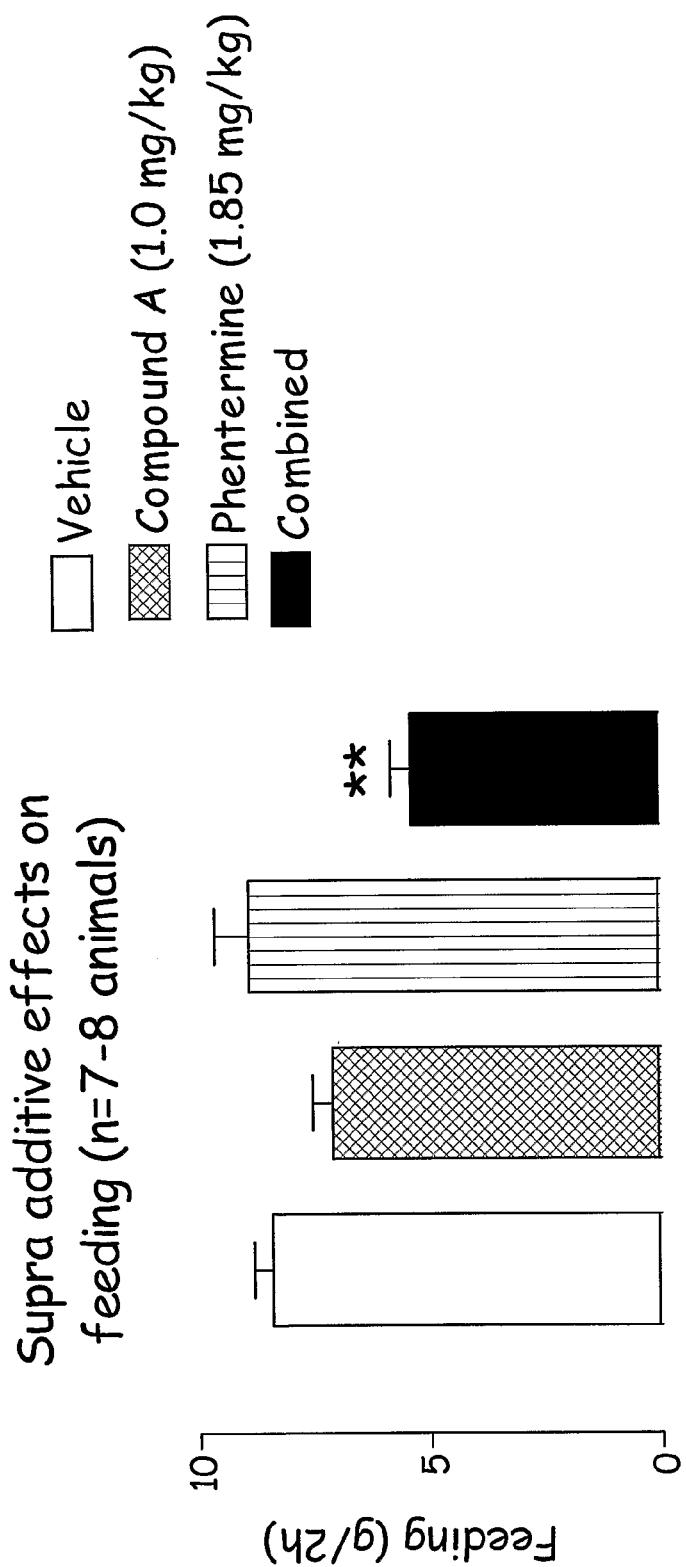
FIG. 2 shows the supra additive (synergistic) effect of phentermine and the selective 5HT-2C receptor agonist 8-Chloro-7-methoxy-1-methyl-2,3,4,5-tetrahydro-1H-3-benzazepine (Cmpd A) on feeding in rats.

FIG. 2 shows the effect on feeding of the selective 5HT-2C receptor agonist 8-Chloro-7-methoxy-1-methyl-2,3,4,5-tetrahydro-1H-3-benzazepine (Cmpd A), phentermine, and the combination. A synthesis example for 8-Chloro-7-methoxy-1-methyl-2,3,4,5-tetrahydro-1H-3-benzazepine (Cmpd A) can be found in Example 2 herein.

Example 59

Inhibition of Food Intake in Food-Deprived Rats Using a Selective 5Ht-2C Receptor Agonist Alone, Phentermine Alone, or a Combination of the Two Compounds Female (weight 225-250 g) and male (weight 250-275 g) Sprague-Dawley (SD) rats were purchased from Harlan (San Diego, Calif.) and housed 4 per cage in a temperature controlled environment under a 17 h/7 h light/dark cycle (lights out at 10:00 am). Water and Chow was available (LabDiet 8604) ad libitum for two weeks. The animals were handled for 2 occasions during this time. On the morning of the study, the animals were individually housed with no food or bedding and dosed perorally with 1 ml/kg of compound or vehicle 30 minutes prior to lights out. At lights out, the animals were given a pre-weighed amount of chow and placed near the food bowl. Two hours later the remaining chow was weighed and the study concluded.

FIG. 3 shows the effect of the selective 5HT-2C receptor agonist (R)-8-chloro-1-methyl-2,3,4,5-tetrahydro-1H-3-benzazepine (Compound B), phentermine, and the combination on food intake. A synthesis example for (R)-8-chloro-1-methyl-2,3,4,5-tetrahydro-1H-3-benzazepine (Compound B) can be found in Example 26 herein.

Figure 3A:
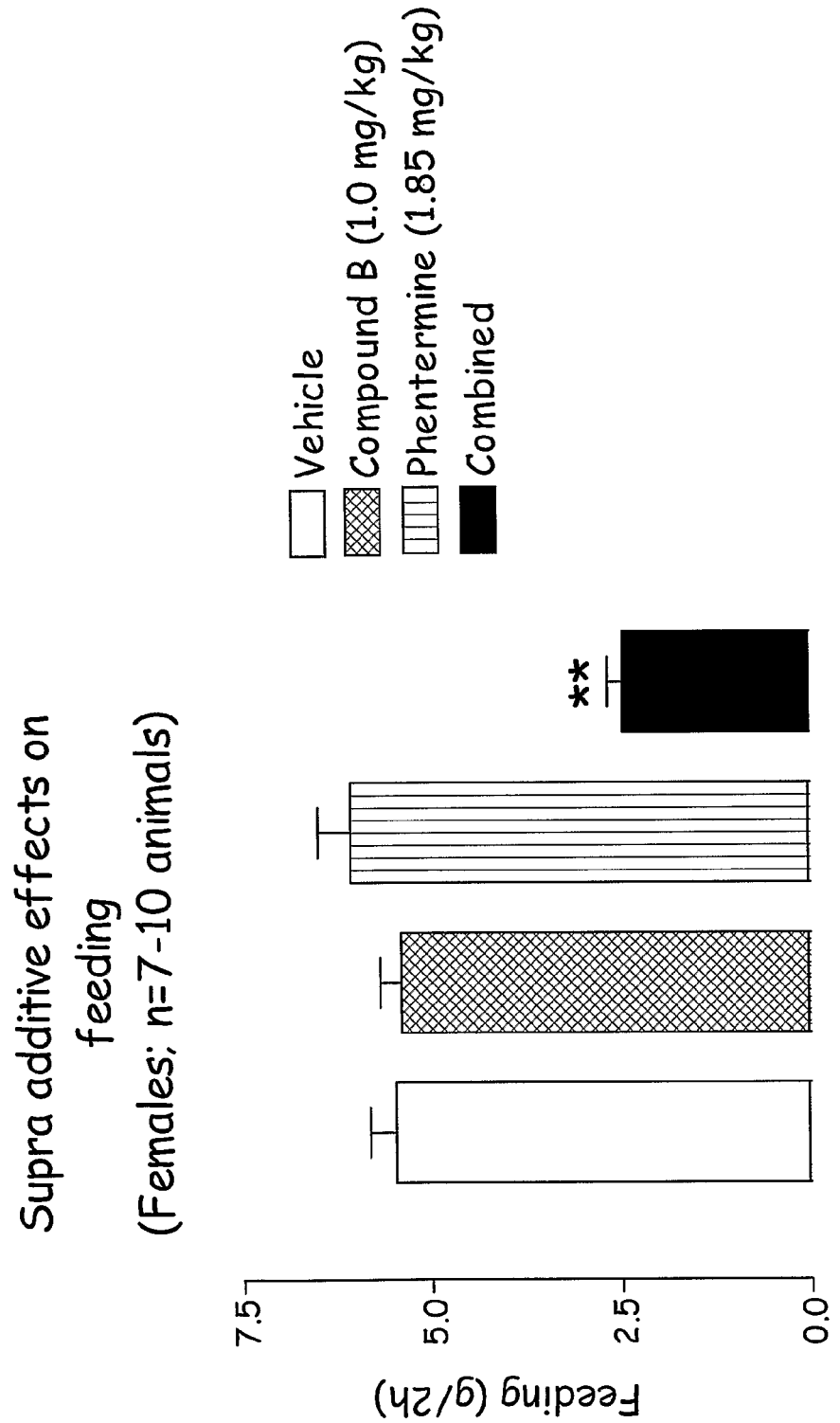
FIGS. 3A and 3B show the supra additive (synergistic) effect of phentermine and the selective 5HT-2C receptor agonist (R)-8-chloro-1-methyl-2,3,4,5-tetrahydro-1H-3-benzazepine (Cmpd B) on food intake in female (FIG. 3A) and male (FIG. 3B) rats.

The effect of Compound B, phentermine, and the combination on food intake in female rats is shown in FIG. 3A. For analysis, the data was subjected to a two-way analysis of variance (ANOVA) with phentermine and Compound B as independent factors. The analysis revealed a significant interaction between the two factors [$F(1.29)=31.6$, $p<0.01$]. Post-hoc pairways comparisons using the Bonferroni multiple comparison test revealed the Compound B+phentermine combination to differ significantly from all other groups ($p<0.01$, see FIG. 3A), evidencing a supra additive (synergistic) effect for the inhibition of food intake. No other significant differences between groups were observed.

Figure 3B:
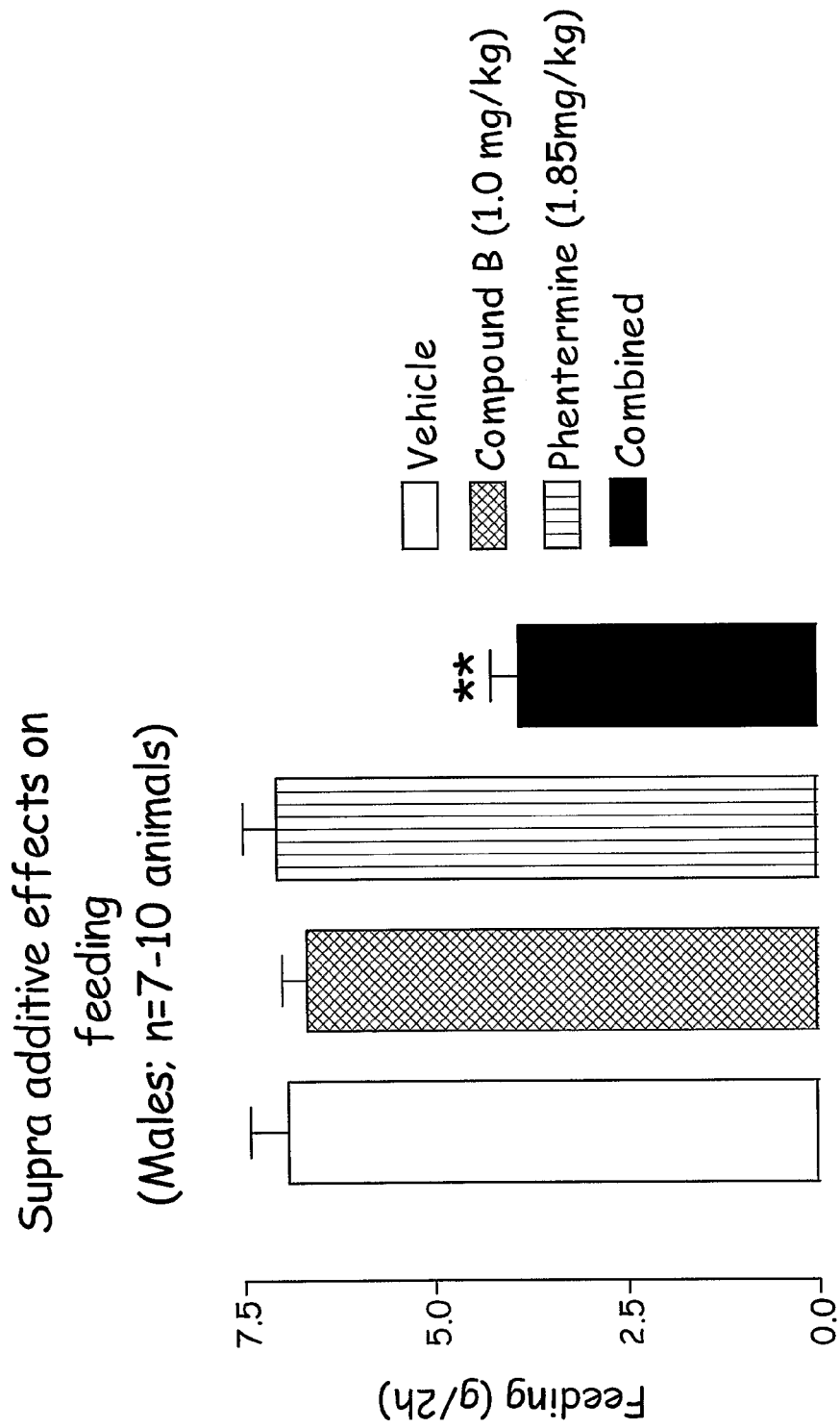

The effect of Compound B, phentermine, and the combination on food intake in male rats is shown in FIG. 3B. For analysis, the data was subjected to a two-way analysis of variance (ANOVA) with phentermine and Compound B as independent factors. The analysis revealed a significant interaction between the two factors [$F(1.29)=12.7$, $p<0.01$]. Post-hoc pairways comparisons using the Bonferroni multiple comparison test revealed the Compound B+phentermine combination to differ significantly from all other groups ($p<0.01$, see FIG. 3B), evidencing a supra additive (synergistic) effect for the inhibition of food intake. No other significant differences between groups were observed.

Example 60

Inhibition of Food Intake in Food-Deprived Rats Using a Selective 5Ht-2C Receptor Agonist Alone, Phentermine Alone, or a Combination of the Two Compounds Male and female Sprague-Dawley (SD) rats (weight 250-275 g) were purchased from Harlan (San Diego, Calif.) and housed 4 per cage in a temperature controlled environment under a 17 h/7 h light/dark cycle (lights out at 10:00 am). Water and Chow was available (LabDiet 8604) ad libitum for two weeks. The animals were handled for 2 occasions during this time. On the morning of the study, the animals were individually housed with no food or bedding and dosed perorally with 1 ml/kg of compound or vehicle 30 minutes prior to lights out. At lights out, the animals were given a pre-weighed amount of chow and placed near the food bowl. Two hours later the remaining chow was weighed and the study concluded.

Figure 4A:
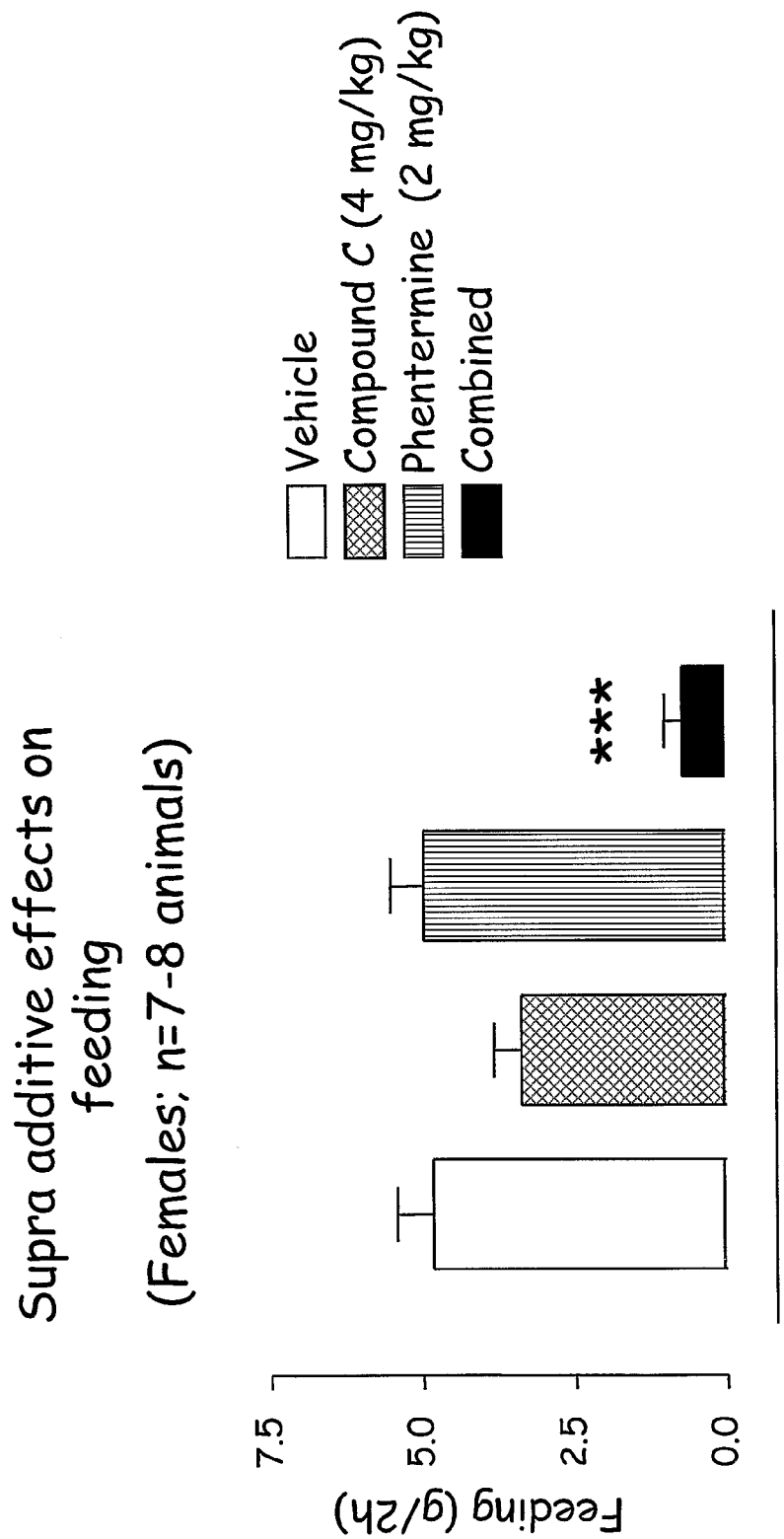
FIGS. 4A and 4B show the supra additive (synergistic) effect of phentermine and the selective 5HT-2C receptor agonist (R)-1-(5-Chloro-2-fluoro-phenyl)-2-methyl-piperazine (Cmpd C) on food intake in female (FIG. 4A) and male (FIG. 4B) rats.
Figure 4B:
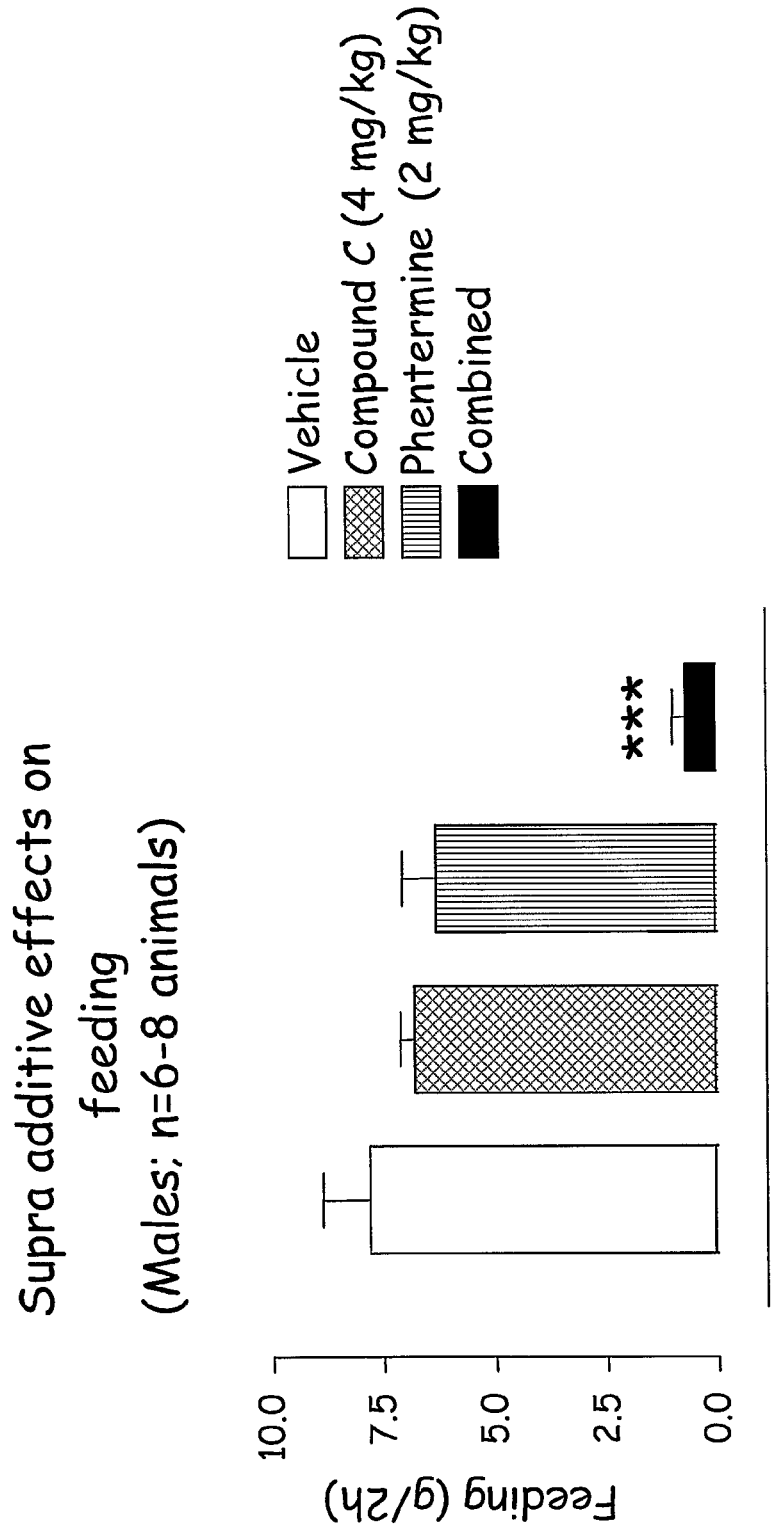

FIGS. 4A and 4B show the supra additive (synergistic) effect of phentermine and the selective 5HT-2C receptor agonist (R)-1-(5-Chloro-2-fluoro-phenyl)-2-methyl-piperazine (Cmpd C) on food intake in female (FIG. 4A) and male (FIG. 4B) rats.

Compound C is a selective 5HT-2C receptor agonist which lies outside of Formula I as disclosed herein. Compound C was prepared in a similar manner as described in PCT publication WO 2005/016902 (see Example 3.2 therein) using 2-bromo-4-chloro-1-fluorobenzene as the starting material.

It is intended that each of the patents, applications, printed publications, and other published documents mentioned or referred to in this specification be herein incorporated by reference in their entirety.

Those skilled in the art will appreciate that numerous changes and modifications can be made to the preferred embodiments of the invention and that such changes and modifications can be made without departing from the spirit of the invention. It is therefore intended that the appended claims cover all such equivalent variations as fall within the true spirit and scope of the invention.

What is claimed is:

1. A method of decreasing food intake of a mammal comprising:
administering to said mammal a dosage form of a composition comprising 1,1-dimethyl-2-phenyl-ethylamine, or a pharmaceutically acceptable salt thereof, and (R)-1-(5-chloro-2-fluoro-phenyl)-2-methyl-piperazine, or a pharmaceutically acceptable salt thereof,
wherein the 1,1-dimethyl-2-phenyl-ethylamine, or a pharmaceutically acceptable salt thereof, and the (R)-1-(5-chloro-2-fluoro-phenyl)-2-methyl-piperazine, or a pharmaceutically acceptable salt thereof, are present in a combined preparation for simultaneous, separate or sequential use.

2. The method according to claim 1, wherein the dosage form is formulated for oral administration.

3. The method according to claim 1, wherein the dosage form is formulated as a solid dosage form.

4. The method according to claim 1, wherein the dosage form is formulated as a liquid dosage form.

5. The method according to claim 1, wherein the dosage form further comprises a pharmaceutically acceptable carrier.

6. The method according to claim 1, wherein the 1,1-dimethyl-2-phenyl-ethylamine, or a pharmaceutically acceptable salt thereof, and the (R)-1-(5-chloro-2-fluoro-phenyl)-2-methyl-piperazine, or a pharmaceutically acceptable salt thereof, are provided in amounts to give a synergistic effect in decreasing food intake in a mammal.

* * * * *